United States Patent
Tchernitchin et al.

(10) Patent No.: US 9,089,526 B2
(45) Date of Patent: Jul. 28, 2015

(54) PHARMACEUTICAL PRODUCT AND ANALYSIS MODEL FOR HORMONE REPLACEMENT THERAPY FOR WOMEN AND PREVENTION OF SOME CANCERS AND UTERINE MYOMAS

(75) Inventors: Andres Tchernitchin, Santiago (CL); Leonardo Gaete, Santiago (CL); Rodrigo Bustamante, Santiago (CL)

(73) Assignee: Universidad de Chile, Santiago (CL)

( * ) Notice: Subject to any disclaimer, the term of this patent is extended or adjusted under 35 U.S.C. 154(b) by 305 days.

(21) Appl. No.: 12/802,083

(22) Filed: May 28, 2010

(65) Prior Publication Data

US 2010/0310690 A1     Dec. 9, 2010

Related U.S. Application Data

(60) Provisional application No. 61/217,566, filed on Jun. 1, 2009.

(51) Int. Cl.
*A61K 36/185* (2006.01)
*A61K 36/48* (2006.01)
*A61K 36/00* (2006.01)

(52) U.S. Cl.
CPC ............. *A61K 36/185* (2013.01); *A61K 36/48* (2013.01)

(58) Field of Classification Search
CPC ...... A61K 36/185; A61K 36/48; A61K 36/00
See application file for complete search history.

(56) References Cited

U.S. PATENT DOCUMENTS

2003/0180395 A1*   9/2003   Bueter .................. 424/725

OTHER PUBLICATIONS

Rahman. Studies in Natural Products Chemistry. Elsevier. 2008. p. 565.*

(Continued)

*Primary Examiner* — Patricia A Leith
(74) *Attorney, Agent, or Firm* — John Dodds

(57) ABSTRACT

The present disclosure describes a study of estrogenic activity present in various plant species, selectively inducing some but not all estrogenic responses in the uterus. Prepubertal female rats were treated sequentially with various extracts or decoctions of different plant species or its vehicle, followed 1 h later by treatment with estradiol-17β (E) or its solvent. Uteri were excised under anesthesia and histologically processed for eosinophil quantification and morphometric evaluation of various uterine responses to estrogen, at 6 or 24 h after hormone or vehicle treatment. Besides extracts or decoctions, pure phytoestrogens were also used. Additionally, human mammary cancer cells MCF-7 or MDAMB-231 were cultured in presence of the extract (or decoction), E, both or solvent and cell proliferation was evaluated. Various extracts or decoction displayed selective estrogenic and/or antiestrogenic action for some but not all parameters of estrogen stimulation in the uterus and inhibited growth of human mammary cells in culture or antagonized the estrogen-induced increase in their growth. Present results reveal, for the first time, a dissociation of responses to estrogen by phytoestrogens, suggesting its possible therapeutic application as estrogenic compounds not inducing cell proliferation and reveal the anticancerous effect of some of the extracts with possible therapeutic relevance. The dissociation of responses to estrogen additionally suggest therapeutic applications in estrogen-related diseases (for instance, premenstrual syndrome, endometriosis, etc.); the inhibition of eosinophil degranulation suggest an application in diseases related to eosinophils (hypereosinophilic syndrome, allergic and hypersensitivity diseases).

7 Claims, 83 Drawing Sheets

(56) References Cited

Figure 1:
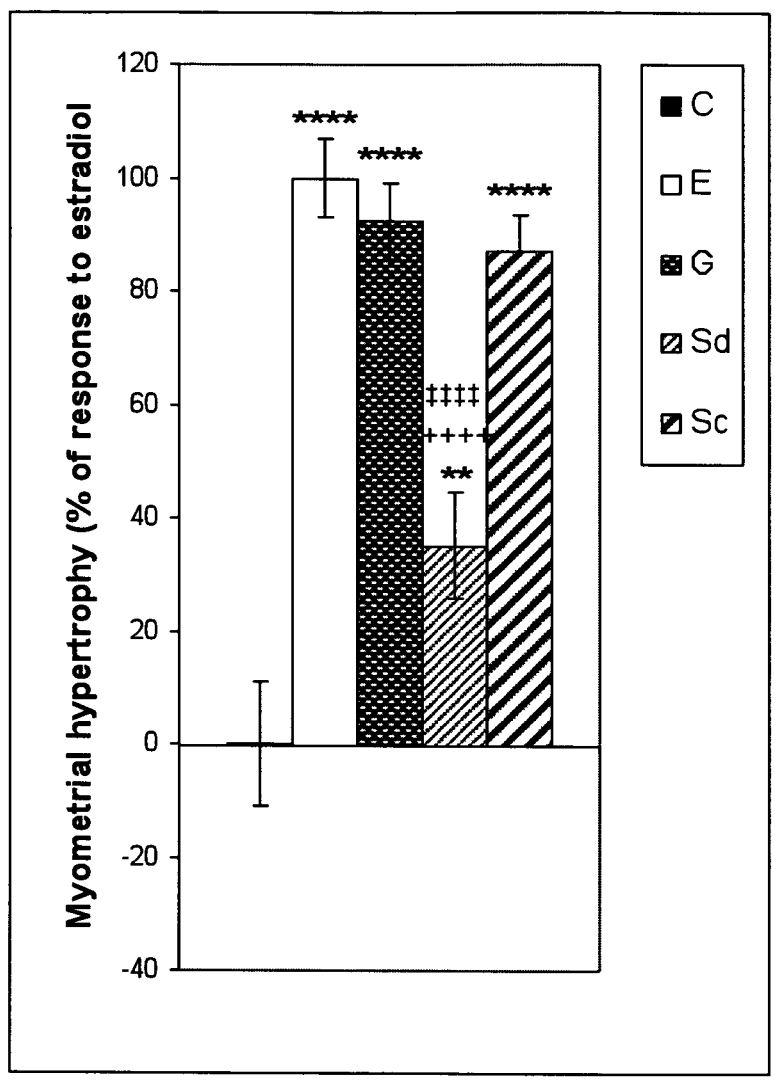

OTHER PUBLICATIONS flickr.com. Retrieved from the internet on Jan. 25, 2012. <http://www.flickr.com/photos/mark_egger_castilleja/collections/72157618313064250/>. 1 page.*

Pennell. The Genus *Calceolaria* in Southeastern Peru. Proceedings of the Academy of Natural Sciences of Philadelphia. 1945; 97. pp. 137-177.*

Ladio et al. Comparison of traditional wild plant knowledge between aboriginal communities inhabiting arid and forest environments in Patagonia, Argentina. Journal of Arid Environments. 69 (2007). pp. 695-715.*

Keville. Herbal Tinctures. Vegetarian Times. Active Media Interest, Inc. Sep. 1981. pp. 37-38.*

Martin. Ethnobotany: a methods manual. Earthscan. 2004. pp. 84-86.*

H.B. MacPhillamy: Drugs From Plants; Plant Science Bulletin, Botanical Society of America, vol. 9, No. 2, Apr. 1963.*

Phillipson, J. New Drugs From Nature—It Could Be Yew; Phytotherapy Research 13 (1999) pp. 2-8.*

Raskin et al. Can an Apple a Day Keep the Doctor Away? Current Pharmaceutical Design, 2004, 10, 3419-3429.*

Revilla et al. Comparison of Several Procedures Used for the Extraction of Anthocynains From Red Grapes; J. Agric. Food Chem. 1998, 46, pp. 4592-4597.*

* cited by examiner

PHARMACEUTICAL PRODUCT AND ANALYSIS MODEL FOR HORMONE REPLACEMENT THERAPY FOR WOMEN AND PREVENTION OF SOME CANCERS AND UTERINE MYOMAS

PRIORITY

This application claims priority of the U.S. provisional application No. 61/217,566 filed on Jun. 1, 2009.

TECHNICAL FIELD OF THE INVENTION

This invention relates to the field of phytochemistry. Particularly it relates to use of plant extracts as therapeutic components.

BACKGROUND OF THE INVENTION

It is generally accepted that hormonal replacement therapy in postmenopausal women, besides many beneficial therapeutical effects, increases the risk of breast or endometrial cancer, at least after a prolonged treatment (1).

If all responses to estrogen were mediated by the same mechanism and all ERs were identical, as it was first reported for the cytosol-nuclear receptor-mediated genomic responses (2), the possibility to selectively induce therapeutically convenient responses to estrogen, but not those at risk (cell proliferation), would be scarce.

The finding in our Laboratory of the first non-genomic mechanism of estrogen action in the uterus and its investigation in depth for more than 30 years (3-11), revealed the existence of multiple kinds of estrogen receptors, involved in various independent groups of responses to estrogen stimulation through separate mechanisms of hormone action (4, 8, 9, 11-14). Among them, cytoplasmic membrane hormone receptors (15, 16), type II estrogen cytoplasmic and nuclear receptors (17) and specific antiestrogen receptors (18); more recently, immunochemical (19) and ligand (20) differences between two kind of the classical "cytosol-nuclear receptors" were reported; these receptors were named $\alpha$ and $\beta$ ERs (21). The differences between receptors and the mechanisms of estrogen action involved, and the independence between the various groups of responses to hormone stimulation, allow the dissociation of responses to estrogens into separate groups, which can be selectively stimulated, inhibited or completely blocked.

Several agents or conditions were already reported to dissociate the various estrogenic responses in same animal. Among them, the route of estrogen administration allowing physiological hormone levels locally or systemically (22), the use of different estrogenic compounds, such as estriol (23), estradiol-17$\alpha$ (11), diethylstilbestrol (14), clomiphene (24), nafoxidine (12, 25), 2(OH)-estradiol-17$\beta$ or 4(OH)estradiol-17$\beta$ (26); the interaction with other hormones such as glucocorticoids (27), progesterone (28), insulin (29) or thyroid hormones (30); the administration of various pharmaceuticals or biological reagents such as theophylline (31), bromocriptine (32); actinomycin D (33) or colloidal carbon (13), and the exposure to environmental pollutants such as lead (34) or DDT (35). This dissociation opens a new therapeutic approach, to selectively induce desired responses of estrogen stimulation, without the simultaneous induction of responses considered at risk (endometrial or mammary cell proliferation).

There are several reports indicating lower incidence of breast cancer in Asian women than in Western women (36); this difference in breast cancer incidence parallels the significantly higher amount of phytoestrogens—including soybean products—consumed by Asian women (36). Second- and third-generation descendants of women who migrated from Asia to Western countries have breast cancer risks similar to those of women in the host country, suggesting that lifestyle and not genetic factors explain the low breast cancer risk observed in Asian women (37, 38). In East and Southeast Asia the average intake of phytoestrogens is estimated to be more than ten times higher than in the United States or Europe (39), and plasma isoflavone concentrations are much higher in Japanese women than in Europeans, suggesting their role in breast cancer prevention (40).

Taking into consideration epidemiologic evidence suggesting that Oriental countries preferential diet containing soy products—rich in glucosides of estrogenic isoflavones such as genistein (41), may protect against breast cancer development (40, 42-44), our research interest was turned to investigate whether these compounds are able to selectively induce some but not all responses to hormone stimulation in the uterus, for their potential use as therapeutic agents for hormonal replacement therapy devoid of neoplastic risk. For this purpose, we initially investigated the in vivo estrogenic agonistic effects of chemically pure genistein and of phytoestrogens present in soybean extracts on various parameters of estrogen action in the rat uterus, and the in vitro cell proliferation of two mammary cancer cell lines in tissue culture.

For further background to this disclosure is the fact that ancestral populations used, for centuries, several native plant species for specific health needs such as menstrual pain, menstrual cycle normalization, dysmenorrheal and other disorders. According to ethno/medicinal knowledge there are numerous plant species useful for treatment of several "diseases" which actually are clinical symptoms. Several compounds have been identified in many of these plant species, but there is no knowledge about which of these compounds are involved in the therapeutic effects indigenous population claim to exist. Further, there is no scientific demonstration of the effectiveness of the therapeutic effects nor is there knowledge on the molecular mechanisms involved.

Subsequently, we incorporated into the study extracts and decoctions of various plant species, chosen according to ethno-medicinal knowledge that they displayed any gynecologic or sex hormone activity or interfered with reproductive physiology.

SUMMARY OF THE INVENTION

The present disclosure describes estrogenic activity present in various plant species, selectively inducing some but not all estrogenic responses in the uterus. Prepubertal female rats were treated sequentially with various extracts or decoctions of different plant species or its vehicle, followed 1 h later by treatment with estradiol-17$\beta$ (E) or its solvent. Uteri were excised under anesthesia and histologically processed for eosinophil quantification and morphometric evaluation of various uterine responses to estrogen, at 6 or 24 h after hormone or vehicle treatment. Besides extracts or decoctions, pure phytoestrogens were also used. Additionally, human mammary cancer cells MCF-7 or MDAMB-231 were cultured in presence of the extract (or decoction), E, both or solvent and cell proliferation was evaluated. Various extracts or decoction displayed selective estrogenic and/or antiestrogenic action for some but not all parameters of estrogen stimulation in the uterus and inhibited growth of human mammary cells in culture or antagonized the estrogen-induced increase in their growth. This disclosure reveals, for the first time, a dissociation of responses to estrogen by phytoestrogens, suggesting its possible therapeutic application as estrogenic compounds not inducing cell proliferation. Furthermore, this disclosure reveals the anticancerous effect of some of the extracts with possible therapeutic relevance.

SHORT DESCRIPTION OF THE FIGURES

FIG. 1. Effect of a treatment with estradiol-17β, or phytoestrogens on myometrial cell hypertrophy. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate means (expressed as % of response to estradiol)±standard error of the mean. Statistics: least significant difference a posteriori LSD test. , $p<0.01$; ** or ++++, $p<0.0001$; *, comparisons to vehicle-treated controls; +, comparisons to estradiol-treated animals.

Figure 2:
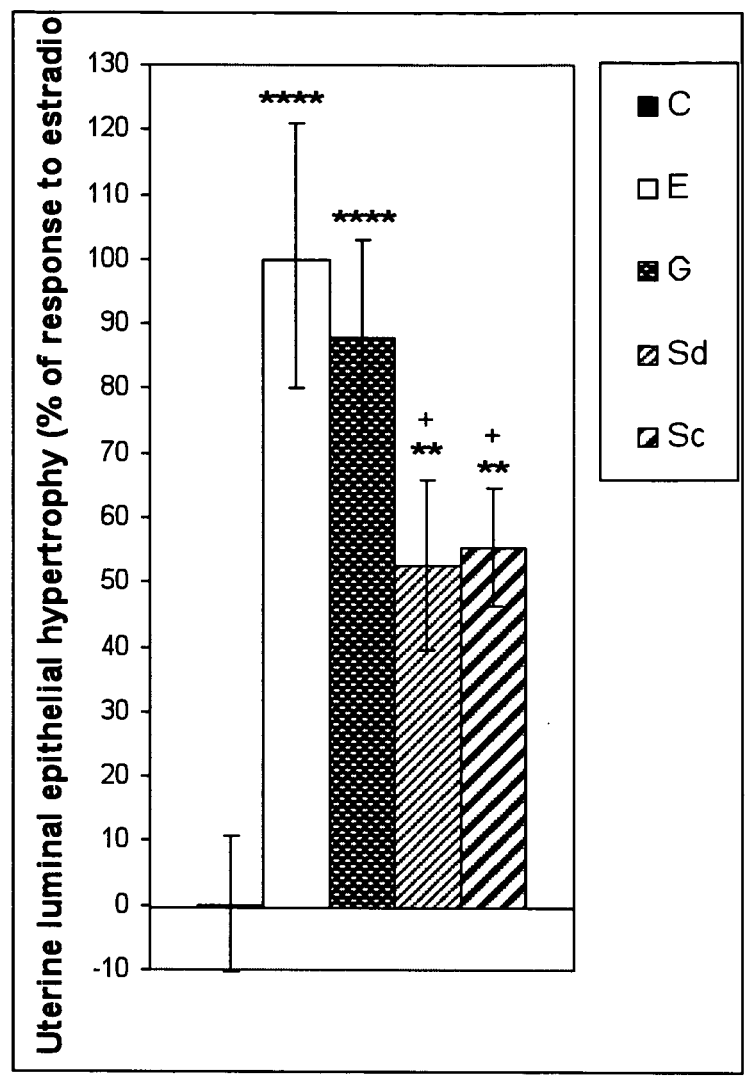

FIG. 2. Effect of a treatment with estradiol-17β, or phytoestrogens on endometrial luminal epithelial cell hypertrophy. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate geometric means from log-transformed data (expressed as % of response to estradiol)±standard error of the mean. Statistics: least significant difference a posteriori LSD test. +, $p<0.05$; , $p<0.01$; **, $p<0.0001$; *, comparisons to vehicle-treated controls; +, comparisons to estradiol-treated animals.

Figure 3:
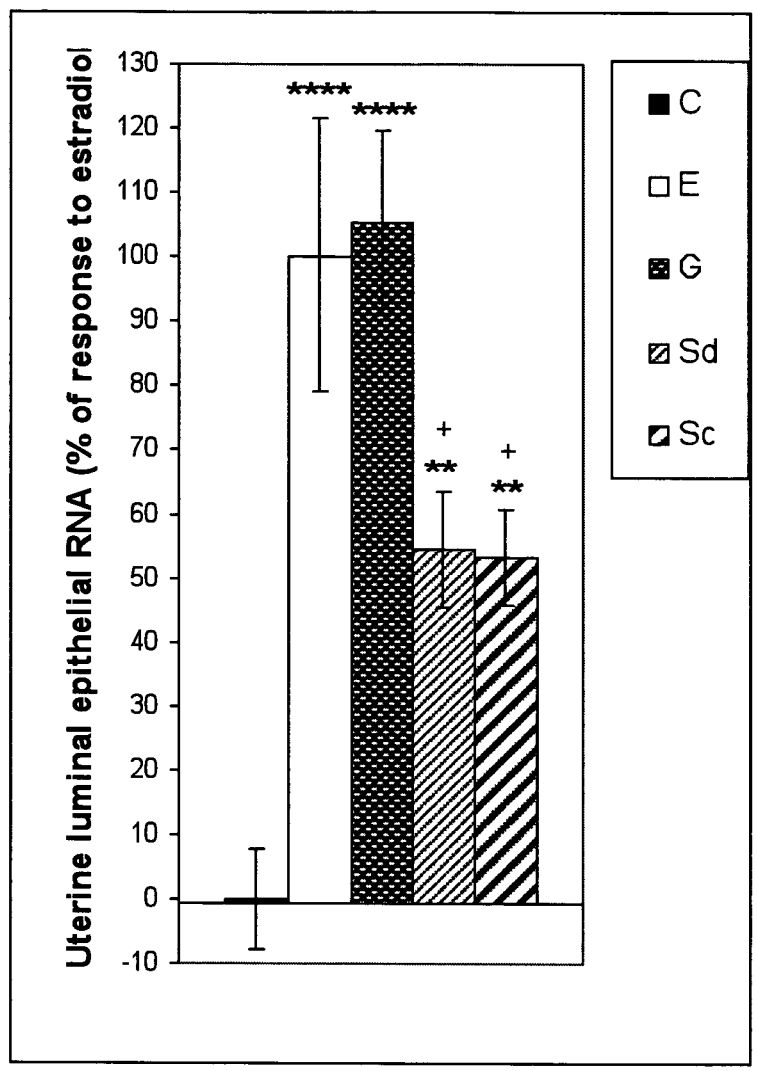

FIG. 3. Effect of a treatment with estradiol-17β or phytoestrogens on endometrial luminal epithelial cell RNA content. Prepubertal rats received s.c. 0.33 mg estradiol-17β/kg b.wt (E), 0.5 mg genistein/kg b.wt. (G), soybean extract containing 0.06 mg genistin/kg b.wt. (Sd) or 0.364 mg genistin/kg b.wt. (Sc), or vehicle (C), and the uteri were excised 24 h thereafter under anesthesia. Bars indicate geometric means from log-transformed data (expressed as % of response to estradiol)±standard error of the mean. Statistics: least significant difference a posteriori LSD test. +, $p<0.05$; , $p<0.01$; **, $p<0.0001$; *, comparisons to vehicle-treated controls; +, comparisons to estradiol-treated animals FIG. 4. Effect of a treatment with estradiol-17β or phytoestrogens on edema in deep endometrial stroma. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 6 h thereafter under anesthesia. Bars indicate means (expressed as % of response to estradiol)±standard error of the mean. Statistics: least significant difference a posteriori LSD test. **** or ++++, $p<0.0001$; *, comparisons to vehicle-treated controls; +, comparisons to estradiol-treated animals.

Figure 5:
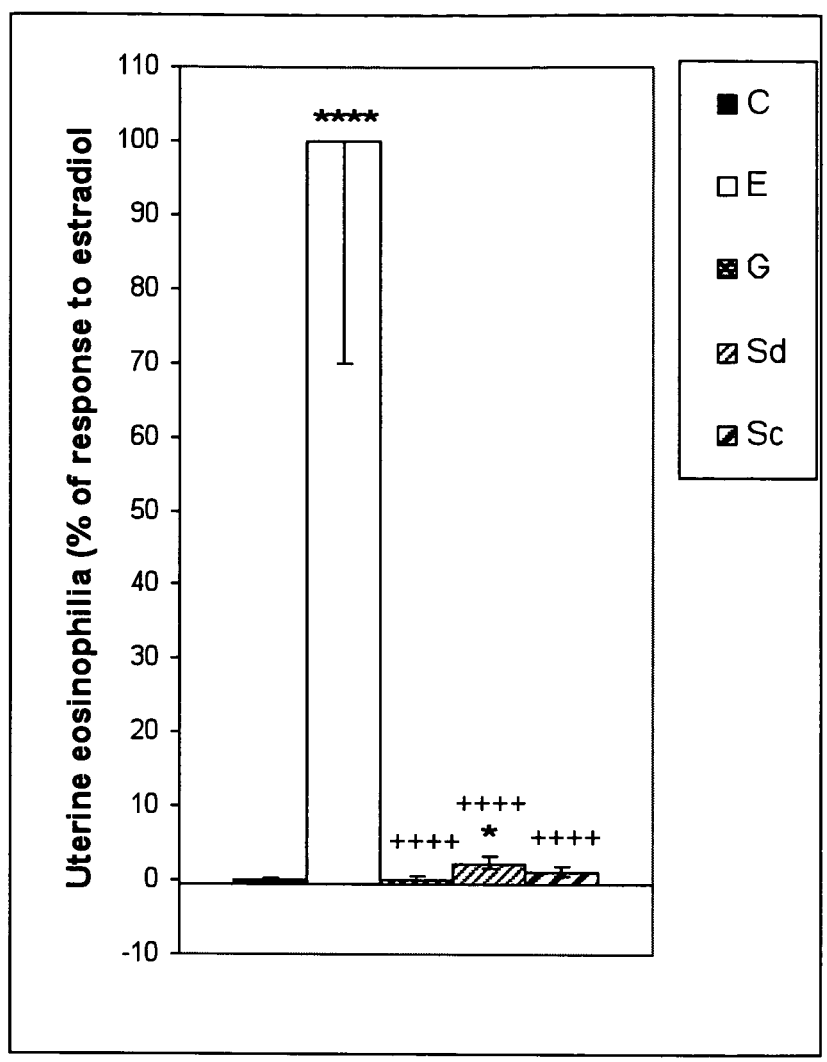

FIG. 5. Effect of a treatment with estradiol-17β or phytoestrogens on uterine eosinophilia. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 6 h thereafter under anesthesia. Bars indicate geometric means from log-transformed data (expressed as % of response to estradiol)±standard error of the mean. Statistics: least significant difference a posteriori LSD test. *, $p<0.05$; **** or ++++, $p<0.0001$; *, comparisons to vehicle-treated controls; +, comparisons to estradiol-treated animals.

Figure 6:
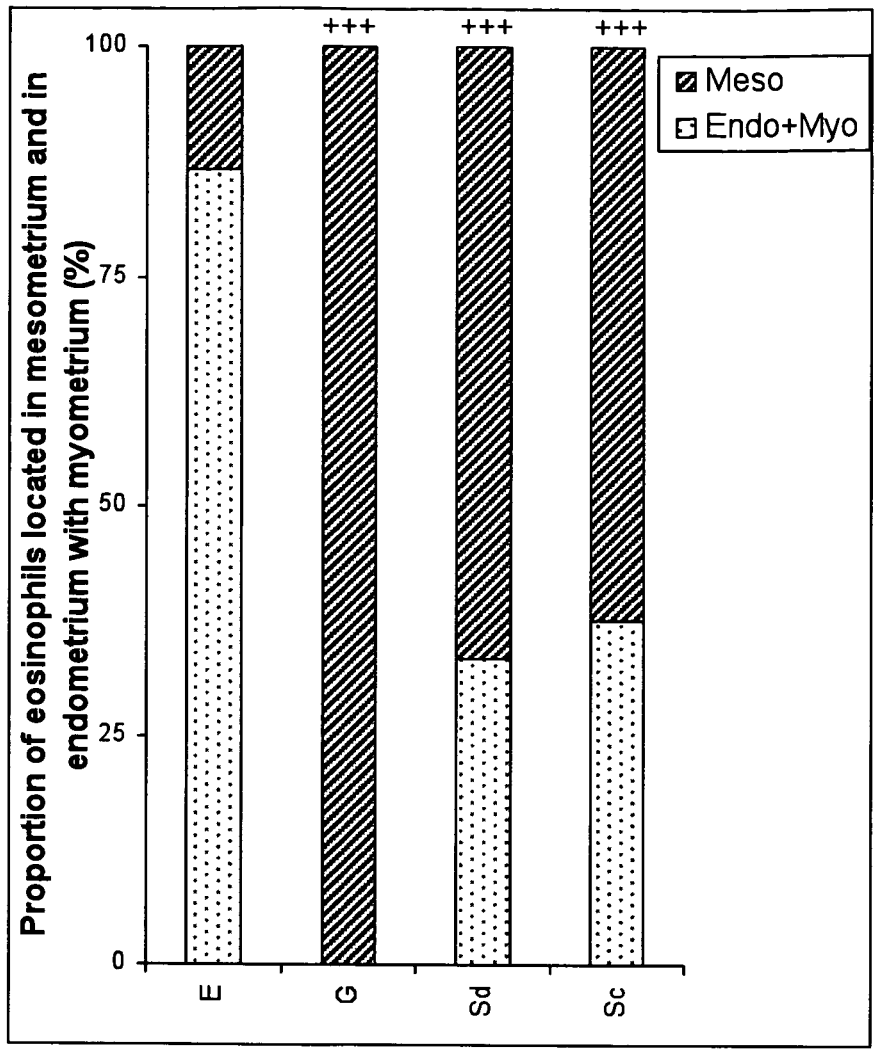

FIG. 6. Effect of a treatment with estradiol-17β or phytoestrogens on the proportion of uterine eosinophils located in the mesometrium and in the endometrium with myometrium. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 6 h thereafter under anesthesia. The proportion in controls is not shown because of the extremely low eosinophil numbers, that does not allow any statistical analysis. Statistics: $\chi^2$ test; +++, $p<0.001$; comparisons to estradiol-treated animals.

Figure 7:
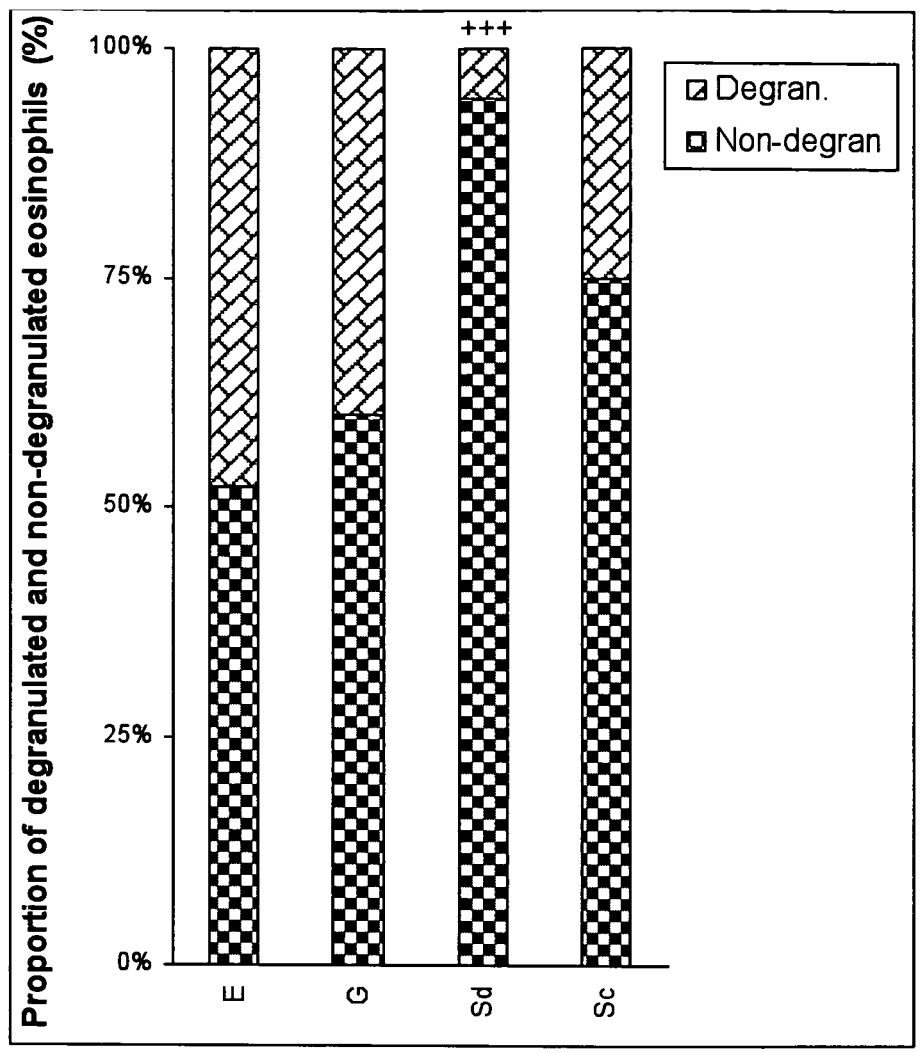

FIG. 7. Effect of a treatment with estradiol-17β or phytoestrogens on the proportion of uterine degranulated and non-degranulated eosinophils. Prepubertal rats received s.c. 0.33 mg estradiol-17β/kg b.wt (E), 0.5 mg genistein/kg b.wt. (G), soybean extract containing 0.06 mg genistin/kg b.wt. (Sd) or 0.364 mg genistin/kg b.wt. (Sc), or vehicle (C), and the uteri were excised 6 h thereafter under anesthesia. The proportion in controls is not shown because of the extremely low eosinophil numbers, that does not allow any statistical analysis. Statistics: $\chi^2$ test; +++, $p<0.001$; comparisons to estradiol-treated animals.

Figure 8:
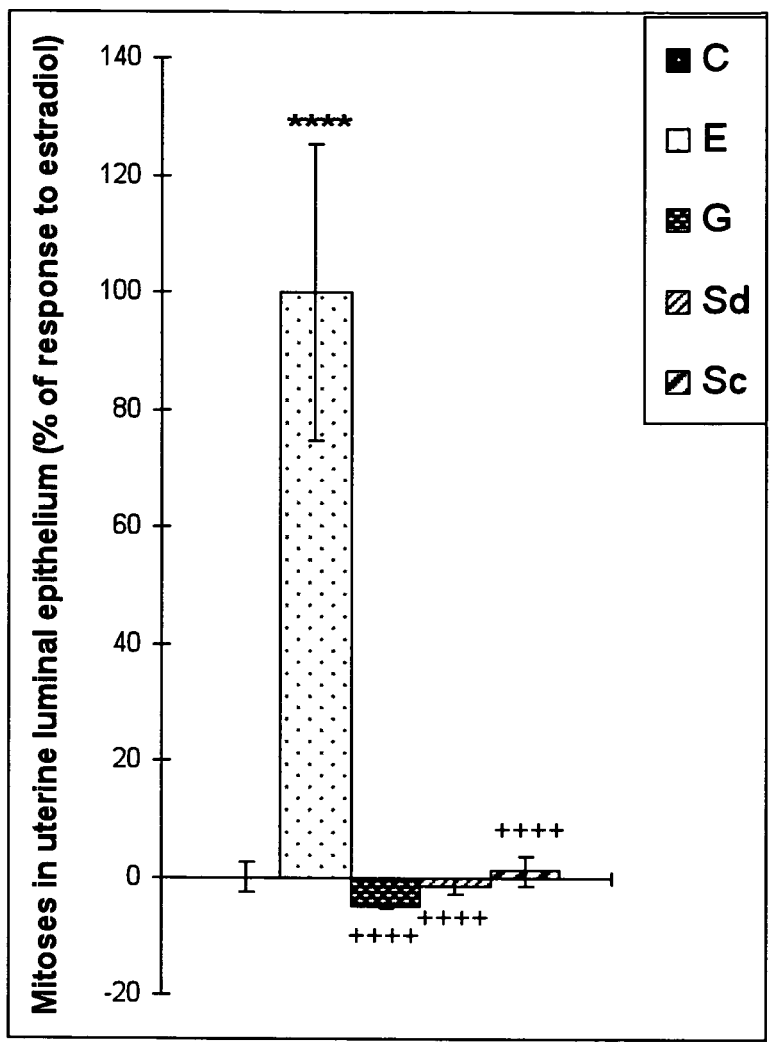

FIG. 8. Effect of a treatment with estradiol-17β or phytoestrogens on the number of mitotic figures in uterine luminal epithelium. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate means (expressed as % of response to estradiol)±standard error of the mean. Statistics: least significant difference a posteriori LSD test. **** or ++++, $p<0.0001$; *, comparisons to vehicle-treated controls; +, comparisons to estradiol-treated animals.

Figure 9:
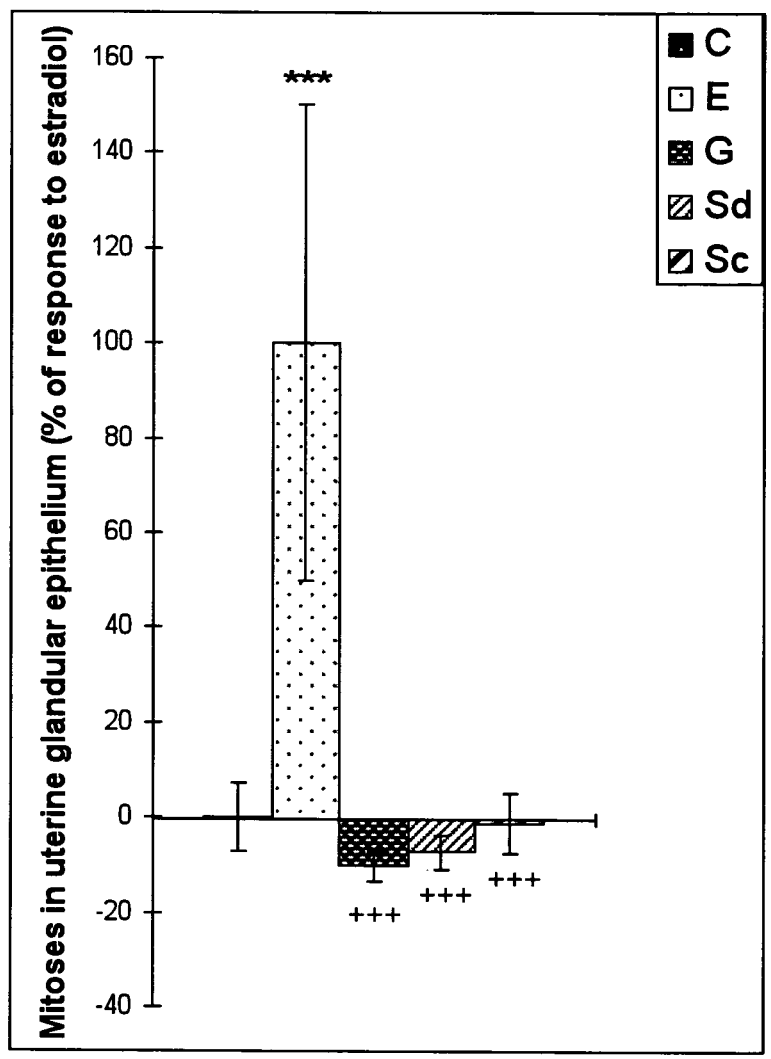

FIG. 9. Effect of a treatment with estradiol-17β or phytoestrogens on the number of mitotic figures in uterine glandular epithelium. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate means (expressed as % of response to estradiol)±standard error of the mean. Statistics: least significant difference a posteriori LSD test. *** or +++, $p<0.001$; *, comparisons to vehicle-treated controls; +, comparisons to estradiol-treated animals.

Figure 10:
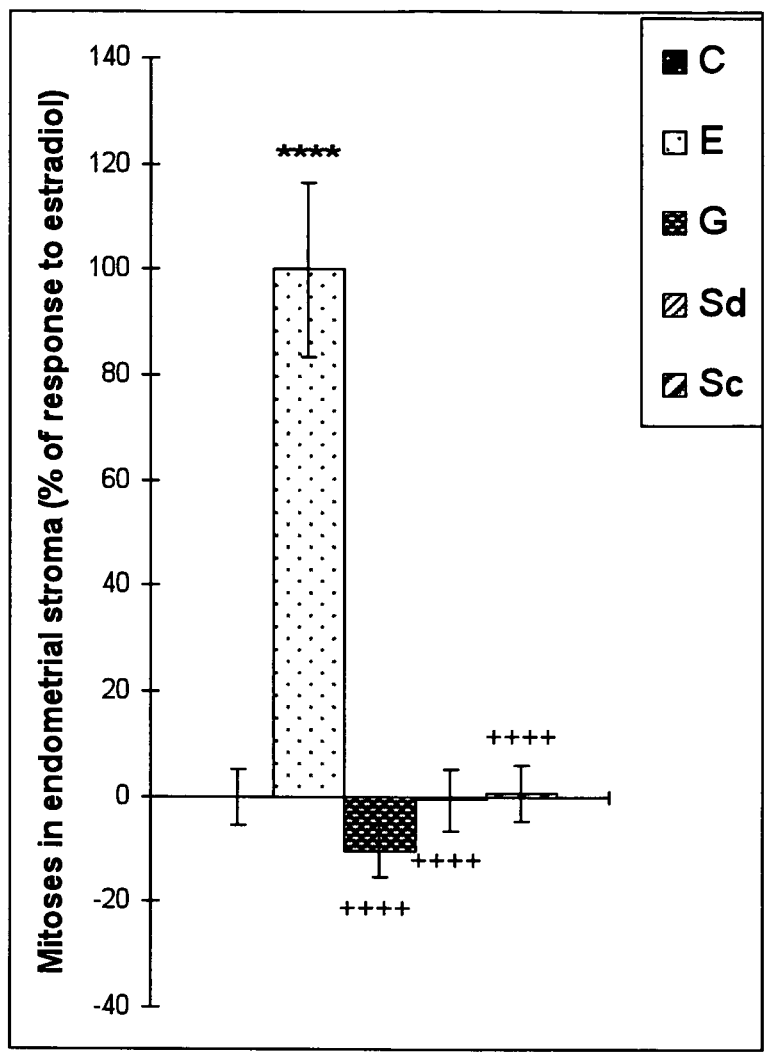

FIG. 10. Effect of a treatment with estradiol-17β or phytoestrogens on the number of mitotic figures in uterine endometrial stroma. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate means (expressed as % of response to estradiol)±standard error of the mean. Statistics: least significant difference a posteriori LSD test. **** or ++++, $p<0.0001$; *, comparisons to vehicle-treated controls; +, comparisons to estradiol-treated animals.

Figure 11:
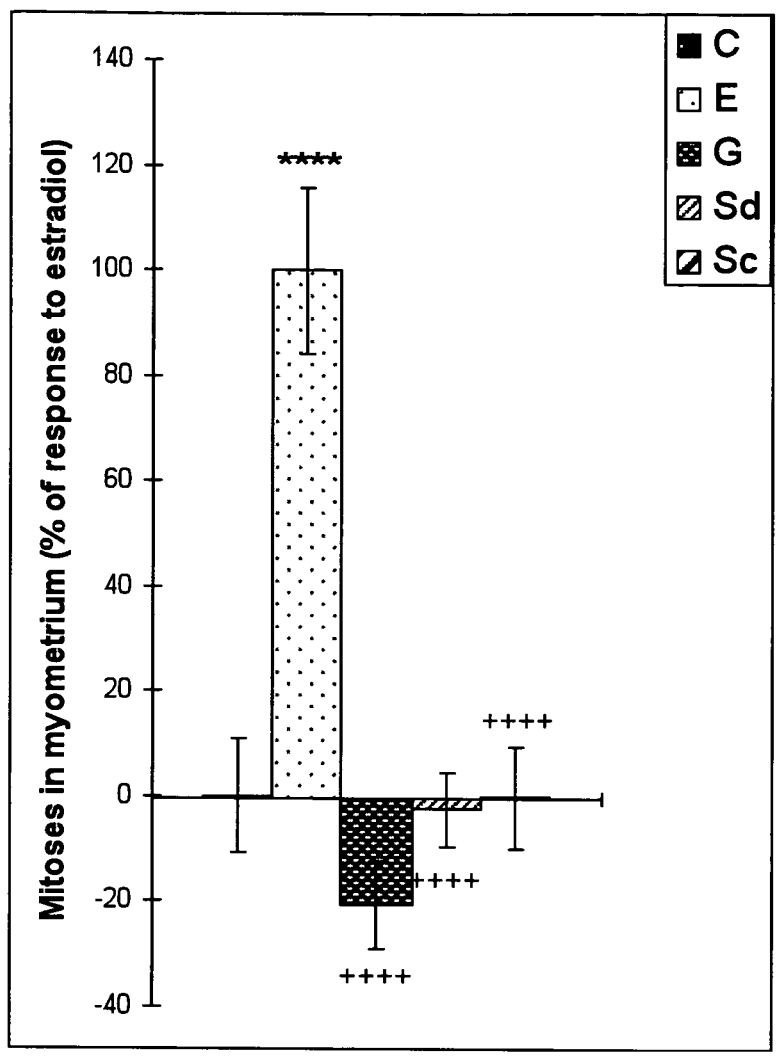

FIG. 11. Effect of a treatment with estradiol-17β or phytoestrogens on the number of mitotic figures in myometrium. Prepubertal rats received s.c. 0.33 mg estradiol-17β/kg b.wt (E), 0.5 mg genistein/kg b.wt. (G), soybean extract containing 0.06 mg genistin/kg b.wt.(Sd) or 0.364 mg genistin/kg b.wt. (Sc), or vehicle (C), and the uteri were excised 24 h thereafter under anesthesia. Bars indicate means (expressed as % of response to estradiol)±standard error of the mean. Statistics: least significant difference a posteriori LSD test. **** or ++++, p<0.0001; *, comparisons to vehicle-treated controls; +, comparisons to estradiol-treated animals.

Figure 12:
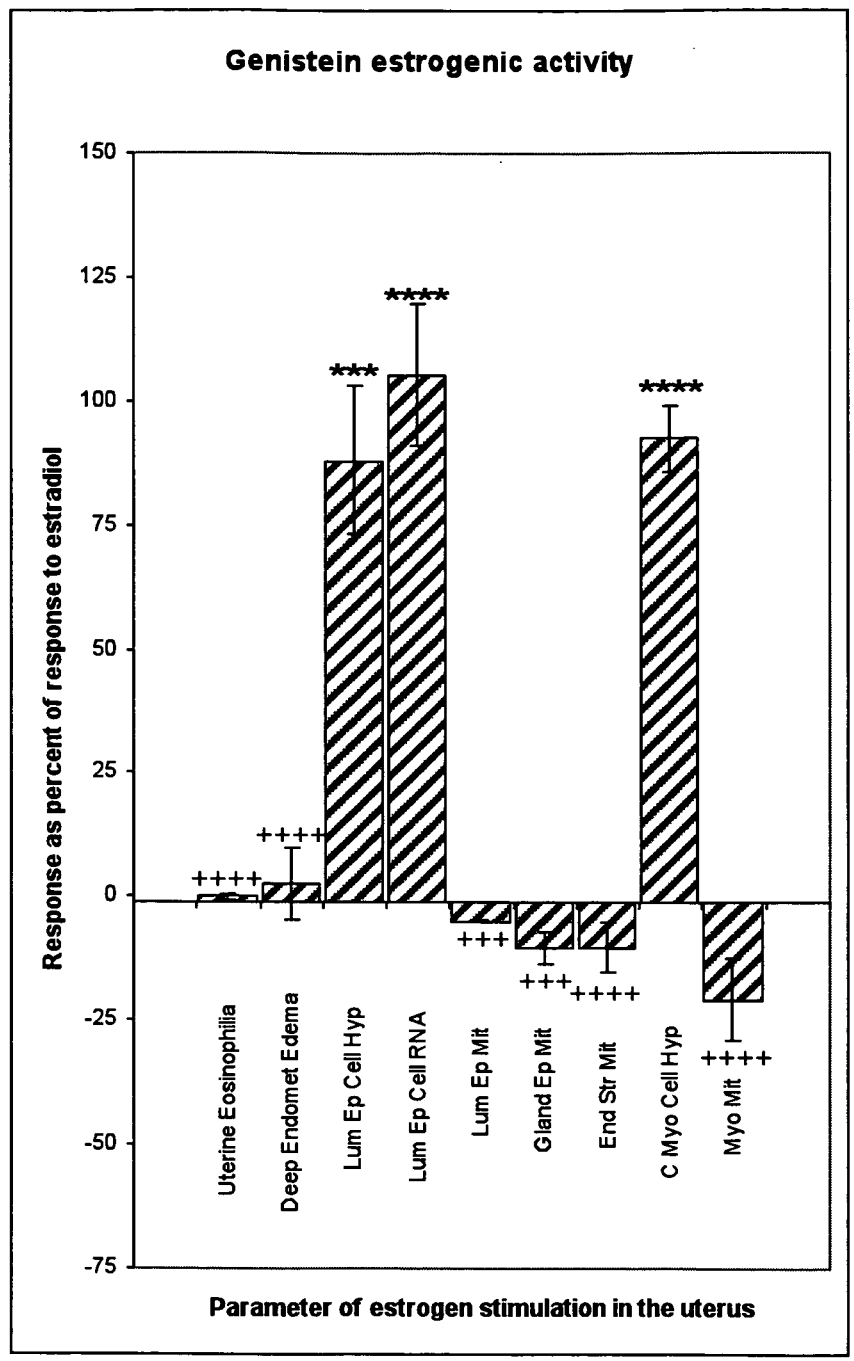

FIG. 12. Comparison of the estrogenic activity of estradiol to that of genistein (expressed as % of the activity of estradiol) for the various parameters of estrogen action in the uterus. Prepubertal rats received s.c. 0.33 mg estradiol-17β/kg b.wt (E), 0.5 mg genistein/kg b.wt. (G), soybean extract containing 0.06 mg genistein/kg b.wt. (Sd) or 0.364 mg genistin/kg b.wt. (Sc), or vehicle (C), and the uteri were excised 6 or 24 h after treatment (vide supra). Bars indicate means (expressed as % of response to estradiol)±standard error of the mean. Statistics: least significant difference a posteriori LSD test. * or +++, p<0.001; ** or ++++, p<0.0001; *, comparisons to vehicle-treated controls; +, comparisons to estradiol-treated animals.

Figure 13:
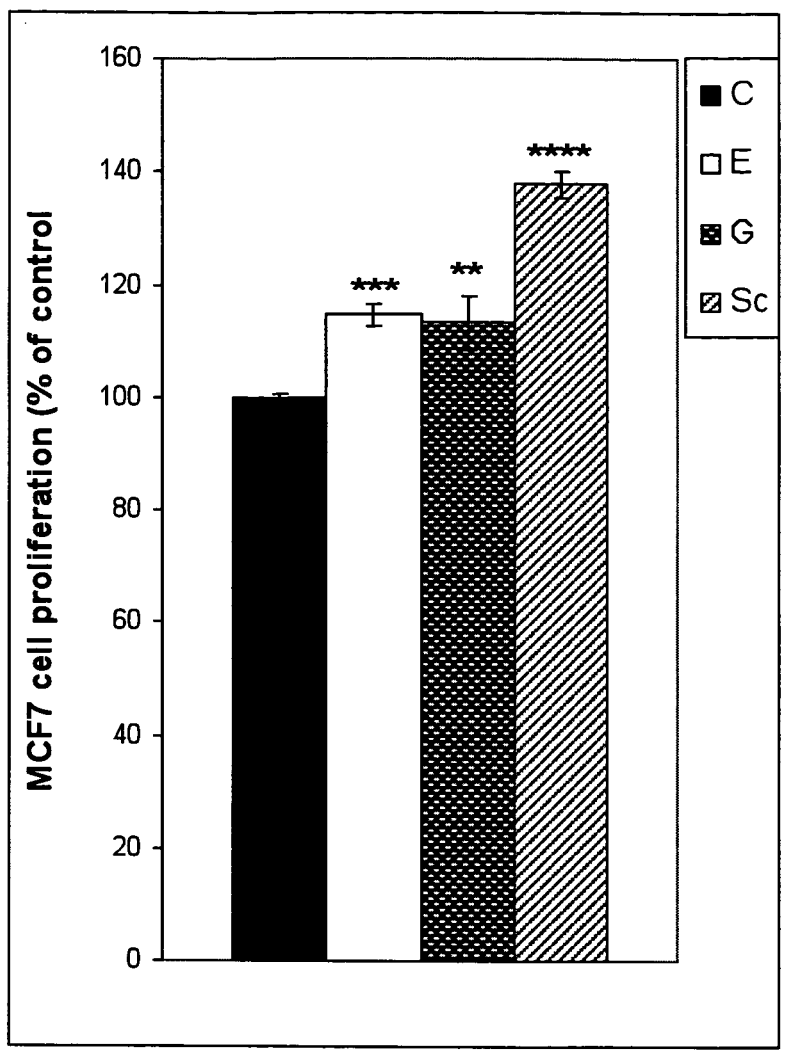

FIG. 13. Effect of estradiol-17β or phytoestrogens on cell proliferation of cultured human MCF-7 mammary cancer cells. Estradiol (E), Genistein (G), concentrated soybean extract containing 0.364 mg genistin/kg b.wt. (Sc) or vehicle (C) was added to the culture media and number of cells was evaluated 72 h later. Bars indicate means (expressed as % of values in controls)±standard error of the mean. Statistics: least significant difference a posteriori LSD test. , p<0.01; *, p<0.001; **, p<0.0001; comparisons to vehicle-treated controls FIG. 14. Effect of estradiol-17β or phytoestrogens on cell proliferation of cultured human MDAMB-231 mammary cancer cells. Estradiol (E), Genistein (G), concentrated soybean extract containing 0.364 mg genistin/kg b.wt. (Sc) or vehicle (C) was added to the culture media and number of cells was evaluated 72 h later. Bars indicate means (expressed as % of values in controls)±standard error of the mean. Statistics: least significant difference a posteriori LSD test. , p<0.01; *, p<0.001; **, p<0.0001; comparisons to vehicle-treated controls.

Figure 15:
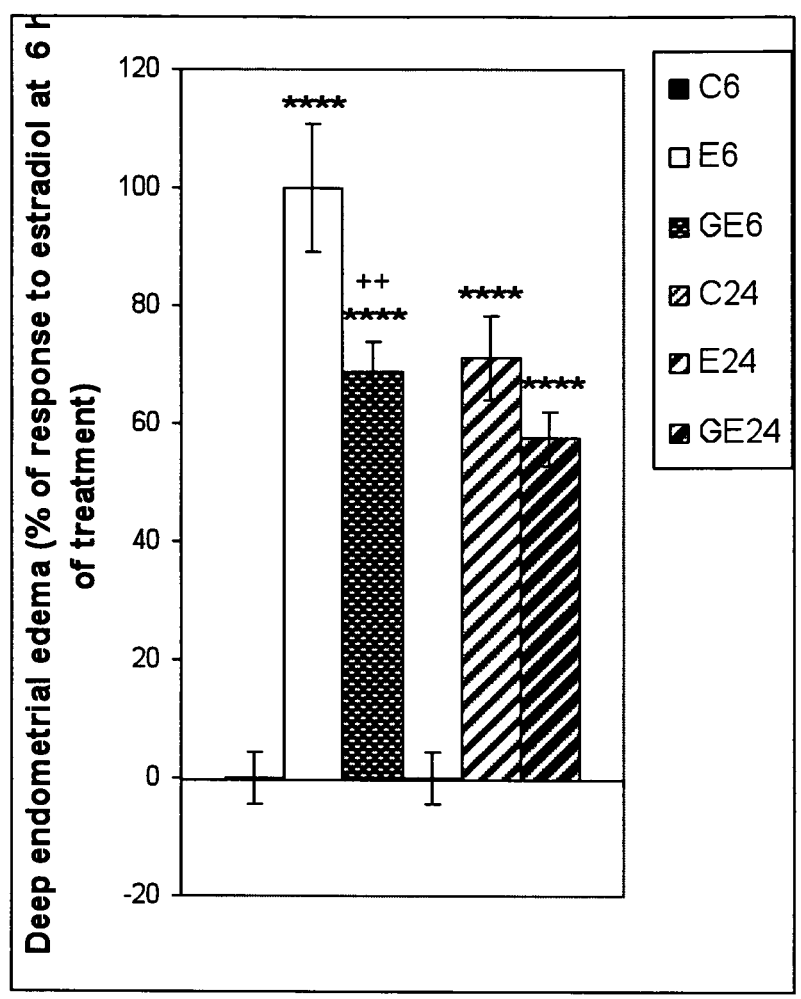

FIG. 15. Genistein-induced antagonism on deep endometrial stromal edema induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 6 h after hormone treatment.)±standard error of the mean. Statistics: Least significant difference a posteriori test (LSD), ****p<0.0001, compared to the homologous condition without E treatment; ++p<0.01, compared to the homologous condition without pretreatment with genistein.

Figure 16:
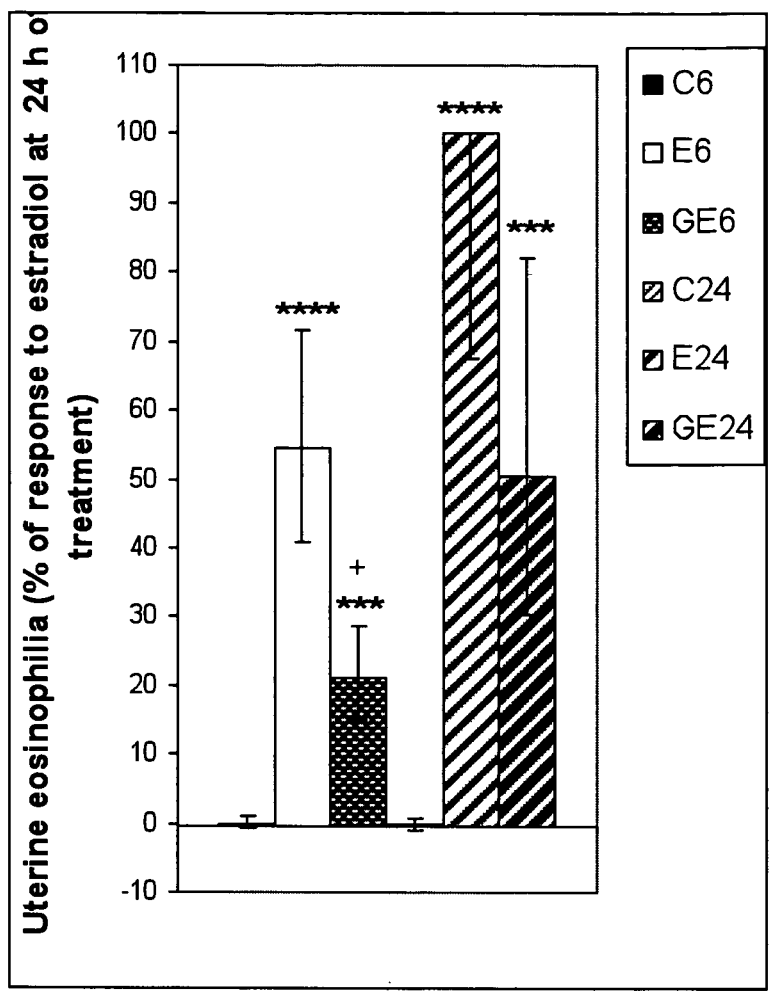

FIG. 16. Genistein-induced antagonism on uterine eosinophilia induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 24 h after hormone treatment.)±standard error of the mean. Statistics: Least significant difference a posteriori test (LSD), *p<0.001, **p<0.0001, compared to the homologous condition without E treatment; +p<0.05, compared to the homologous condition without pretreatment with genistein.

Figure 17:
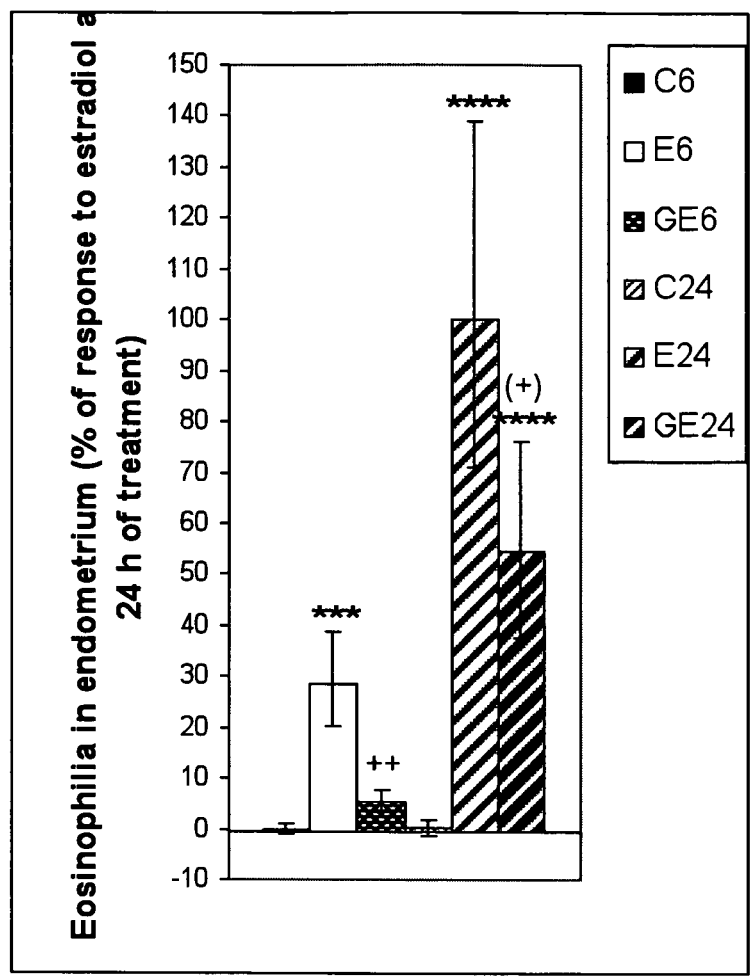

FIG. 17. Genistein-induced antagonism on endometrial eosinophilia induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 24 h after hormone treatment.)±standard error of the mean. Statistics: Least significant difference a posteriori test (LSD), *p<0.001, **p<0.0001, compared to the homologous condition without E treatment; (+)0.05<p<0.10, ++p<0.01 compared to the homologous condition without pretreatment with genistein.

Figure 18:
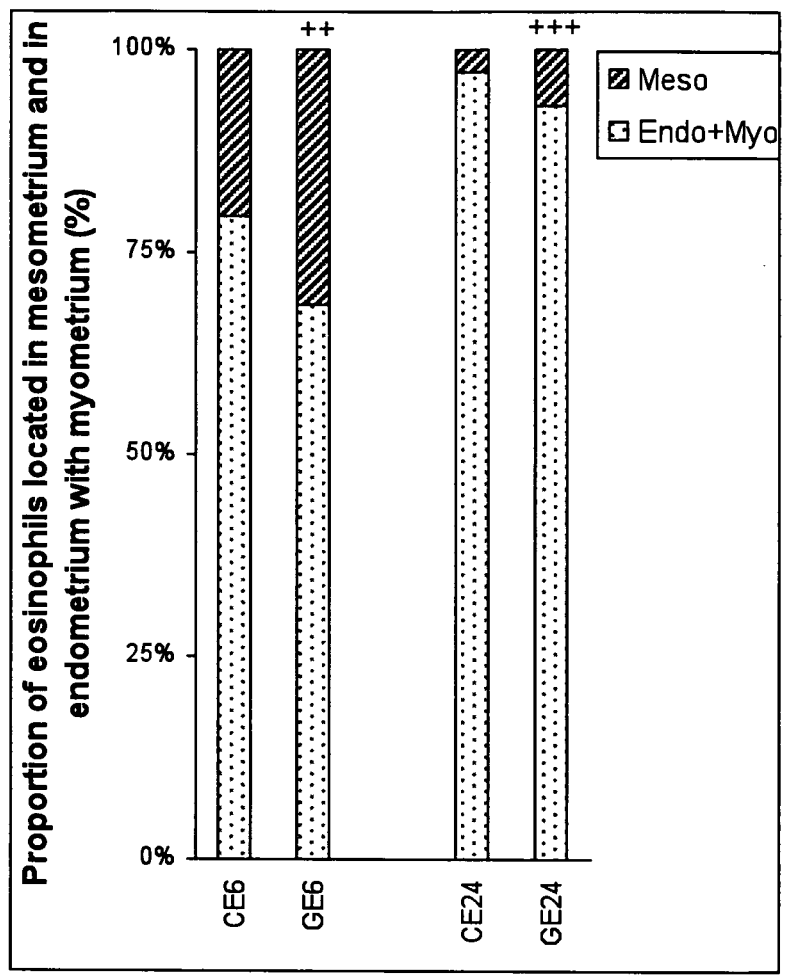

FIG. 18. Effect of genistein and estradiol-17β on the proportion of uterine eosinophils located in the mesometrium and in the endometrium with myometrium. Prepubertal rats received s.c. 0.33 mg estradiol-17β/kg b.wt (E), or 0.5 mg genistein/kg b.wt. followed by estradiol (GE), or vehicle (C), and the uteri were excised 6 h or 24 h thereafter under anesthesia. The proportion in controls is not shown because of the extremely low eosinophil numbers, that does not allow any statistical analysis. Statistics: $\chi^2$ test; ++, p<0.01, +++, p<0.001; comparisons to animals treated with estradiol alone.

Figure 19:
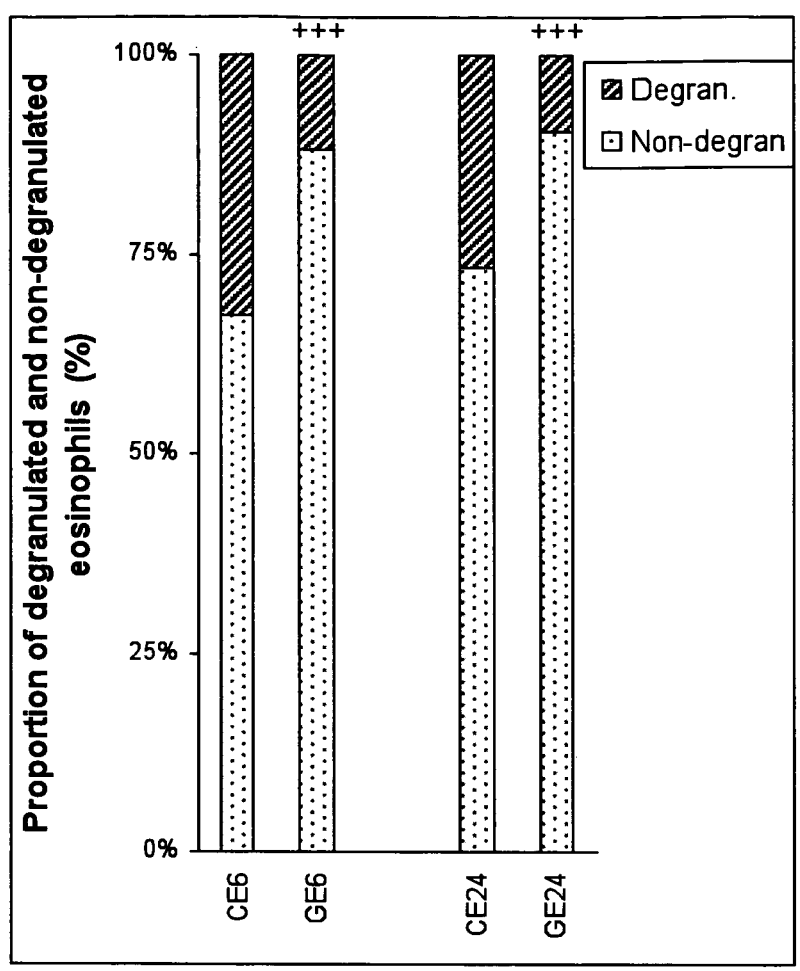

FIG. 19. Effect of genistein and estradiol-17β on the proportion of degranulated and non-degranulated uterine eosinophils. Prepubertal rats received s.c. 0.33 mg estradiol-17β/kg b.wt (E), or 0.5 mg genistein/kg b.wt. followed by estradiol (GE), or vehicle (C), and the uteri were excised 6 h or 24 h thereafter under anesthesia. The proportion in controls is not shown because of the extremely low eosinophil numbers, that does not allow any statistical analysis. Statistics: $\chi^2$ test, +++, p<0.001; comparisons to animals treated with estradiol alone.

Figure 20:
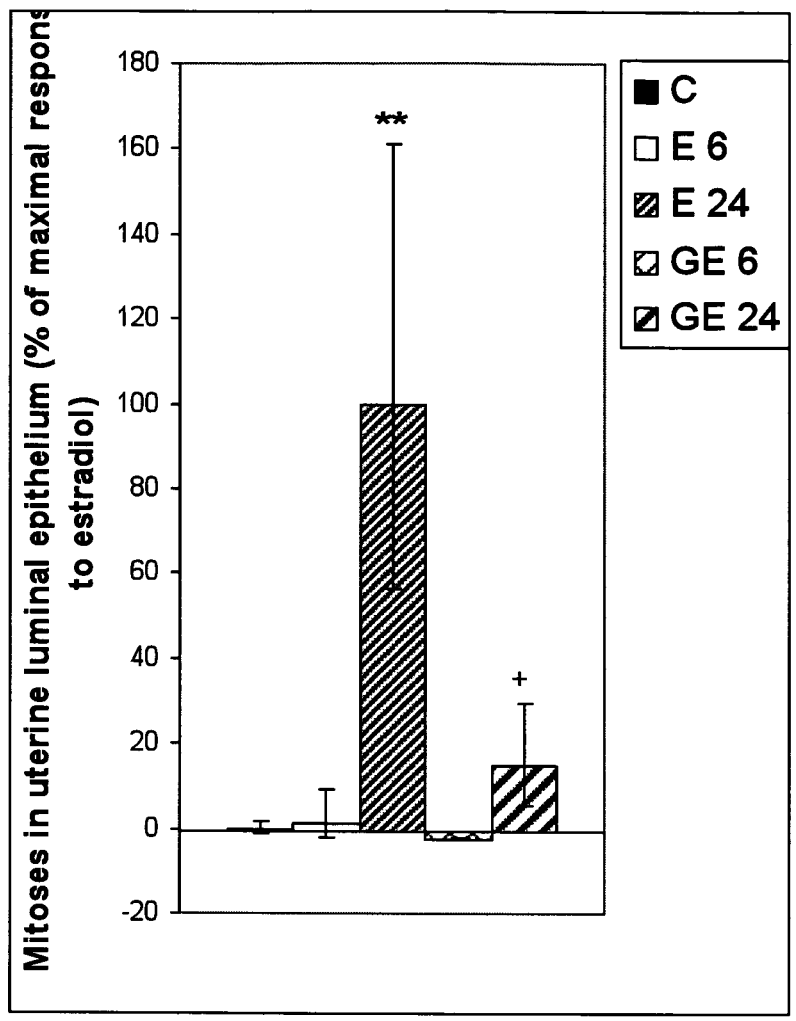

FIG. 20. Genistein-induced antagonism on the proliferation of uterine luminal epithelial cells induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 24 h after hormone treatment.)±standard error of the mean. Statistics: Least significant difference a posteriori test (LSD), **p<0.01, compared to the homologous condition without E treatment; +p<0.05, compared to the homologous condition without pretreatment with genistein.

Figure 21:
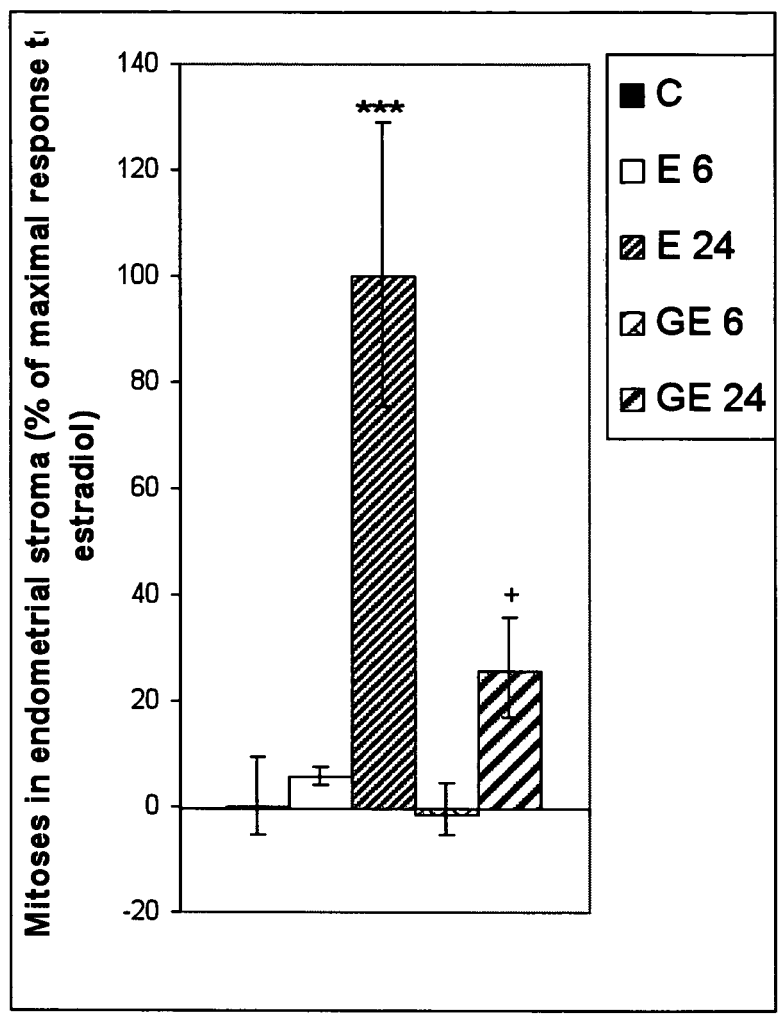

FIG. 21. Genistein-induced antagonism on the proliferation of endometrial stromal cells induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 24 h after hormone treatment.)±standard error of the mean. Statistics: Least significant difference a posteriori test (LSD), ***p<0.001, compared to the homologous condition without E treatment; +p<0.05, compared to the homologous condition without pretreatment with genistein.

Figure 22:
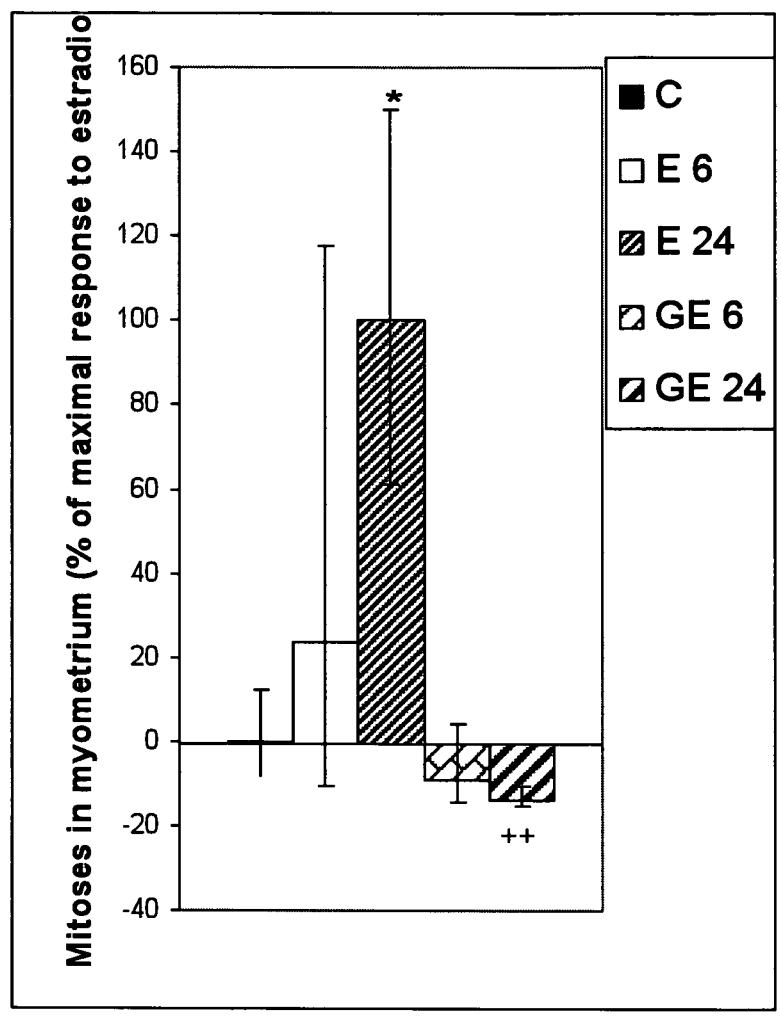

FIG. 22. Genistein-induced antagonism on the proliferation of myometrial cells induced by estradiol-17β. Prepubertal rats received s.c. 0.33 mg estradiol-17β/kg b.wt (E) or 0.5 mg genistein/kg b.wt., followed by estradiol 1 h later (GE). The controls (C) received the vehicle. The uteri were excised 6 h (E6, GE6) or 24 h (E24, GE24) after estradiol treatment, under anesthesia. Bars indicate means (expressed as % of response to estradiol at 24 h after hormone treatment.)±standard error of the mean. Statistics: Least significant difference a posteriori test (LSD), *p<0.05, compared to the homologous condition without E treatment; ++p<0.01, compared to the homologous condition without pretreatment with genistein.

Figure 23:
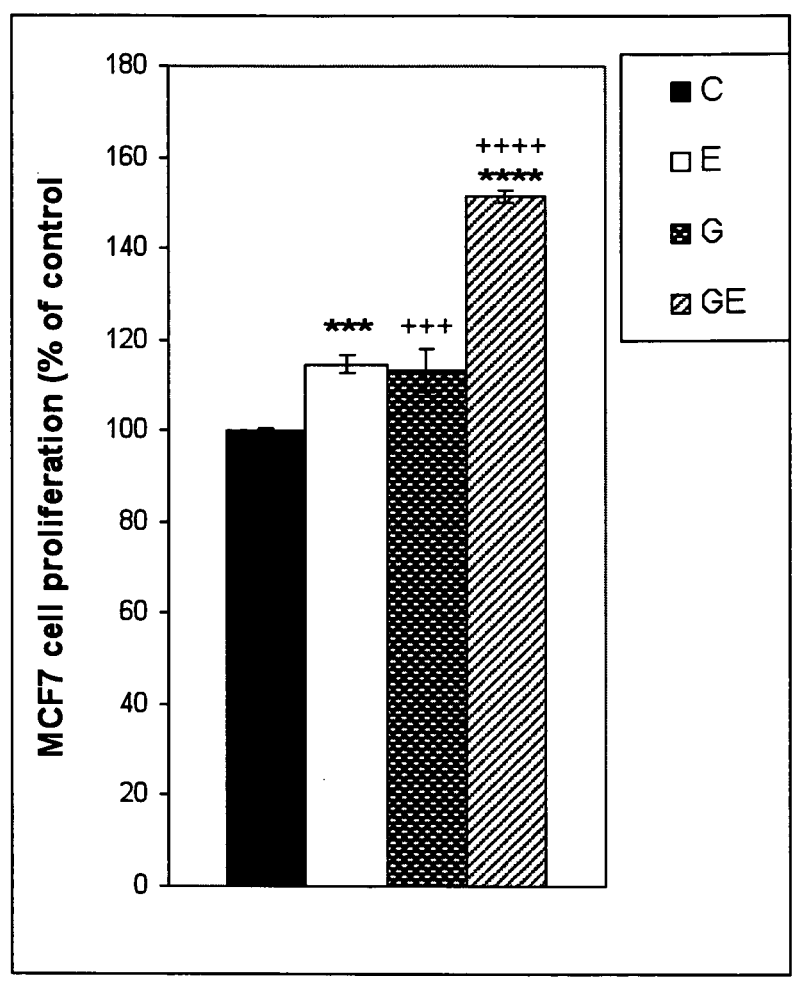

FIG. 23. Effect of genistein, estradiol-17β or both on cell proliferation of cultured human MCF-7 mammary cancer cells. Estradiol (E), genistein (G), genistein plus estradiol (GE) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.001$, $p<0.0001$, compared to the homologous condition without E treatment; +++$p>0.001$, ++++$p<0.0001$, compared to the homologous condition without pretreatment with genistein FIG. 24. Effect of genistein, estradiol-17β or both on cell proliferation of cultured human MDAMB-231 mammary cancer cells. Estradiol (E), genistein (G), genistein plus estradiol (GE) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.001$, ****$p<0.0001$, compared to the homologous condition without E treatment; ++++$p<0.0001$, compared to the homologous condition without pretreatment with genistein.

Figure 25:
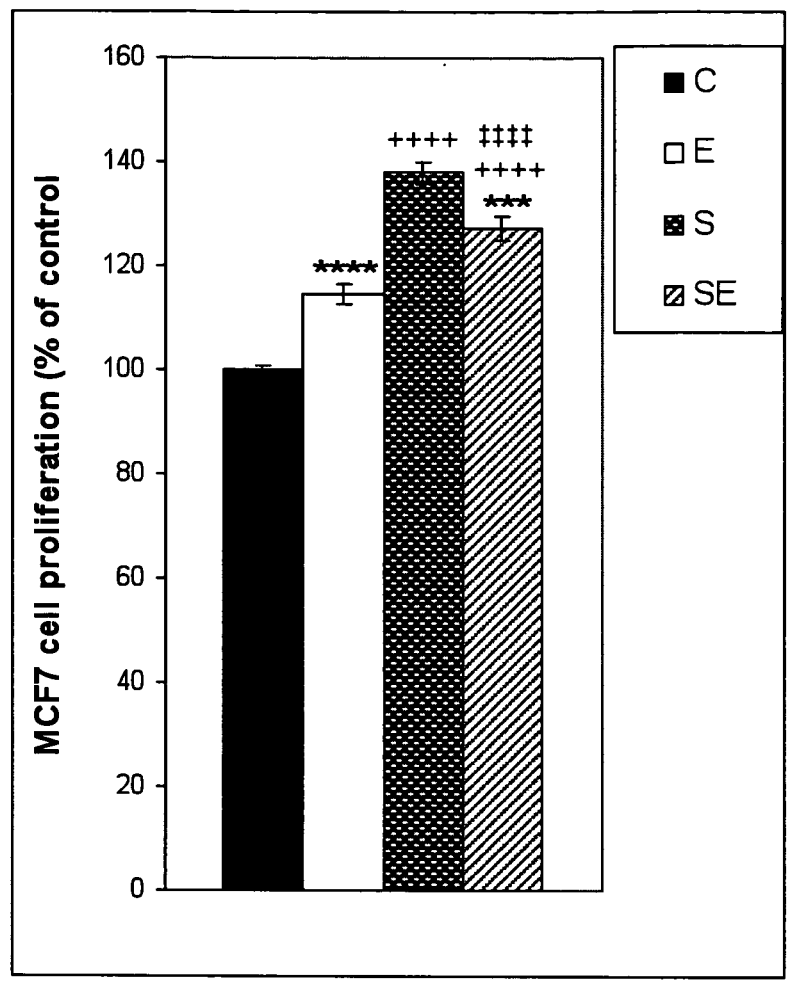

FIG. 25. Effect of soy extract, estradiol-17β or both on cell proliferation of cultured human MCF-7 mammary cancer cells. Estradiol (E), soy extract (S), soy extract plus estradiol (SE) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.001$, **$p<0.0001$, compared to the homologous condition without E treatment, ++++$p<0.0001$, compared to the homologous condition without pretreatment with genistein; ‡‡‡‡$p<0.0001$, compared to controls without any treatment.

Figure 26:
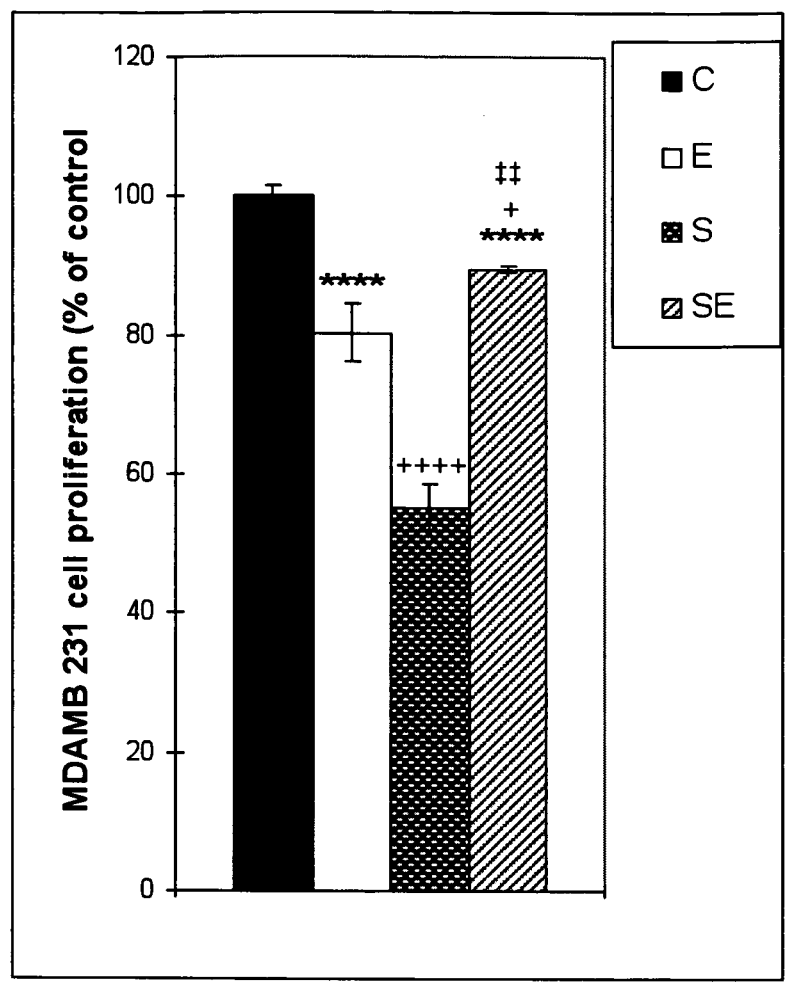

FIG. 26. Effect of soy extract, estradiol-17β or both on cell proliferation of cultured human MDAMB-231 mammary cancer cells. Estradiol (E), soy extract (S), soy extract plus estradiol (SE) or vehicle (C) was added to the culture media and number of cells was evaluated 72 h later. Bars indicate means (expressed as % of values in controls)±standard error of the mean. Statistics: Least significant difference a posteriori LSD test (LSD), ****$p<0.0001$, compared to the homologous condition without E treatment; +$p<0.05$, ++++ $p<0.0001$, compared to the homologous condition without pretreatment with genistein; ‡‡$p<0.0001$, compared to controls without any treatment.

Figure 27:
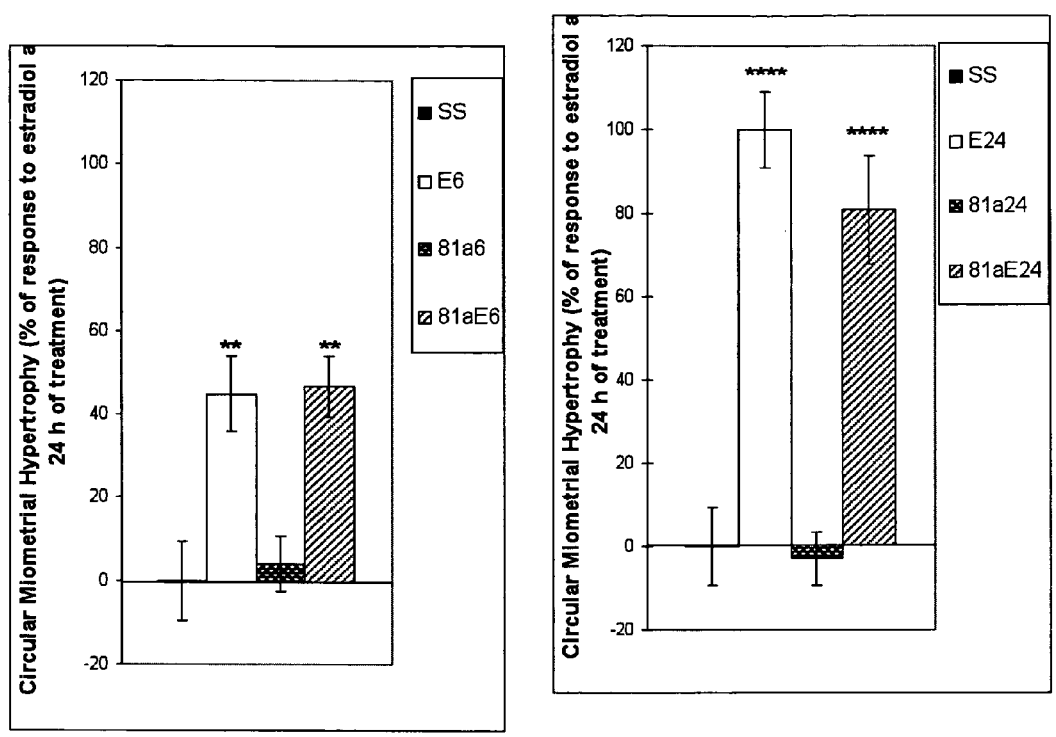
Figure 28:
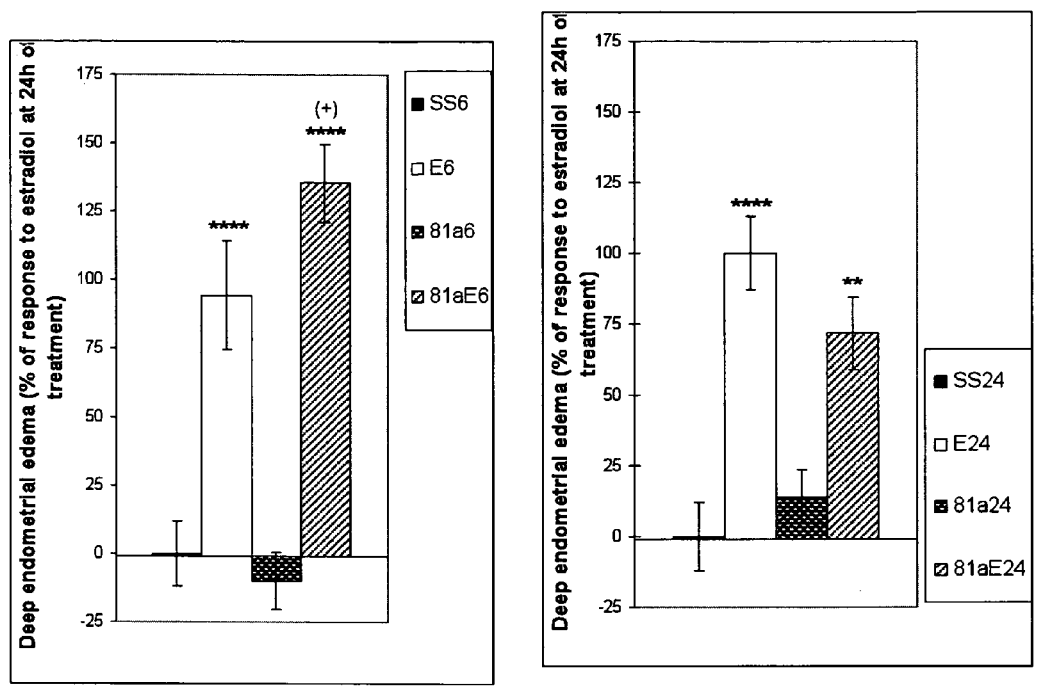

FIG. 27. Effect of plant extract Le81a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (81a), the extract followed by estradiol 1 h later (81 aE) or saline physiological solution:ethanol 9:1 as vehicle (SS). The uteri were excised 6 h (E6, 81a6, 81aE6 or SS) or 24 h (E24, 81a24, 81aE24 or SS) after estradiol or vehicle administration, under anesthesia. Bars indicate means (expressed as % of response to estradiol at 24 h of treatment)±standard error of the mean. Statistics: Least significant difference a posteriori LSD test (LSD), $p<0.01$, $p<0.0001$, compared to the homologous condition without E treatment FIG. 28. Effect of plant extract Le81a and/or estradiol on deep endometrial edema. Prepubertal rats received s.c. 0.33 mg estradiol-17β/kg b.wt (E), 6 mL of the extract diluted in saline physiological solution 1:9)/kg b.wt. (81a), the extract followed by estradiol 1 h later (81 aE) or saline physiological solution:ethanol 9:1 as vehicle (SS). The uteri were excised 6 h (E6, 81a6, 81aE6 or SS6) or 24 h (E24, 81a24, 81aE24 or SS24) after estradiol or vehicle administration, under anesthesia. Bars indicate means (expressed as % of response to estradiol at 6 h of treatment)±standard error of the mean. Statistics: Least significant difference a posteriori LSD test (LSD), $p<0.01$, ****$p<0.0001$, compared to the homologous condition without E treatment; (+) $0.05<p<0.1$, compared to the homologous condition without pretreatment with the extract Le81a.

Figure 29:
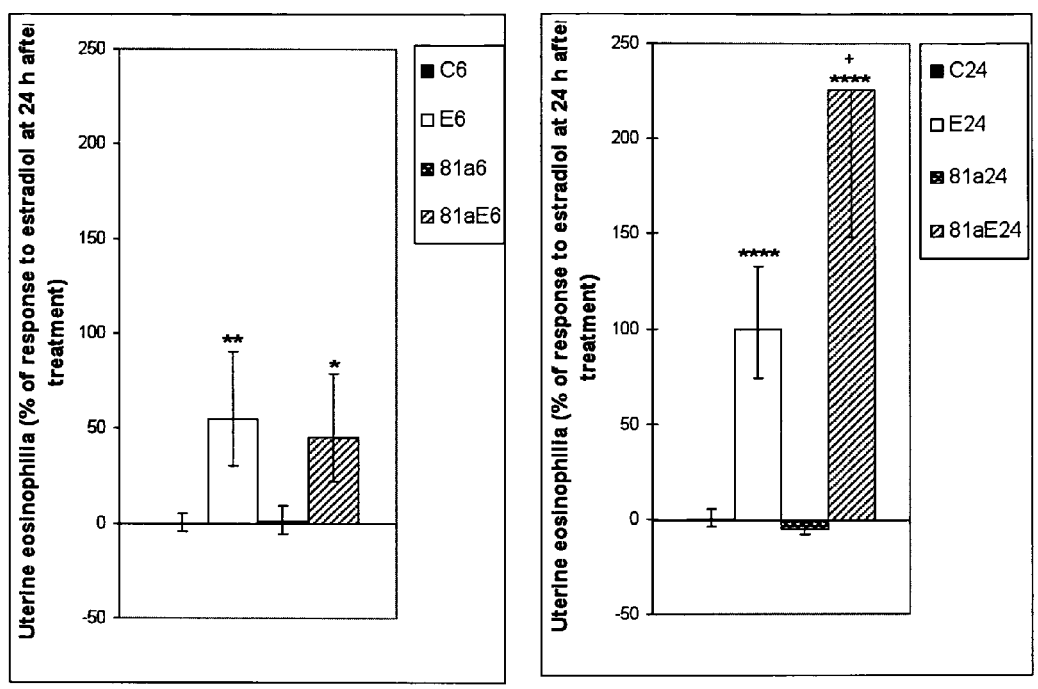

FIG. 29. Effect of plant extract Le81a and/or estradiol on uterine eosinophilia. Prepubertal rats received s.c. 0.33 mg estradiol-17β/kg b.wt (E), 6 mL of the extract diluted in saline physiological solution 1:9)/kg b.wt. (81a), the extract followed by estradiol 1 h later (81 aE) or saline physiological solution:ethanol 9:1 as vehicle (C). The uteri were excised 6 h (E6, 81a6, 81aE6 or C6) or 24 h (E24, 81a24, 81aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *$p<0.05$, $p<0.01$, **$p<0.0001$, compared to the homologous condition without E treatment; +$p<0.05$, compared to the homologous condition without pretreatment with the extract Le81a.

Figure 30:
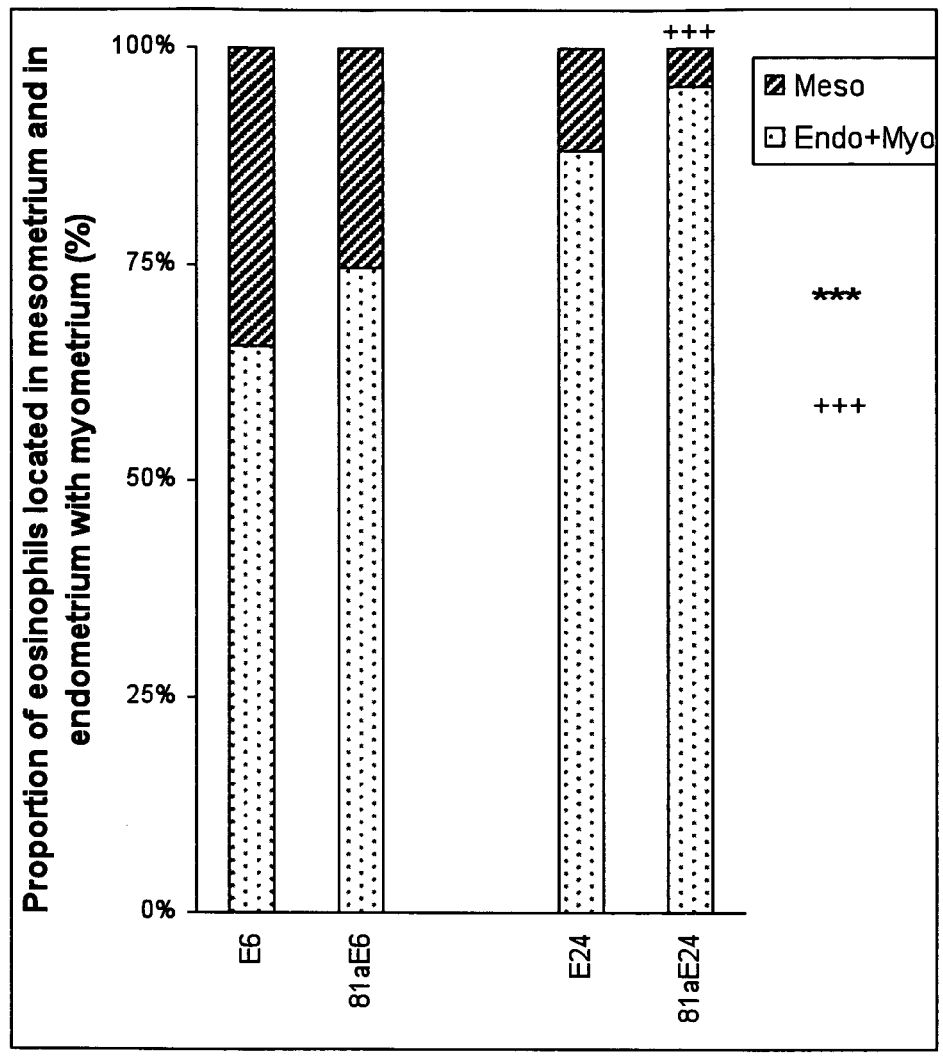

FIG. 30. Effect of plant extract Le81a and estradiol-17β on the proportion of uterine eosinophils located in the mesometrium and in the endometrium with myometrium. Prepubertal rats received s.c. 0.33 mg estradiol-17β/kg b.wt (E), 6 mL of the extract diluted in saline physiological solution 1:9)/kg b.wt. (81a), the extract followed by estradiol 1 h later (81 aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +++, $p<0.001$; comparisons to animals treated with estradiol alone.

Figure 31:
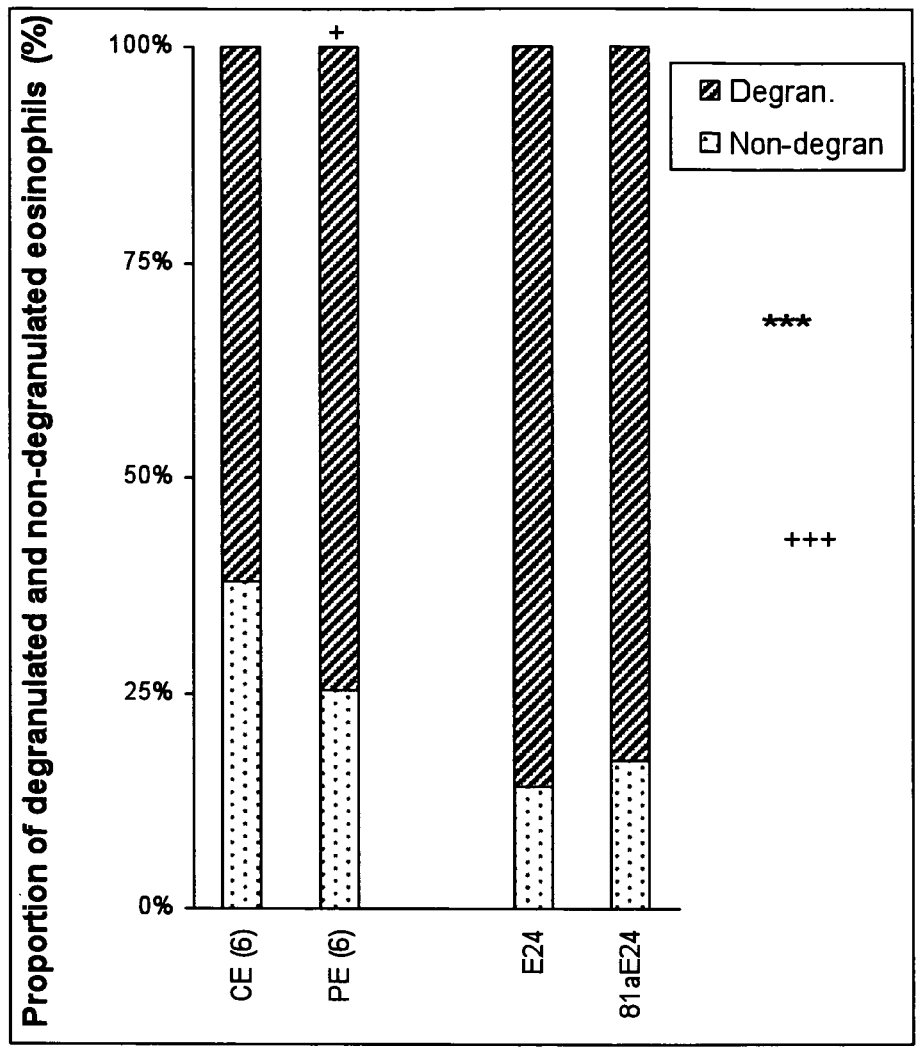

FIG. 31. Effect of plant extract Le81a and estradiol-17β on the proportion of degranulated and non-degranulated uterine eosinophils Prepubertal rats received s.c. 0.33 mg estradiol-17β/kg b.wt (E), 6 mL of the extract diluted in saline physiological solution 1:9)/kg b.wt. (81a), the extract followed by estradiol 1 h later (81aF) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +, $p<0.05$; comparisons to animals treated with estradiol alone.

Figure 32:
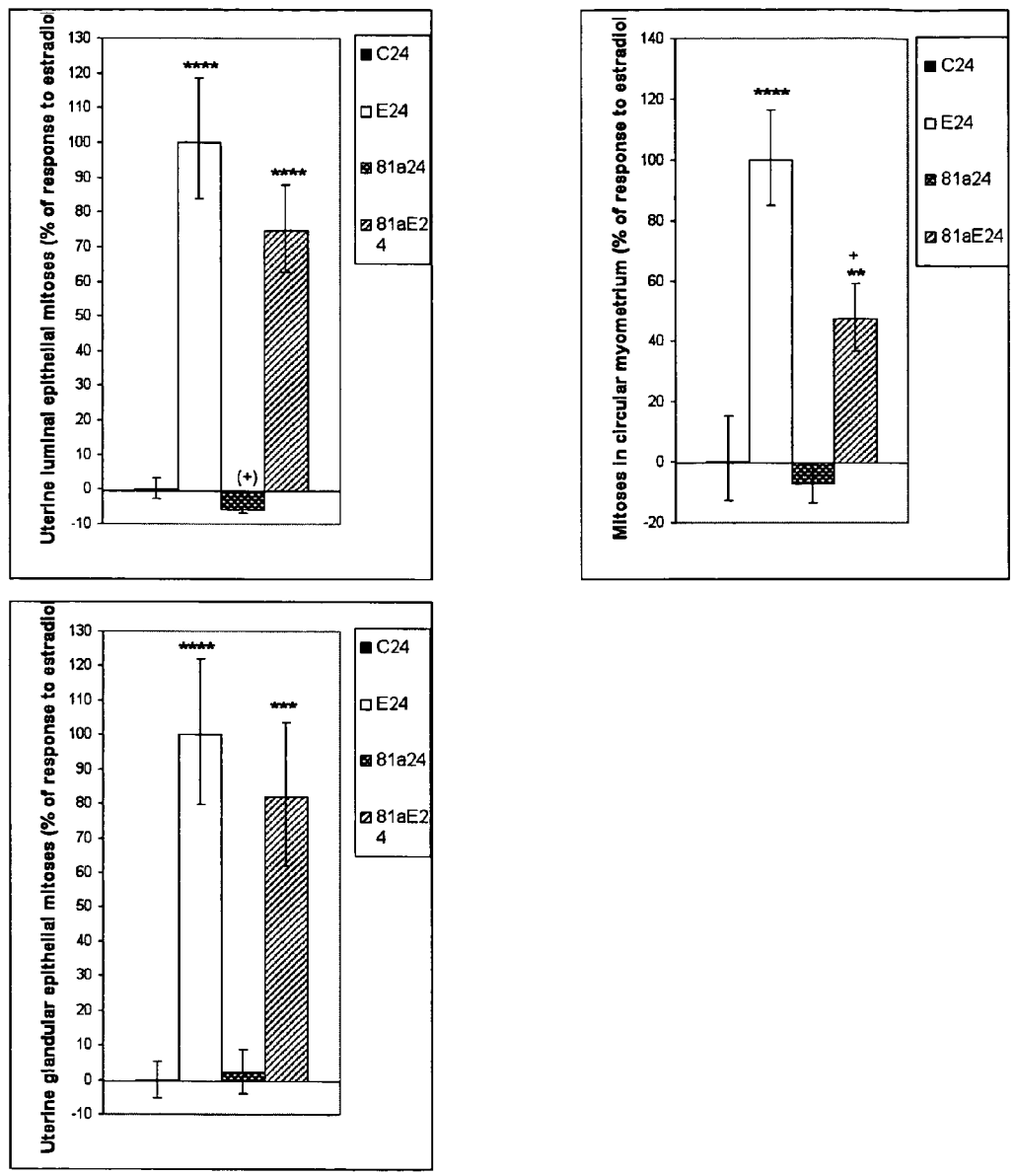

FIG. 32. Effect of plant extract Le81a and/or estradiol on the proliferative response in uterine luminal epithelium, glandular epithelium, and myometrium. Prepubertal rats received s.c. 0.33 mg estradiol-17β/kg b.wt (E24), 6 mL of the extract diluted in saline physiological solution 1:9)/kg b.wt. (81a24), the extract followed by estradiol 1 h later (81aE24) or saline physiological solution:ethanol 9:1 as vehicle (C24). The uteri were excised 24 h after estradiol or vehicle administration, under anesthesia. Bars indicate means (expressed as % of response to estradiol at 24 h of treatment)±standard error of the mean. Statistics: Least significant difference a posteriori LSD test (LSD), $p<0.01$, *$p<0.001$, ****$p<0.0001$, compared to the homologous condition without E treatment; (+)$0.05<p<0.1$, +$p<0.05$, compared to the homologous condition without pretreatment with the extract Le81a.

Figure 33:
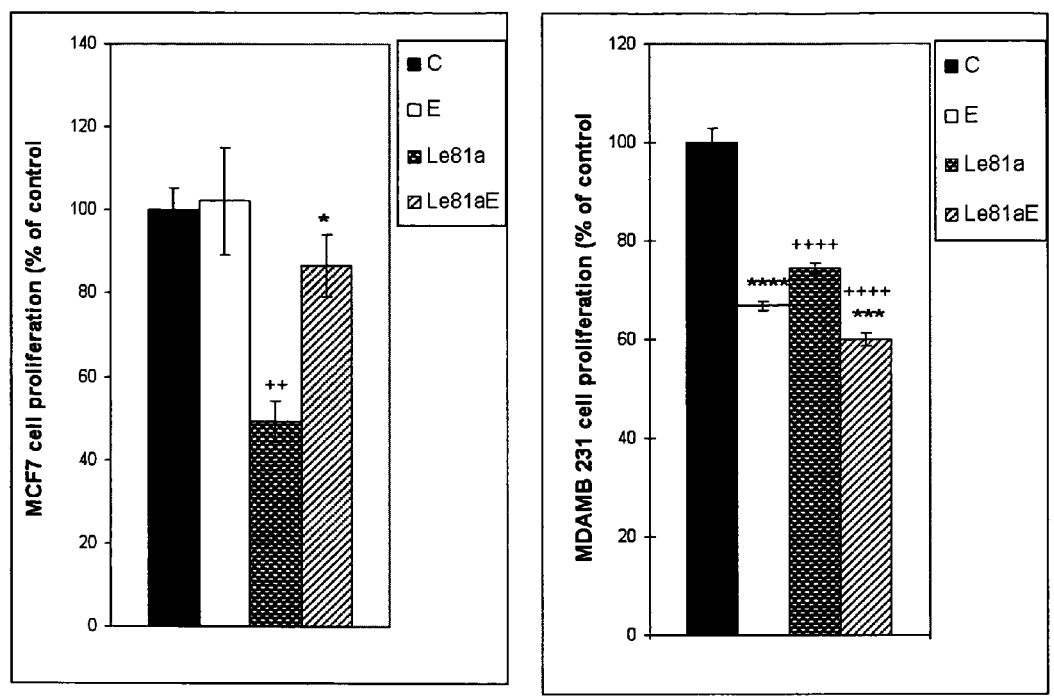

FIG. 33. Effect of plant extract Le81a, estradiol-17β or both on cell proliferation of cultured human MCF-7 and MDAMB-231 mammary cancer cells. Estradiol (E), plant extract (81a), plant extract plus estradiol (81aF) or vehicle (C) was added to the culture media and number of cells was evaluated 72 h later. Bars indicate means (expressed as % of values in controls)±standard error of the mean. Statistics: Least significant difference a posteriori LSD test (LSD), *p<0.05, *p<0.001, **p<0.0001, compared to the homologous condition without E treatment; ++p<0.01, ++++p<0.0001, compared to the homologous condition without pretreatment with the plant extract.

Figure 34:
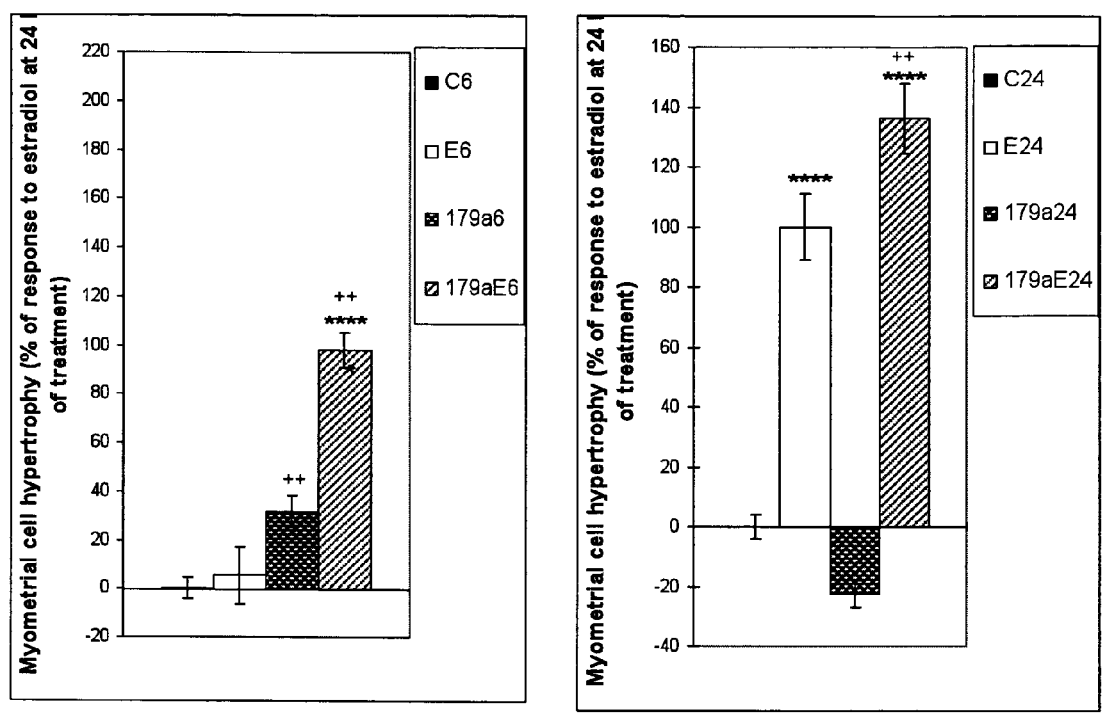

FIG. 34. Effect of plant extract Le179a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), ****p<0.0001, compared to the homologous condition without E treatment; ++p<0.01, compared to the homologous condition without pretreatment with the extract Le179a.

Figure 35:
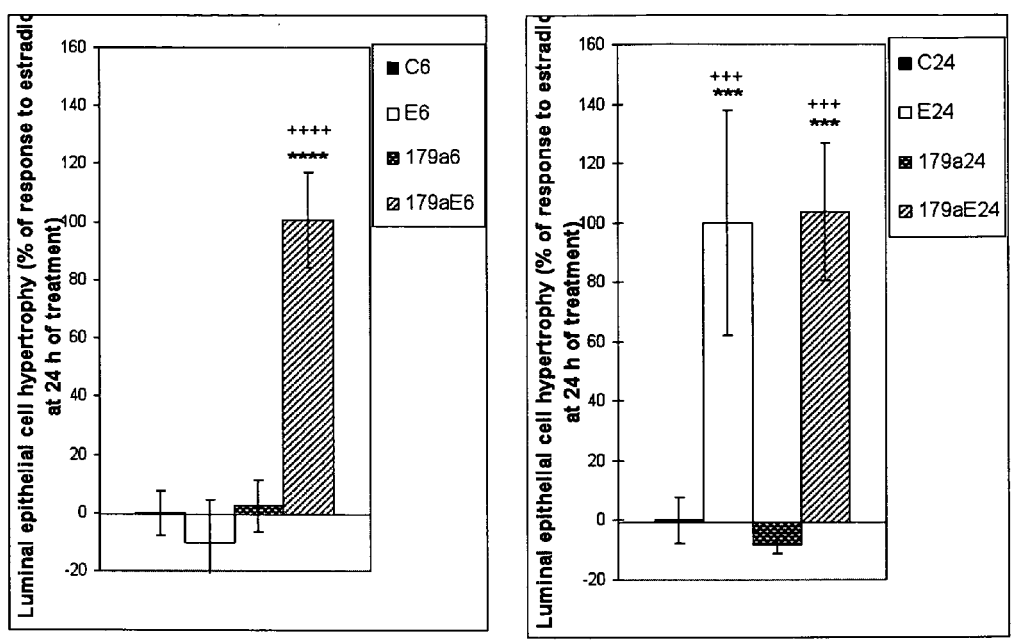

FIG. 35. Effect of plant extract Le179a and/or estradiol on cell hypertrophy uterine luminal epithelium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, **p<0.0001, compared to the homologous condition without E treatment; +++p>0.001, ++++p<0.0001, compared to the homologous condition without pretreatment with the extract.

Figure 36:
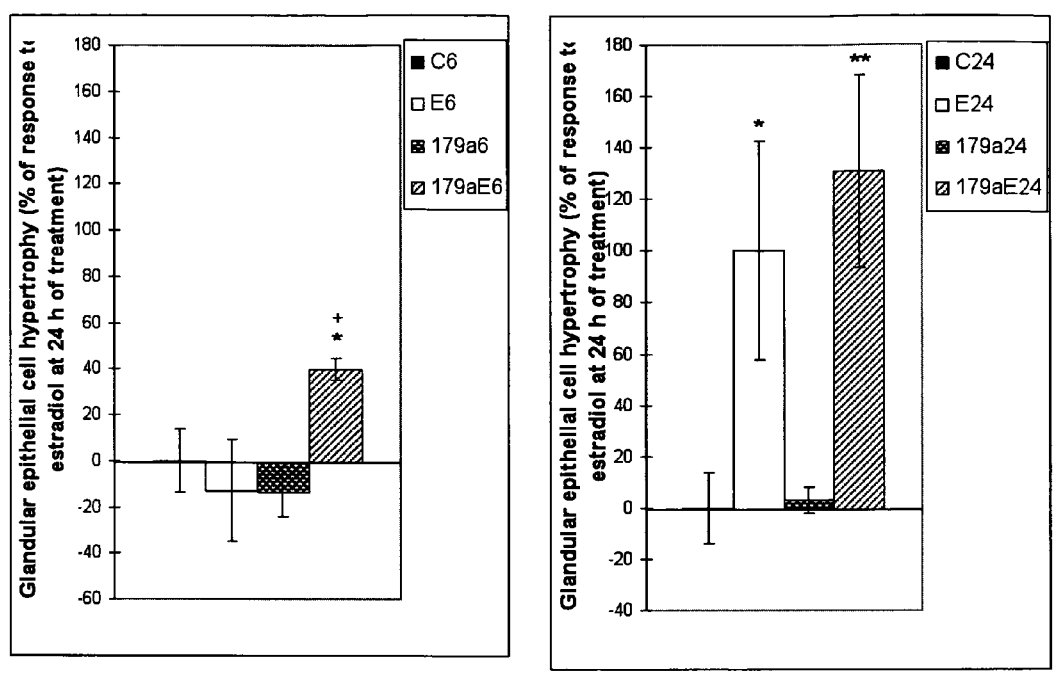

FIG. 36. Effect of plant extract Le179a and/or estradiol on cell hypertrophy in uterine glandular epithelium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), *p<0.05, **p<0.01, compared to the homologous condition without E treatment; +p<0.05, compared to the homologous condition without pretreatment with the extract Le179a.

Figure 37:
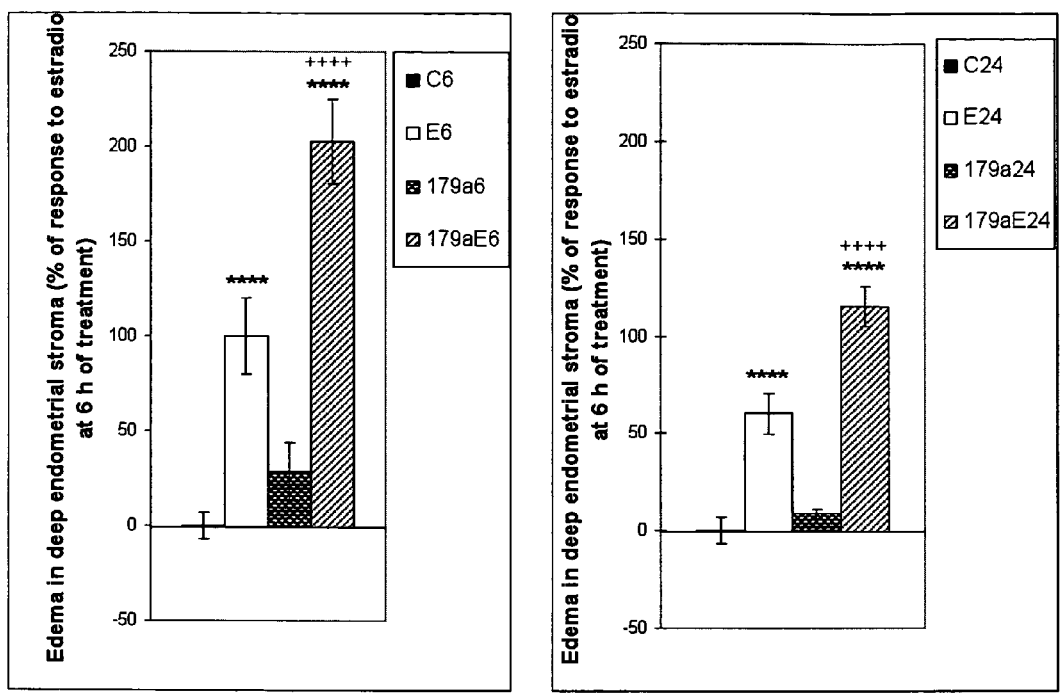

FIG. 37. Effect of plant extract Le179a and/or estradiol on deep endometrial stroma edema. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 6 h of treatment)±standard error of the mean. Statistics: Least significant difference a posteriori LSD test (LSD), ****p<0.0001, compared to the homologous condition without E treatment, ++++p<0.0001, compared to the homologous condition without pretreatment with the extract Le179a.

Figure 38:
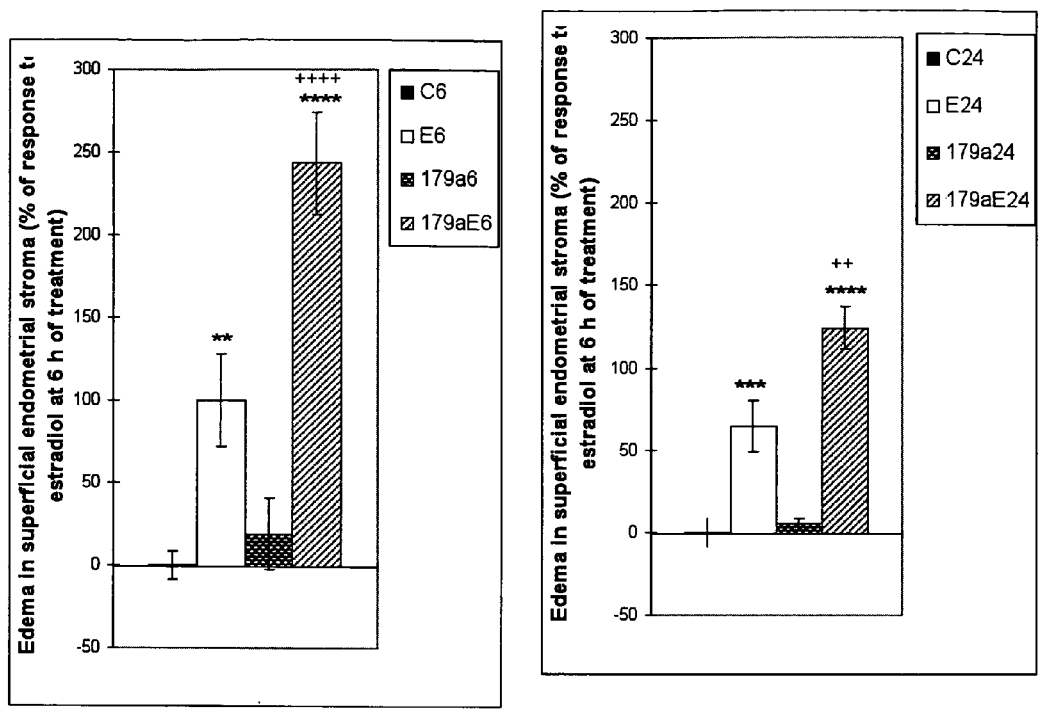

FIG. 38. Effect of plant extract Le179a and/or estradiol on superficial endometrial stroma edema. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 6 h of treatment)±standard error of the mean. Statistics: Least significant difference a posteriori LSD test (LSD), p<0.01, *p<0.001, ****p<0.0001, compared to the homologous condition without E treatment; ++p<0.01, ++++p<0.0001, compared to the homologous condition without pretreatment with the extract Le179a.

Figure 39:
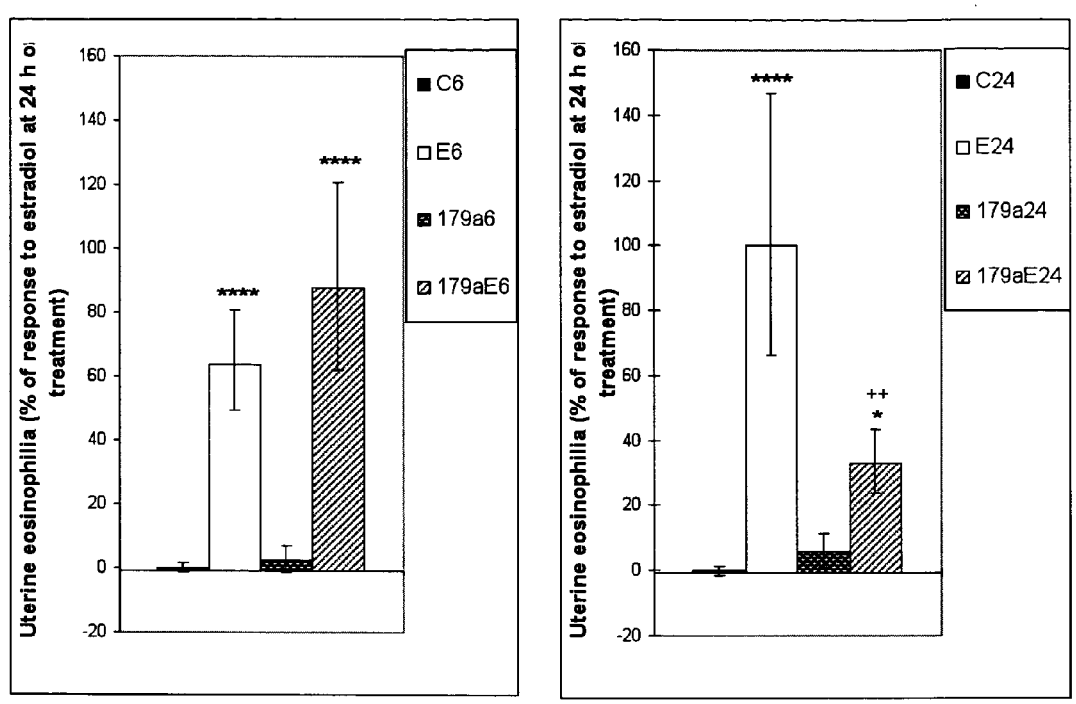

FIG. 39. Effect of plant extract Le179a and/or estradiol on uterine eosinophilia. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), *p<0.05, ****p<0.0001, compared to the homologous condition without E treatment; ++p<0.01, compared to the homologous condition without pretreatment with the extract Le179a.

Figure 40:
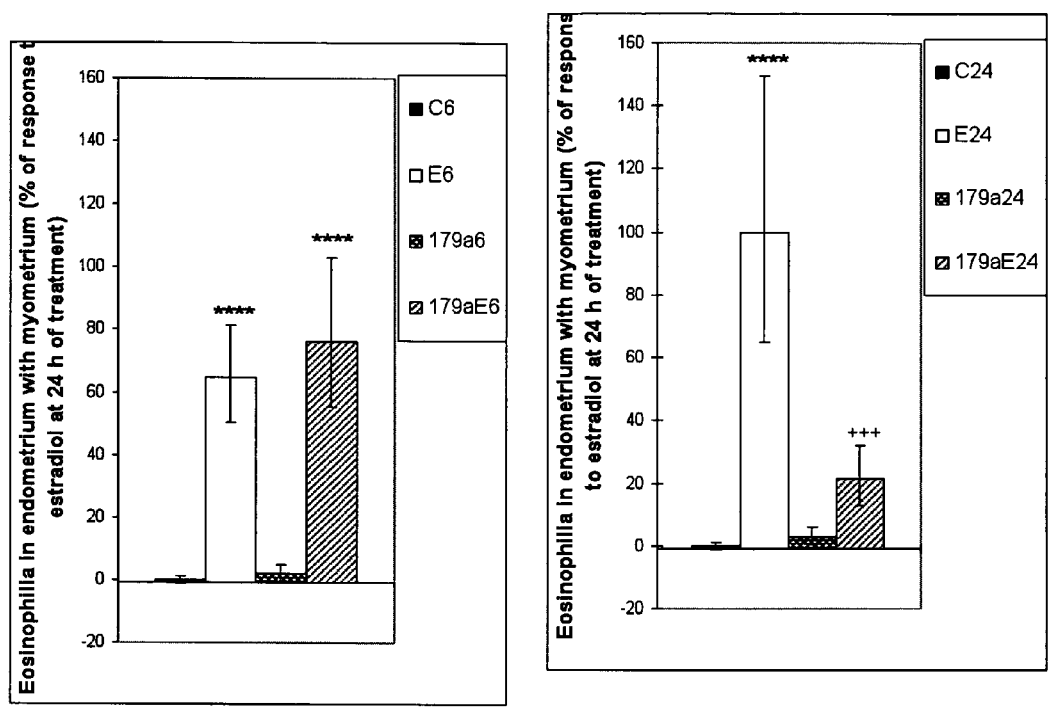

FIG. 40. Effect of plant extract Le179a and/or estradiol on tissue eosinophilia in endometrium with myometrium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), ****p<0.0001, compared to the homologous condition without E treatment; +++p>0.001, compared to the homologous condition without pretreatment with the extract Le179a.

Figure 41:
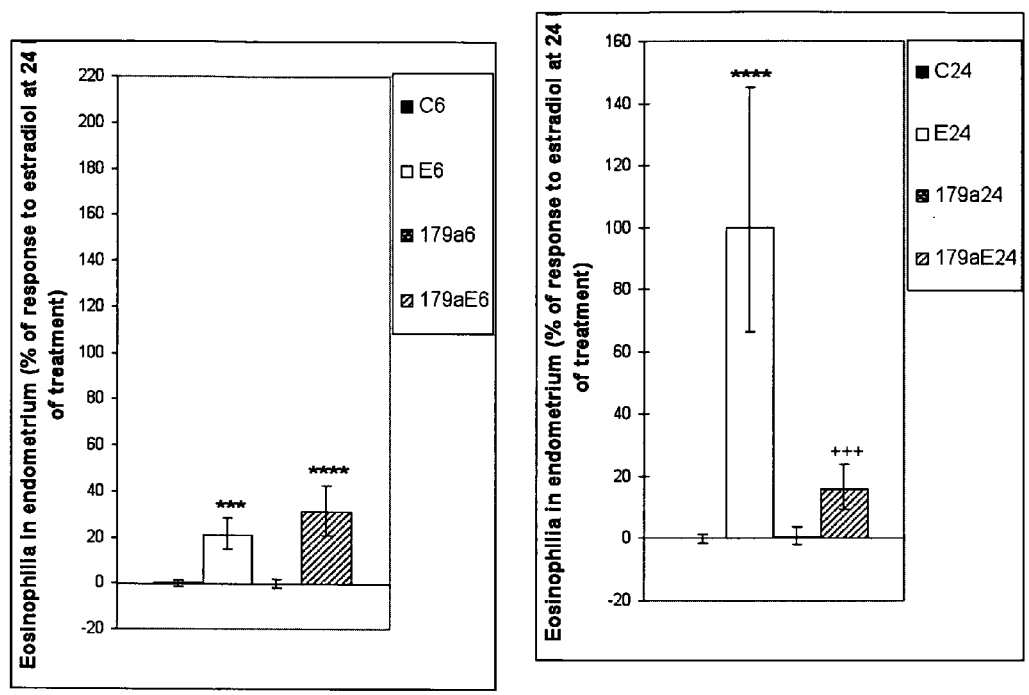

FIG. 41. Effect of plant extract Le179a and/or estradiol on tissue eosinophilia in the endometrium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, **p<0.0001, compared to the homologous condition without E treatment; +++p>0.001, compared to the homologous condition without pretreatment with the extract Le179a.

Figure 42:
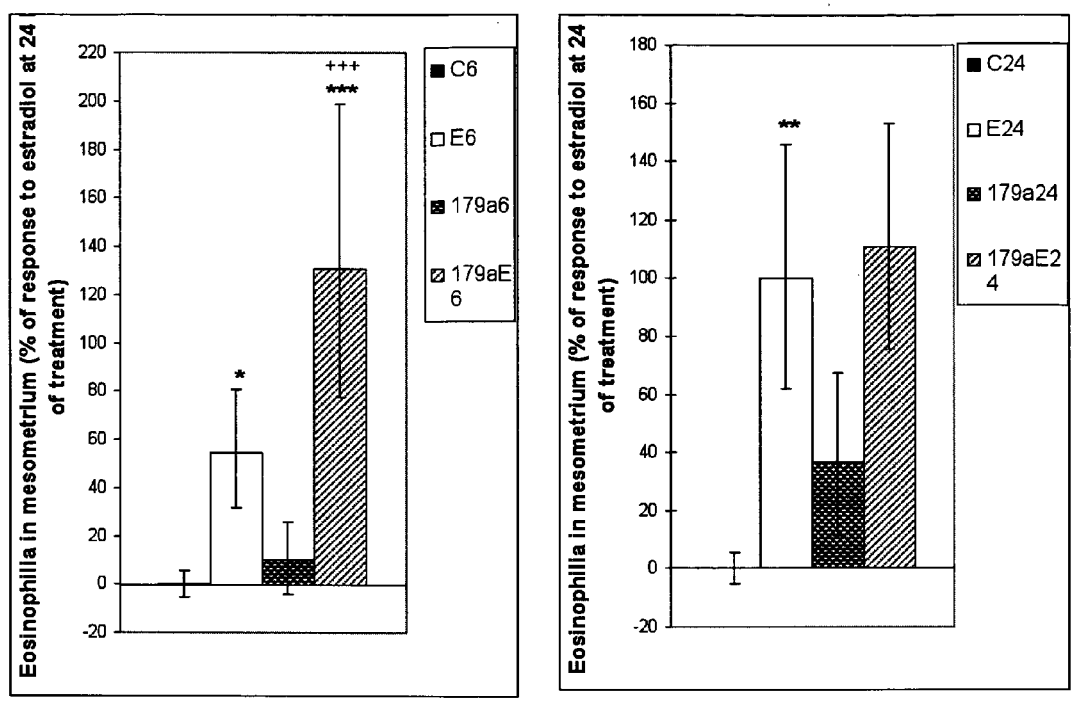

FIG. 42. Effect of plant extract Le179a and/or estradiol on tissue eosinophilia in the mesometrium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), *$p<0.05$, $p<0.01$, *$p<0.001$, compared to the homologous condition without E treatment; +++$p>0.001$, compared to the homologous condition without pretreatment with the extract Le179a.

Figure 43:
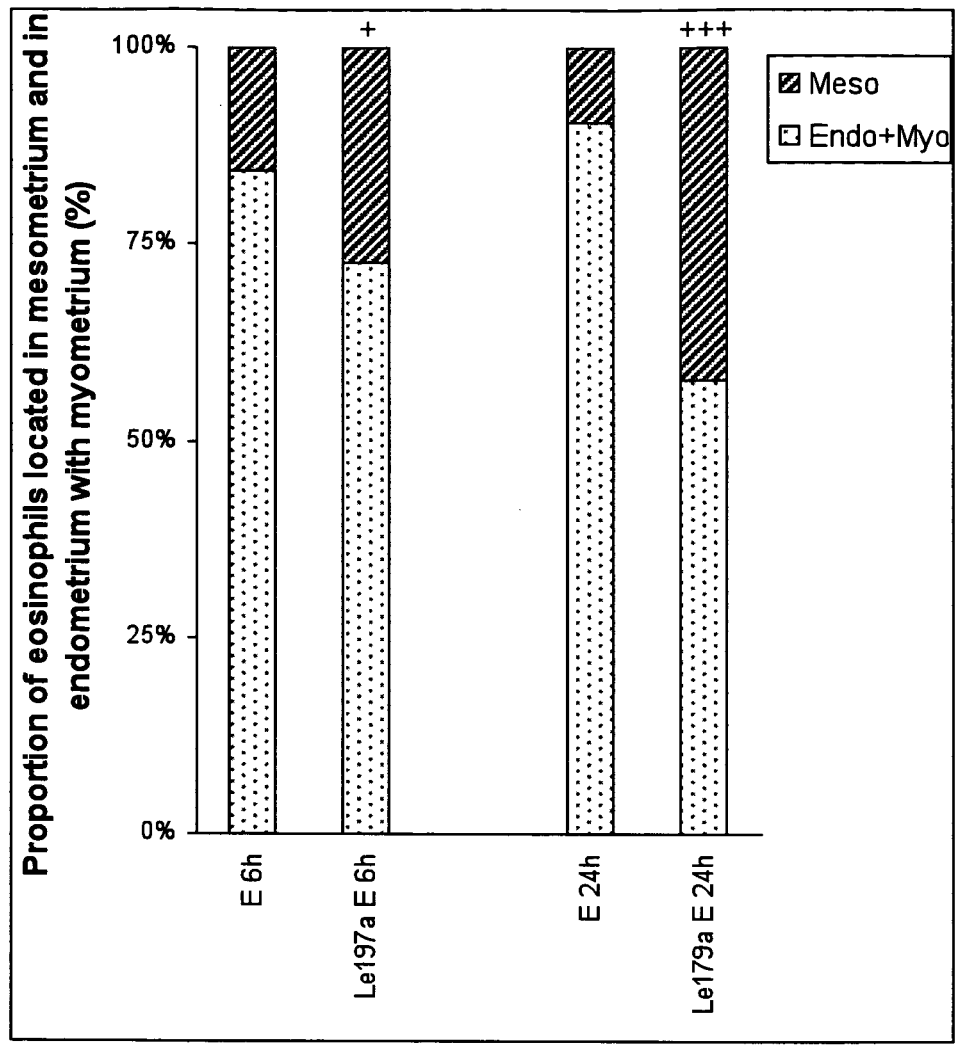

FIG. 43. Effect of plant extract Le179a and estradiol-17β on the proportion of uterine eosinophils located in the mesometrium and in the endometrium with myometrium. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +, $p<0.05$; +++, $p<0.001$; comparisons to animals treated with estradiol alone.

Figure 44:
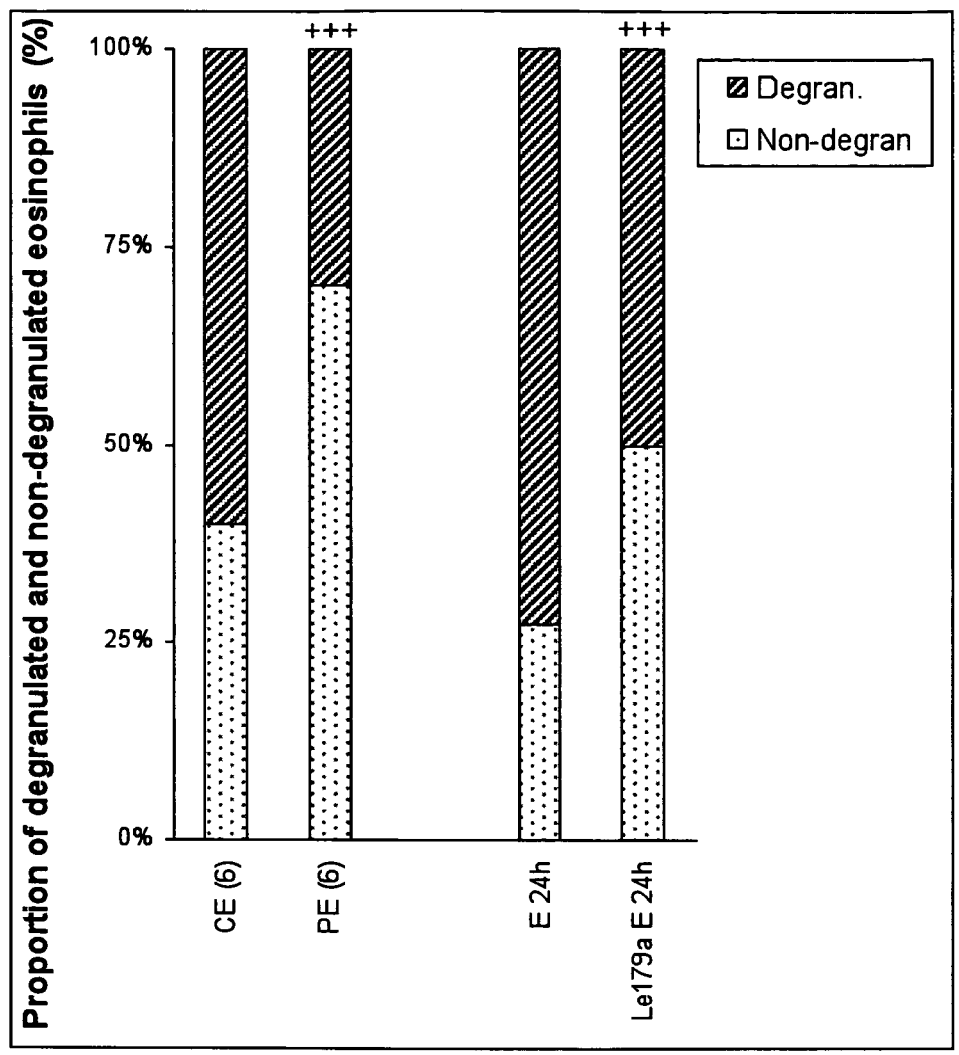

FIG. 44. Effect of plant extract Le179a and estradiol-17β on the proportion of degranulated and non-degranulated uterine eosinophils. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test, +++, $p<0.001$; comparisons to animals treated with estradiol alone.

Figure 45:
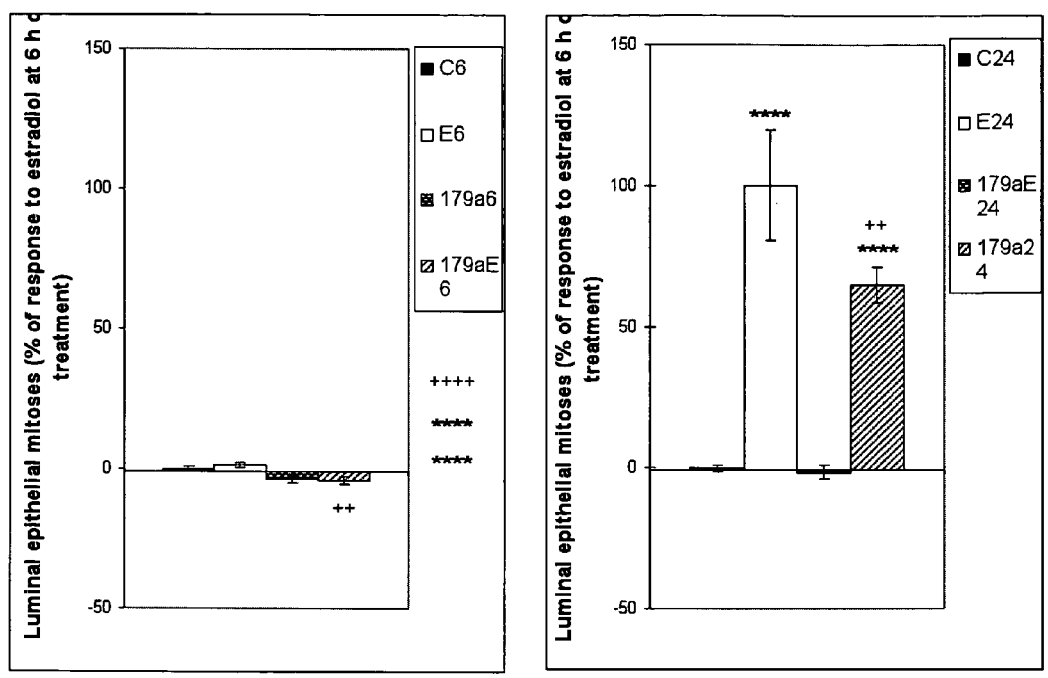

FIG. 45. Effect of plant extract Le179a and/or estradiol on uterine luminal epithelium mitoses. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aR24 or C24) following estradiol or vehicle administration, under anesthesia. Bars indicate means (expressed as % of response to estradiol at 24 h of treatment) ±standard error of the mean. Statistics: Least significant difference a posteriori LSD test (LSD), ****$p<0.0001$, compared to the homologous condition without E treatment; ++$p<0.01$, compared to the homologous condition without pretreatment with the extract Le179a.

Figure 46:
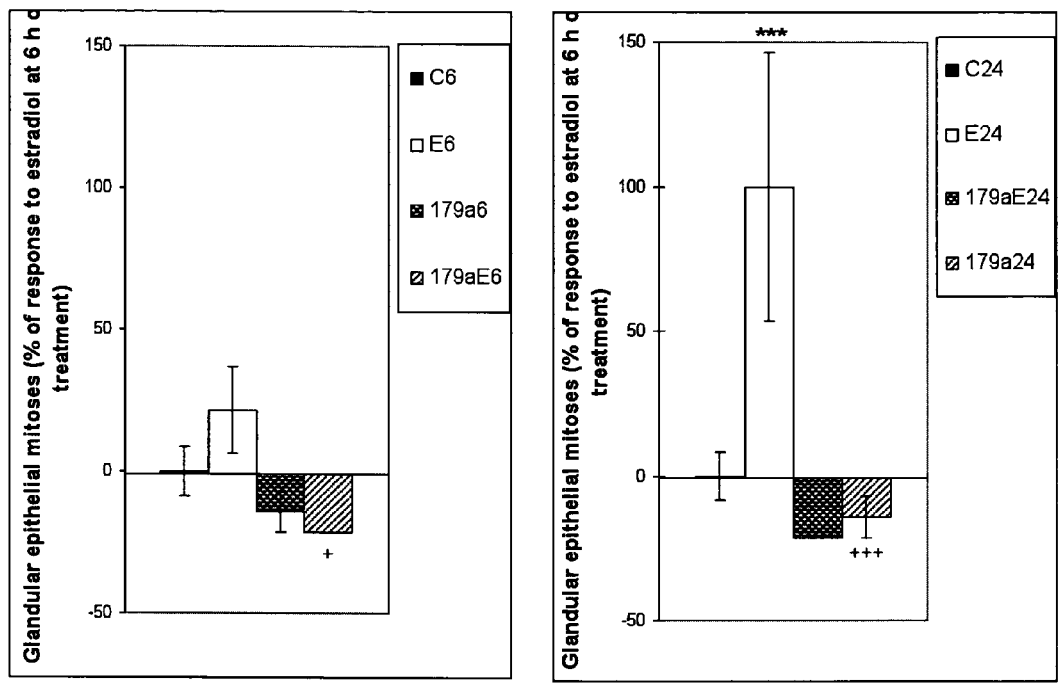

FIG. 46. Effect of plant extract Le179a and/or estradiol on uterine glandular epithelium mitoses. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), ***$p<0.001$, compared to the homologous condition without E treatment; +$p<0.05$, +++$p>0.001$, compared to the homologous condition without pretreatment with the extract Le179a.

Figure 47:
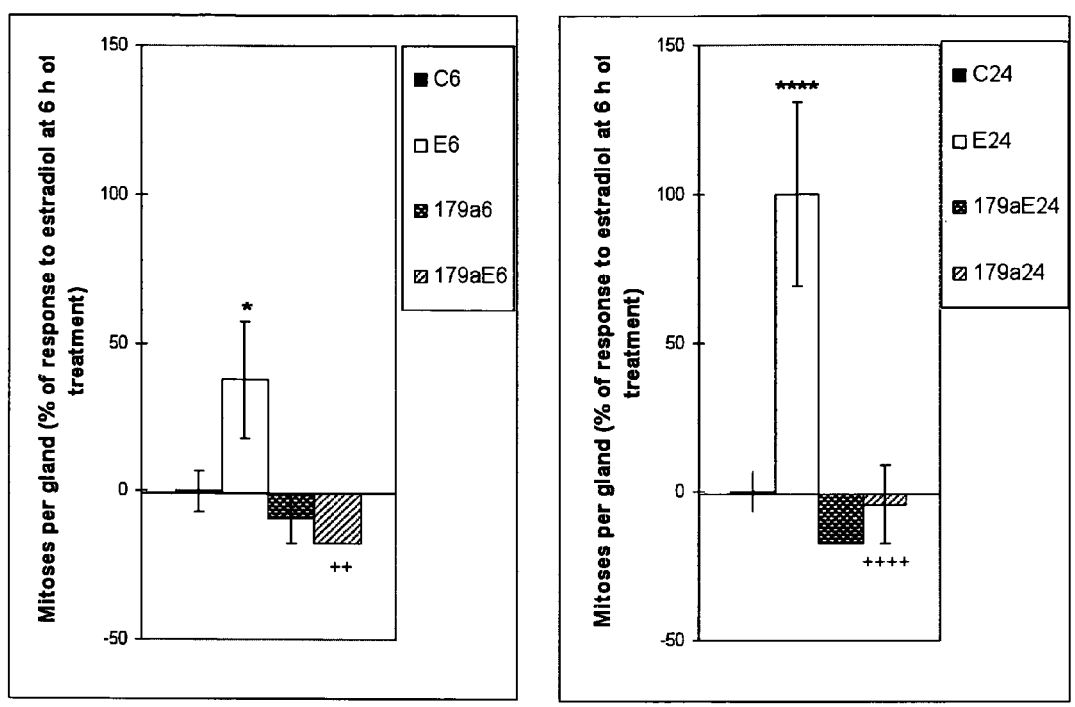
Figure 48:
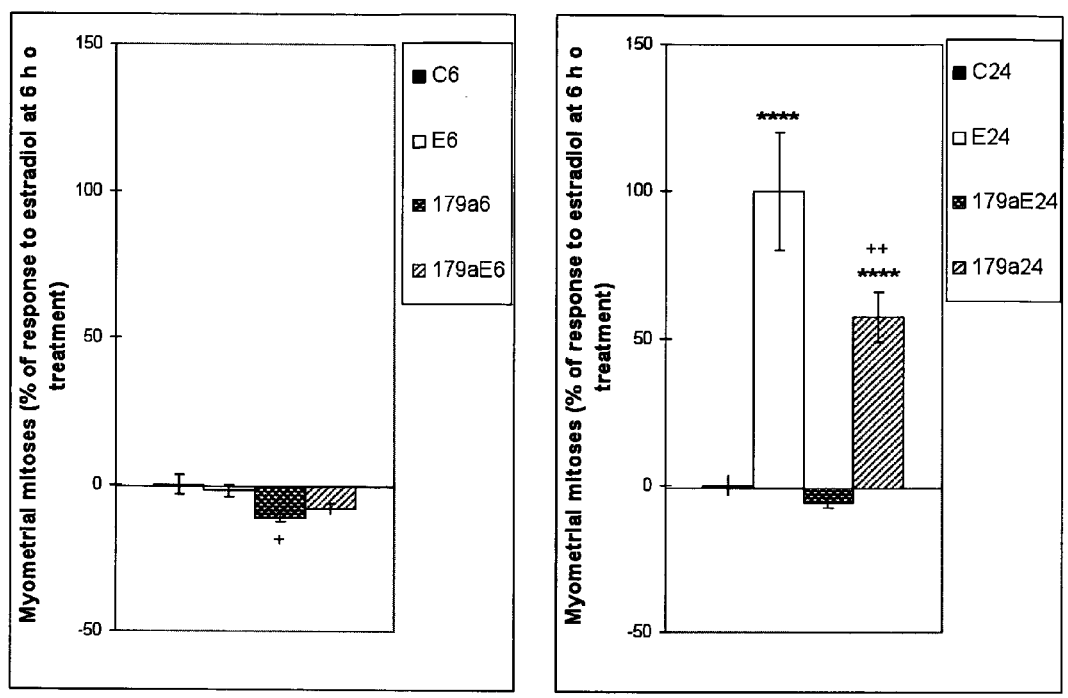

FIG. 47. Effect of plant extract Le179a and/or estradiol on on uterine glandular epithelium mitoses. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment, measured as number of mitoses per gland)±standard error of the mean. Statistics: Least significant difference a posteriori LSD test (LSD), *$p<0.05$, **$p<0.0001$, compared to the homologous condition without E treatment; ++$p<0.01$, ++++$p<0.0001$, compared to the homologous condition without pretreatment with the extract Le179a FIG. 48. Effect of plant extract Le179a and/or estradiol on myometrial mitoses. Prepubertal rats received s.c. 0.33 mg estradiol-17β/kg b.wt (E), 6 mL of the extract diluted in saline physiological solution 1:9)/kg b.wt. (179a), the extract followed by estradiol 1 h later (179aE) or saline physiological solution:ethanol 9:1 as vehicle (C). The uteri were excised 6 h (E6, 179a6, 179aE6 or C6) or 24 h (E24, 179a24, 179aE24 or C24) following estradiol or vehicle administration, under anesthesia. Bars indicate means (expressed as % of response to estradiol at 24 h of treatment)±standard error of the mean. Statistics: Least significant difference a posteriori LSD test (LSD), **$p<0.0001$, compared to the homologous condition without E treatment; +$p<0.05$, ++$p<0.01$, compared to the homologous condition without pretreatment with the extract Le179a.

Figure 49:
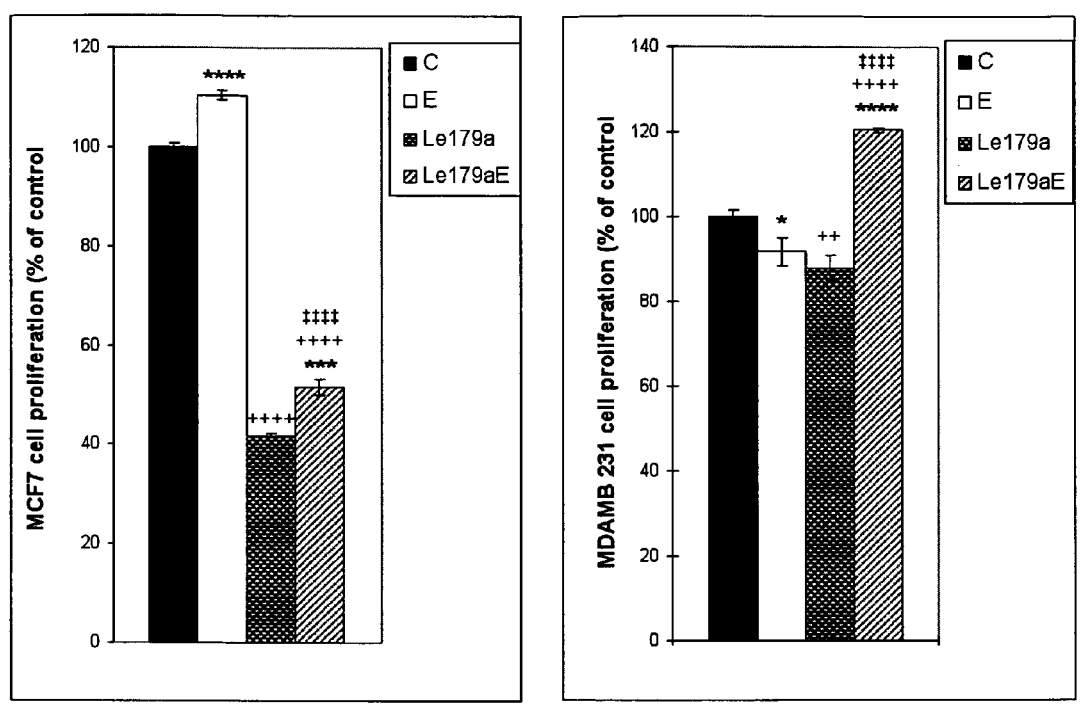

FIG. 49. Effect of plant extract Le179, estradiol-17β or both on cell proliferation of cultured human MCF-7 and MDAMB-231 mammary cancer cells. Estradiol (E), plant extract (179a), plant extract plus estradiol (179aE) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.05$, *$p<0.001$, **$p<0.0001$, compared to the homologous condition without E treatment; ++$p<0.01$, ++++$p<0.0001$, compared to the homologous condition without pretreatment with the extract Le179a; ‡‡‡‡$p<0.0001$, compared to controls without both extract and estradiol.

Figure 50:
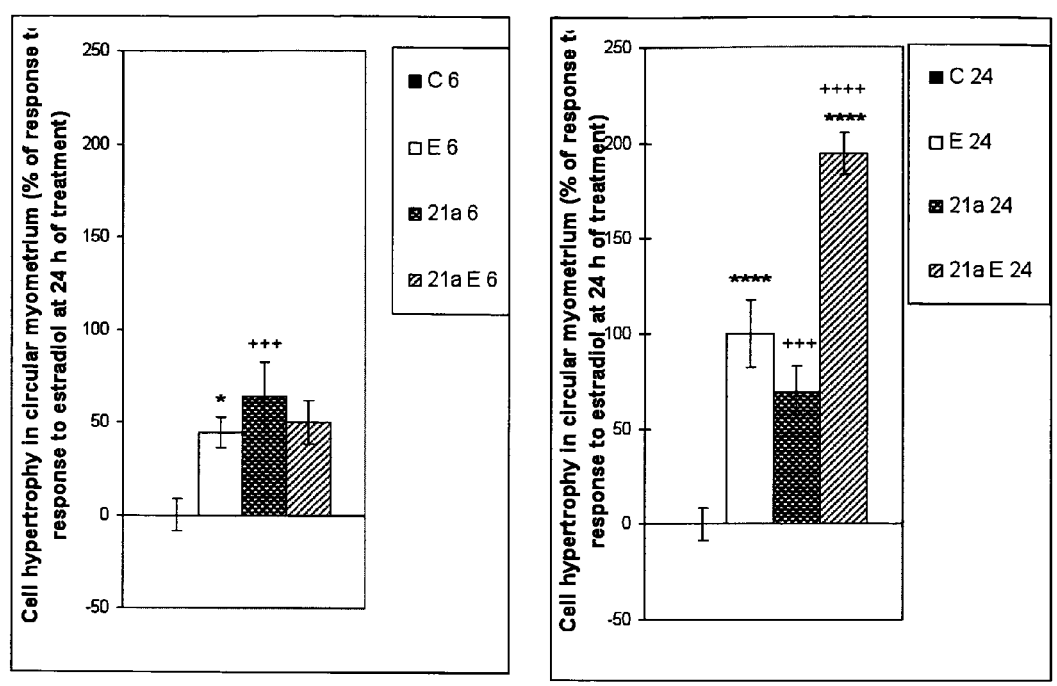

FIG. 50. Effect of plant decoction Le21a and/or estradiol on cell hypertrophy in circular myometrium. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *$p<0.05$, ****$p<0.0001$, compared to the homologous condition without E treatment; +++$p>0.001$, ++++$p<0.0001$, compared to the homologous condition without pretreatment with the decoction Le21a.

Figure 51:
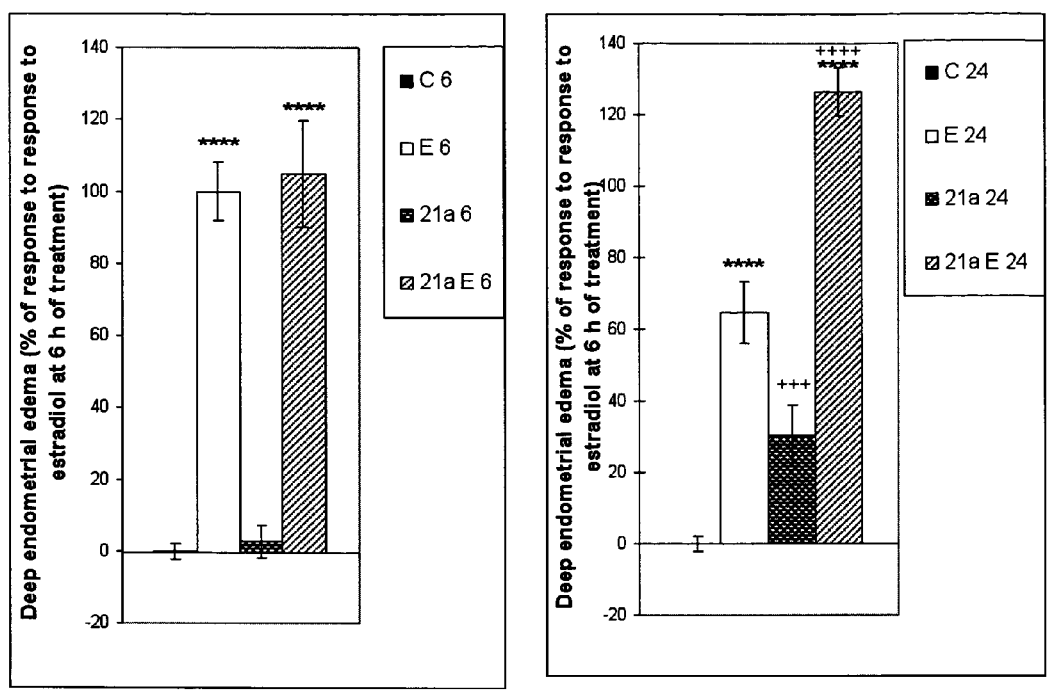

FIG. 51. Effect of plant decoction Le21a and/or estradiol on deep endometrial edema. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 6 h of treatment)±standard error of the mean. Statistics: Least significant difference a posteriori LSD test (LSD),

****p<0.0001, compared to the homologous condition without E treatment; +++p>0.001, ++++p<0.0001, compared to the homologous condition without pretreatment with the decoction Le21a.

Figure 52:
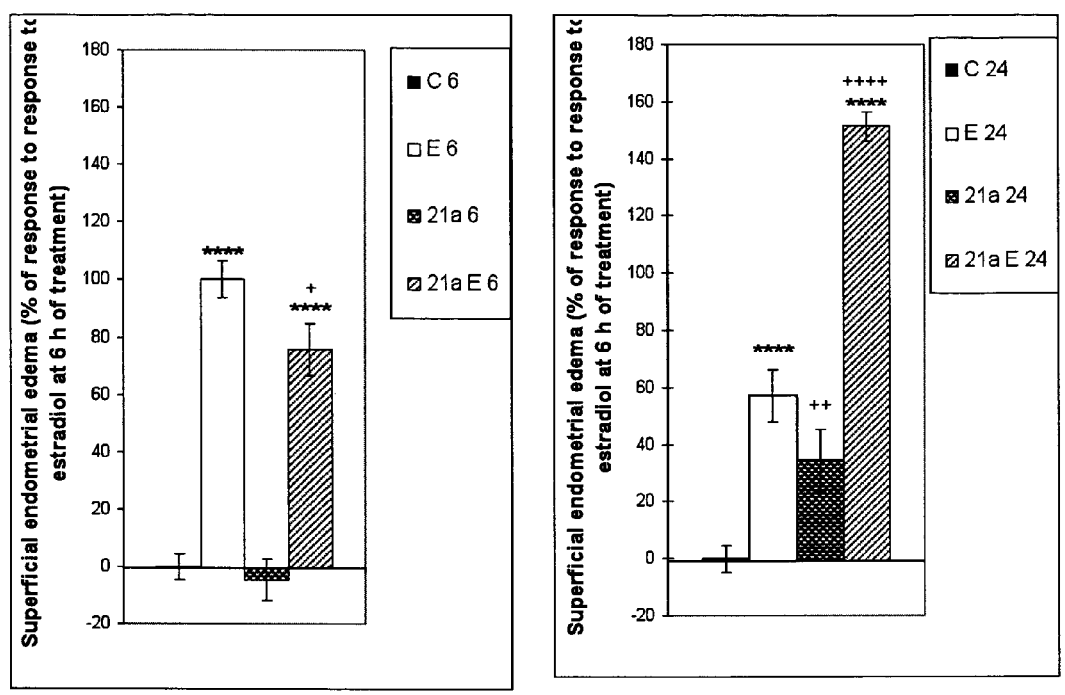

FIG. 52. Effect of plant decoction Le21a and/or estradiol on superficial endometrial edema. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21 aE6 or C6) or 24 h (E24, 21a24, 21 aE24 or C24) after estradiol or vehicle administration, under anesthesia. Bars indicate means (expressed as % of response to estradiol at 6 h of treatment)±standard error of the mean. Statistics: Least significant difference a posteriori LSD test (LSD), ****p<0.0001, compared to the homologous condition without E treatment; +p<0.05, ++p<0.01, p<0.0001, compared to the homologous condition without pretreatment with the decoction Le21a.

Figure 53:
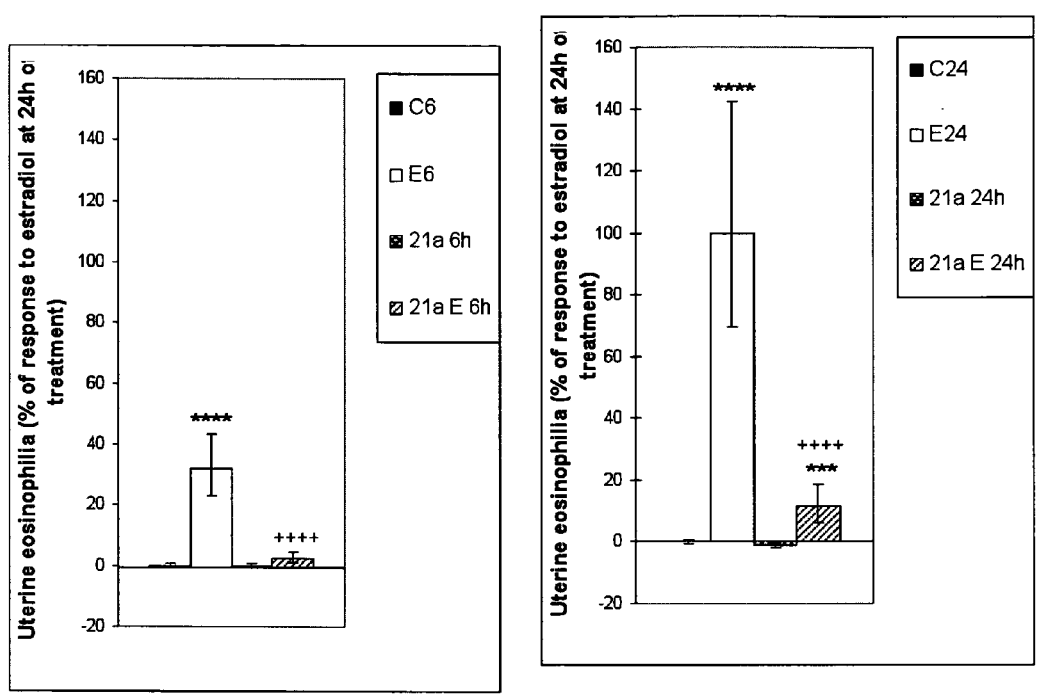

FIG. 53. Effect of plant decoction Le21a and/or estradiol on uterine eosinophilia. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, **p<0.0001, compared to the homologous condition without E treatment; ++++p<0.0001, compared to the homologous condition without pretreatment with the decoction Le21a.

Figure 54:
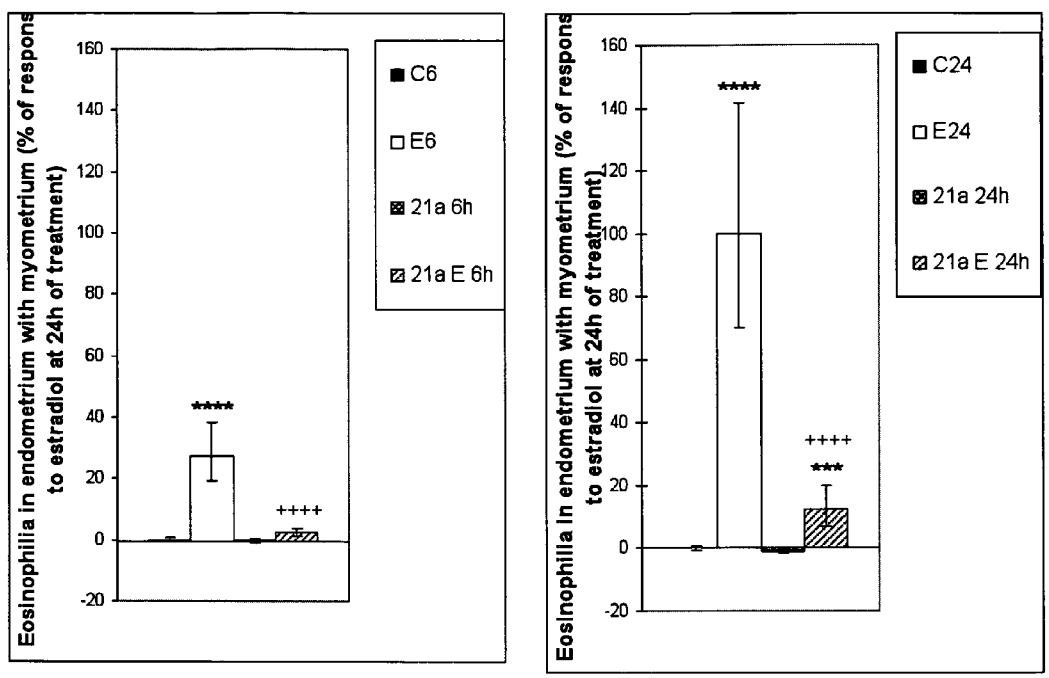

FIG. 54. Effect of plant decoction Le21a and/or estradiol on tissue eosinophilia in endometrium with myometrium. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, **p<0.0001, compared to the homologous condition without E treatment, ++++ p<0.0001, compared to the homologous condition without pretreatment with the decoction Le21a.

Figure 55:
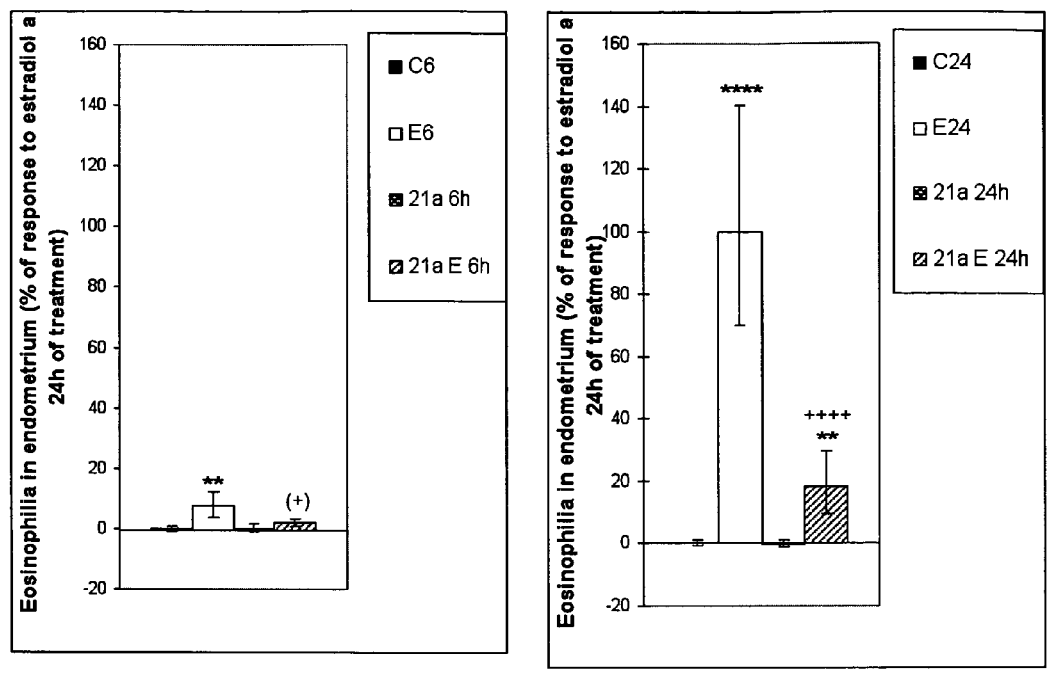

FIG. 55. Effect of plant decoction Le21a and/or estradiol on endometrial eosinophilia. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aF6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), p<0.01, **p<0.0001, compared to the homologous condition without E treatment; (+)0.05<p<0.1, p<0.0001, compared to the homologous condition without pretreatment with the decoction Le21a.

Figure 56:
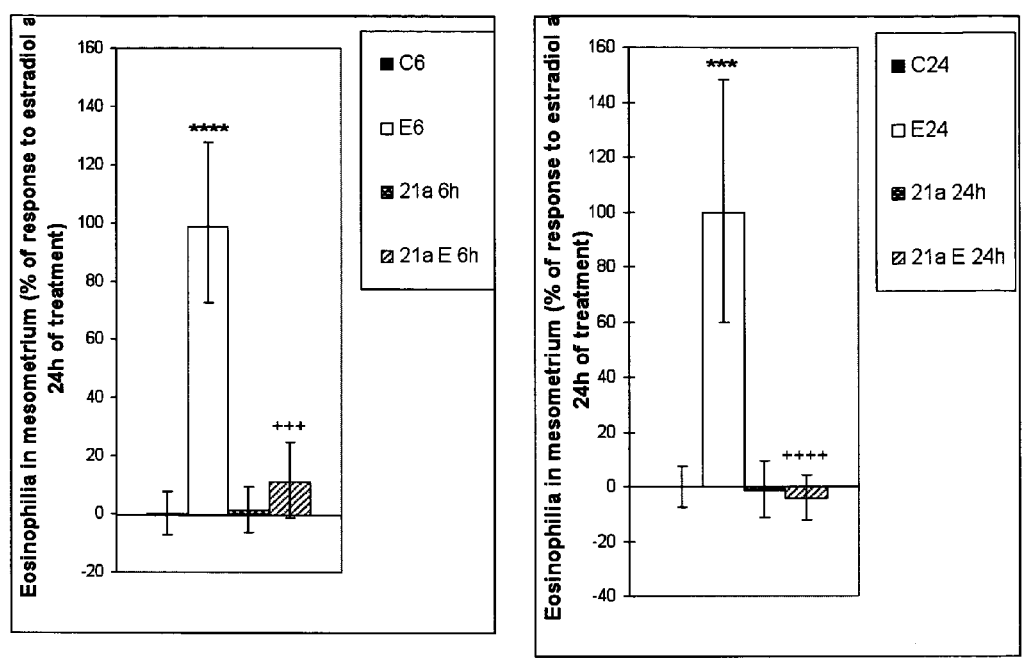

FIG. 56. Effect of plant decoction Le21a and/or estradiol on cell hypertrophy in circular myometrium. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, **p<0.0001, compared to the homologous condition without E treatment; +++p>0.001, ++++p<0.0001, compared to the homologous condition without pretreatment with the decoction Le21a.

Figure 57:
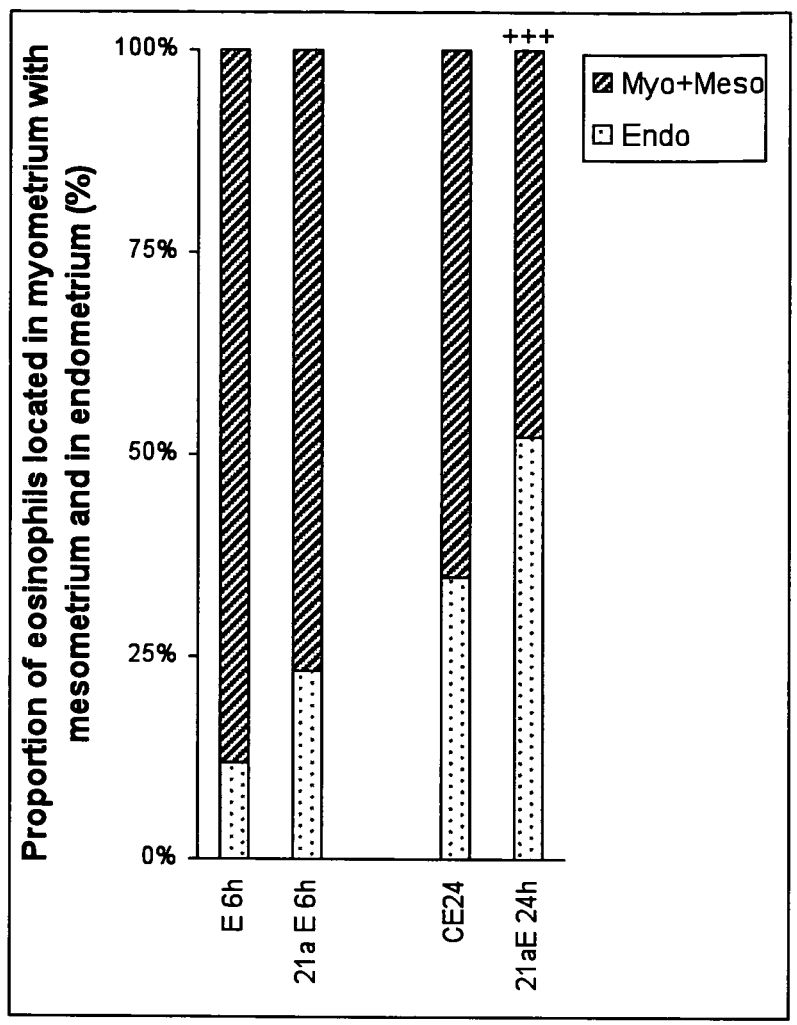

FIG. 57. Effect of plant decoction Le21a and estradiol-17β on the proportion of uterine eosinophils located in the endometrium and in the myometrium with mesometrium. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +++, p<0.001; comparisons to animals treated with estradiol alone.

Figure 58:
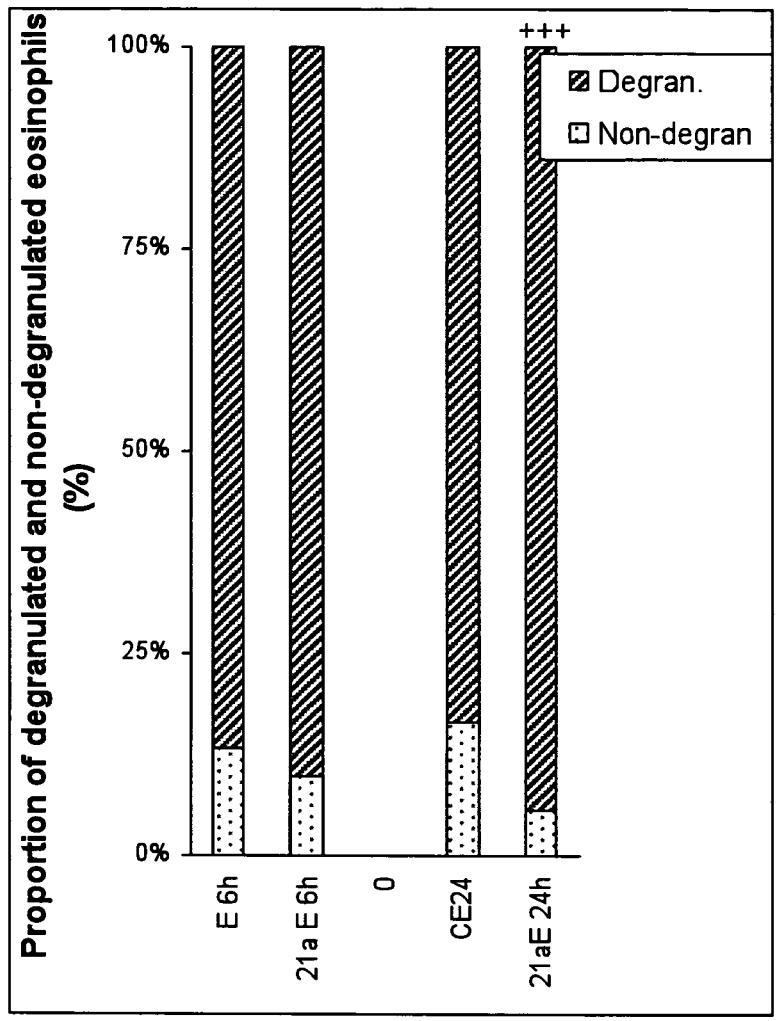

FIG. 58. Effect of plant decoction Le21a and estradiol-17β on the proportion of degranulated and non-degranulated uterine eosinophils. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test, +++, p<0.001; comparisons to animals treated with estradiol alone.

Figure 59:
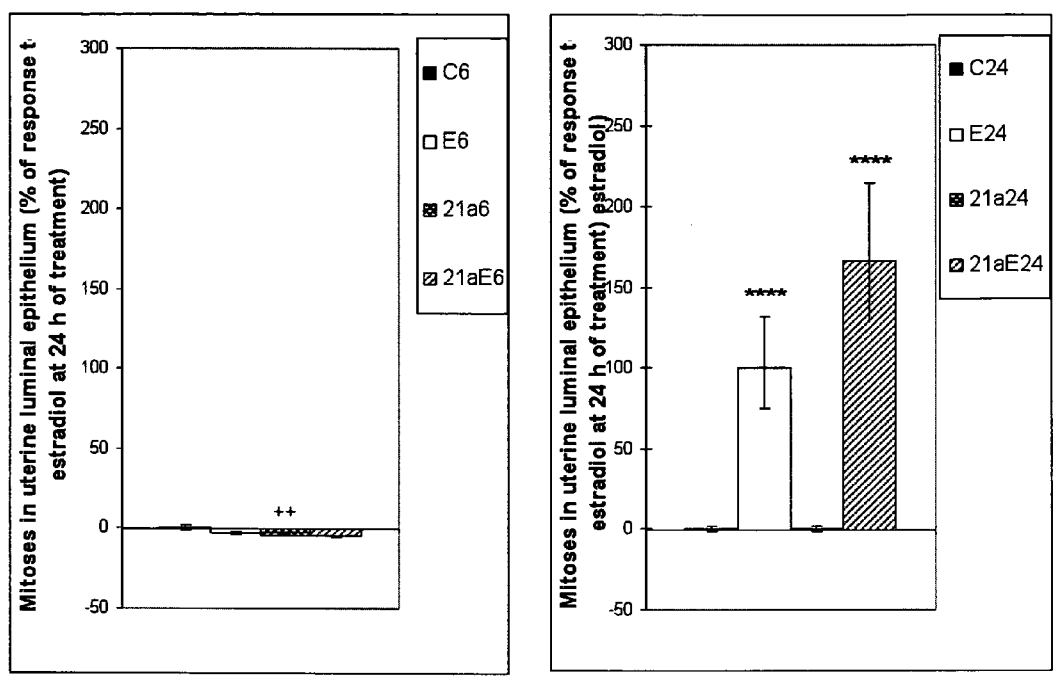

FIG. 59. Effect of plant decoction Le21a and/or estradiol on uterine luminal epithelial mitoses. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), ****p<0.0001, compared to the homologous condition without E treatment; ++p<0.01, compared to the homologous condition without pretreatment with the decoction Le21a.

Figure 60:
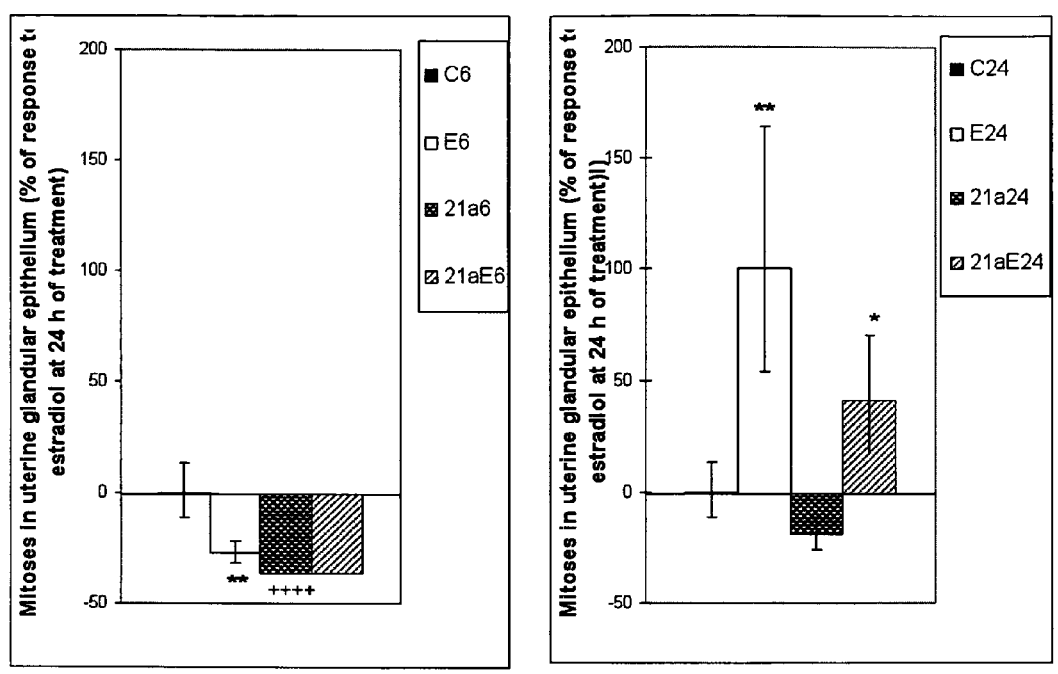

FIG. 60. Effect of plant decoction Le21a and/or estradiol on uterine glandular epithelium mitoses. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution:ethanol 9:1 as vehicle (C). The uteri were excised 6 h (E6, 21a6, 21aE6 or C6) or 24 h (E24, 21a24, 21aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.05, **p<0.01, compared to the homologous condition without E treatment; ++++p<0.0001, compared to the homologous condition without pretreatment with the decoction Le21a.

Figure 61:
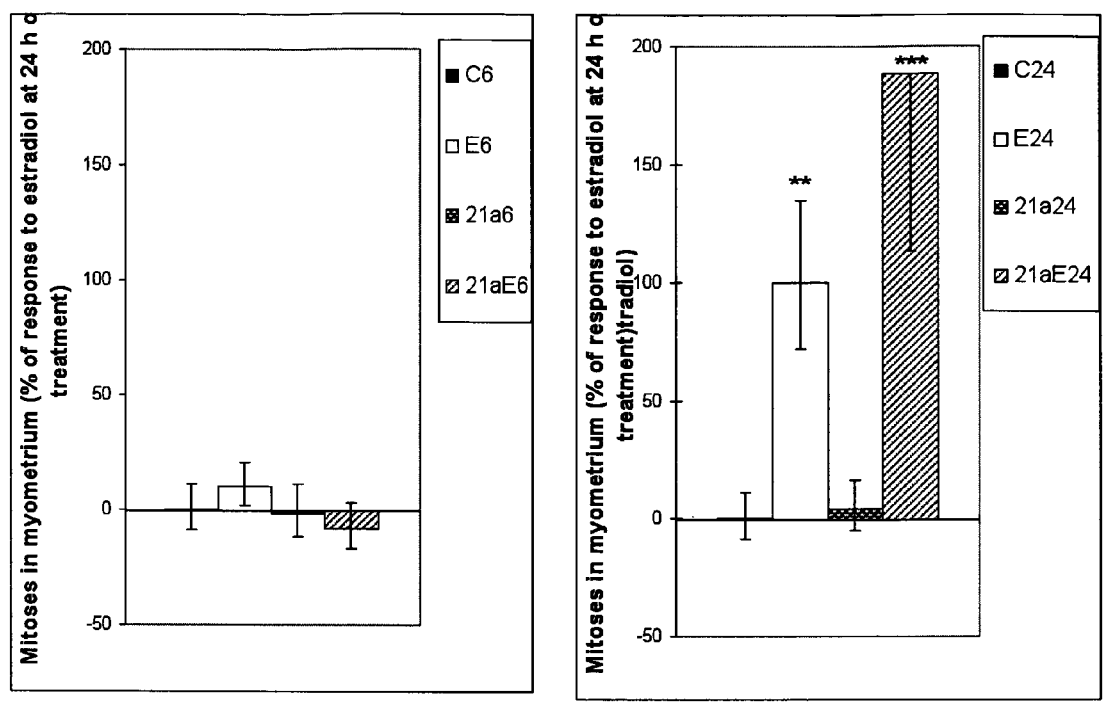

FIG. 61. Effect of plant decoction Le21a and/or estradiol on myometrium mitoses. Prepubertal rats received s.c. 0.33 mg estradiol-17β/kg b.wt (E), 6 mL of the decoction diluted 1:1 in absolute ethanol and then diluted in saline physiological solution 1:9)/kg b.wt. (21a), the decoction followed by estradiol 1 h later (21aE) or saline physiological solution: ethanol 9:1 as vehicle (C). The uteri were excised 6 h (E6, 21a6, 21aE6 or C6) or 24 h (E24, 21a24, 21aE24 or c24) after estradiol or vehicle administration, under anesthesia. Bars indicate means (expressed as % of response to estradiol at 24 h of treatment)±standard error of the mean. Statistics: Least significant difference a posteriori LSD test (LSD), p<0.01, *p<0.001, compared to the homologous condition without E treatment.

Figure 62:
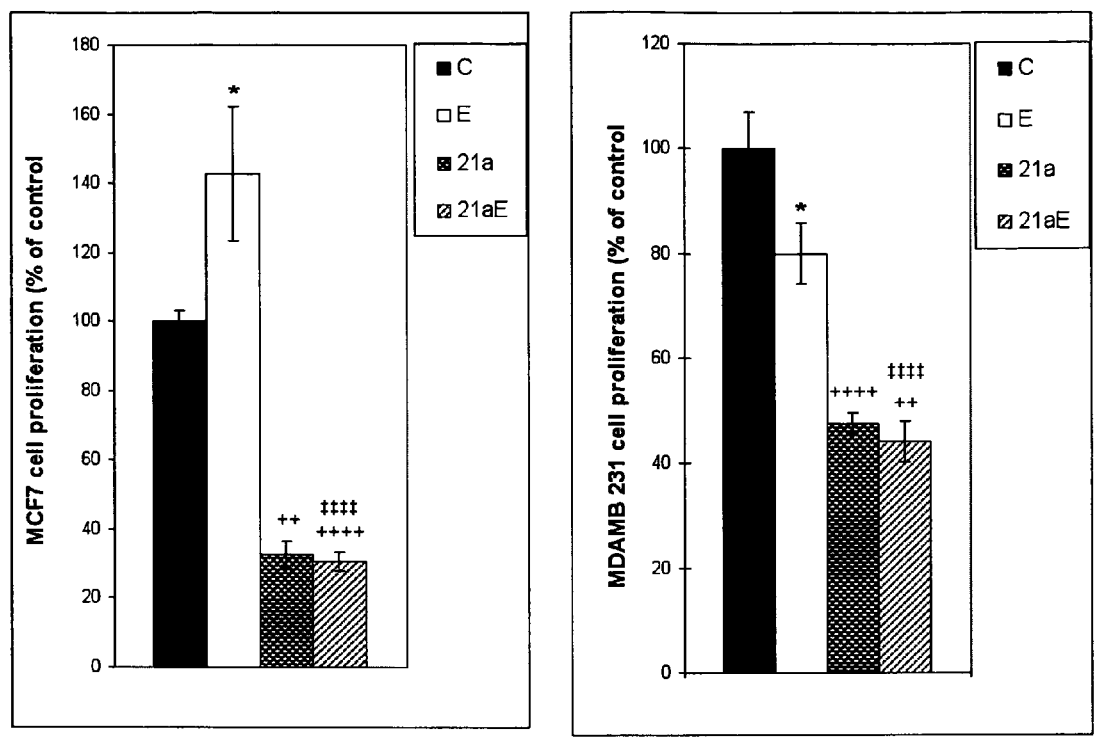

FIG. 62. Effect of plant decoction Le21a and/or estradiol-17β or both on cell proliferation of cultured human MCF-7 and MDAMB-231 mammary cancer cells. Estradiol (E), plant decoction (21a), plant decoction plus estradiol (21aE) or vehicle (C) was added to the culture media and number of cells was evaluated 72 h later. Bars indicate means (expressed as % of values in controls)±standard error of the mean. Statistics: Least significant difference a posteriori LSD test (LSD), *p<0.05, compared to the homologous condition without E treatment; ++p<0.01, ++++p<0.0001, compared to the homologous condition without pretreatment with the decoction Le21a; ‡‡‡‡p<0.0001, compared to controls without extract and estradiol. Collected February 2006, evaluated at 16 mo.

Figure 63:
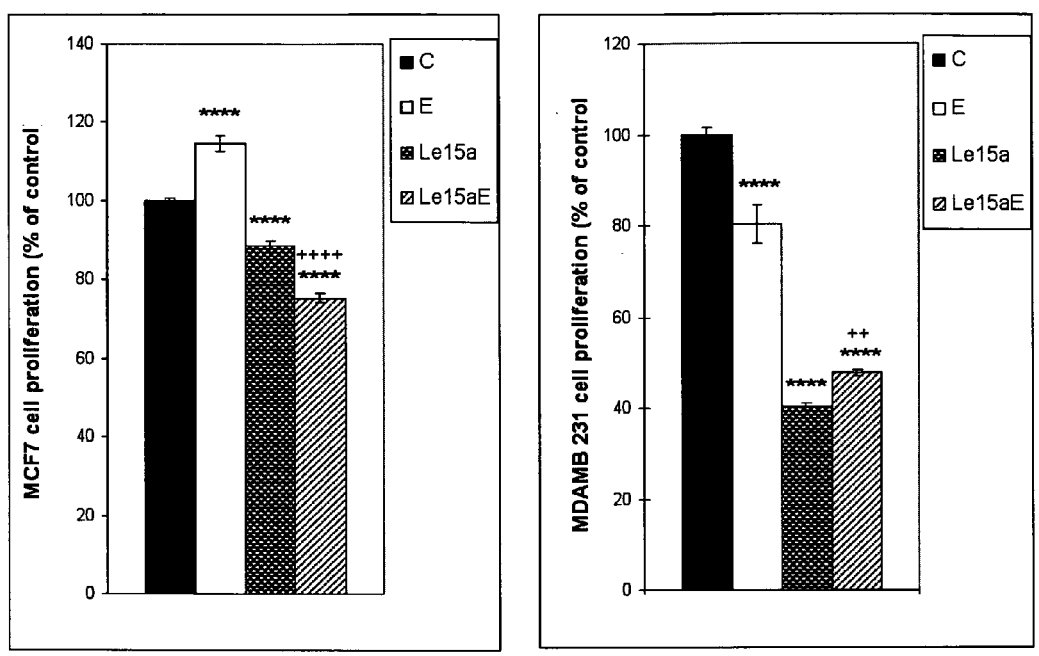

FIG. 63. Effect of plant "aged" decoction Le15a, estradiol-17β or both on cell proliferation of cultured human MCF-7 and MDAMB-231 mammary cancer cells. Estradiol (E), plant decoction (15a), plant decoction plus estradiol (15aE) or vehicle (C) was added to the culture media and number of cells was evaluated 72 h later. Bars indicate means (expressed as % of values in controls)±standard error of the mean. Statistics: Least significant difference a posteriori LSD test (LSD), *p<0.05, compared to the homologous condition without E treatment; +p<0.05, ++p<0.01, +++p<0.001, compared to the homologous condition without pretreatment with the plant decoction Le15a; ‡p<0.05, ‡‡‡‡p<0.0001, compared to controls without both extract and estradiol. Collected February 2006, evaluated at 24 mo.

Figure 64:
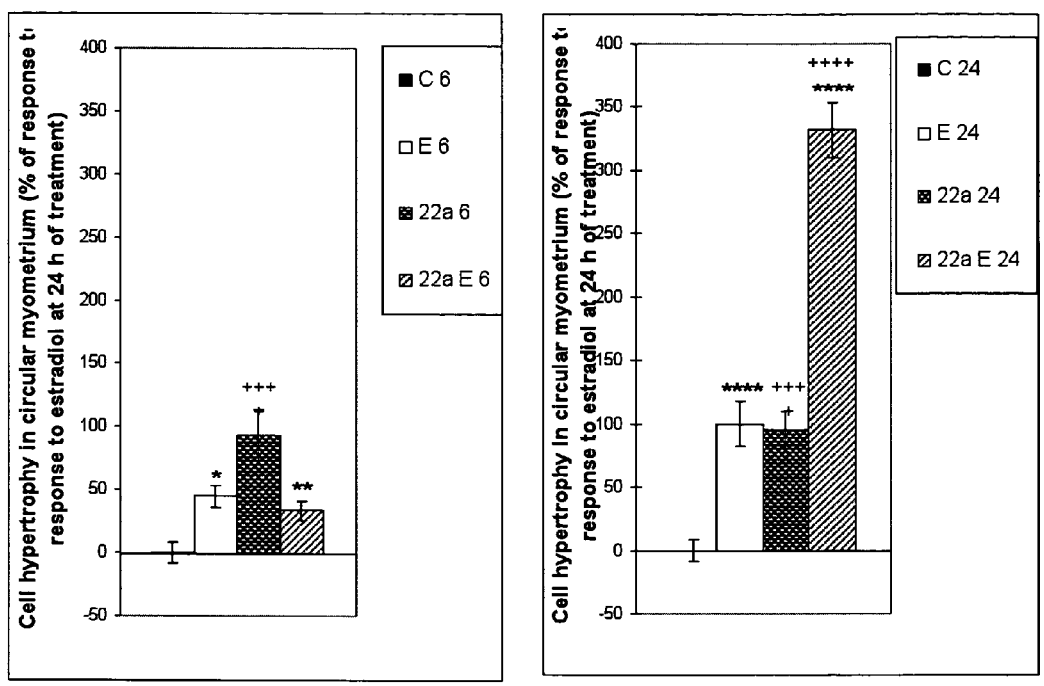

FIG. 64. Effect of plant extract Le22a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aF) or saline physiological solution:ethanol 9:1 as vehicle (C). The uteri were excised 6 h (E6, 22a6, 22aE6 or C) or 24 h (E24, 22a24, 22aE24 or C) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.05, p<0.01, **p<0.0001, compared to the homologous condition without E treatment; +++p>0.001, ++++p<0.0001, compared to the homologous condition without pretreatment with the extract Le22a.

Figure 65:
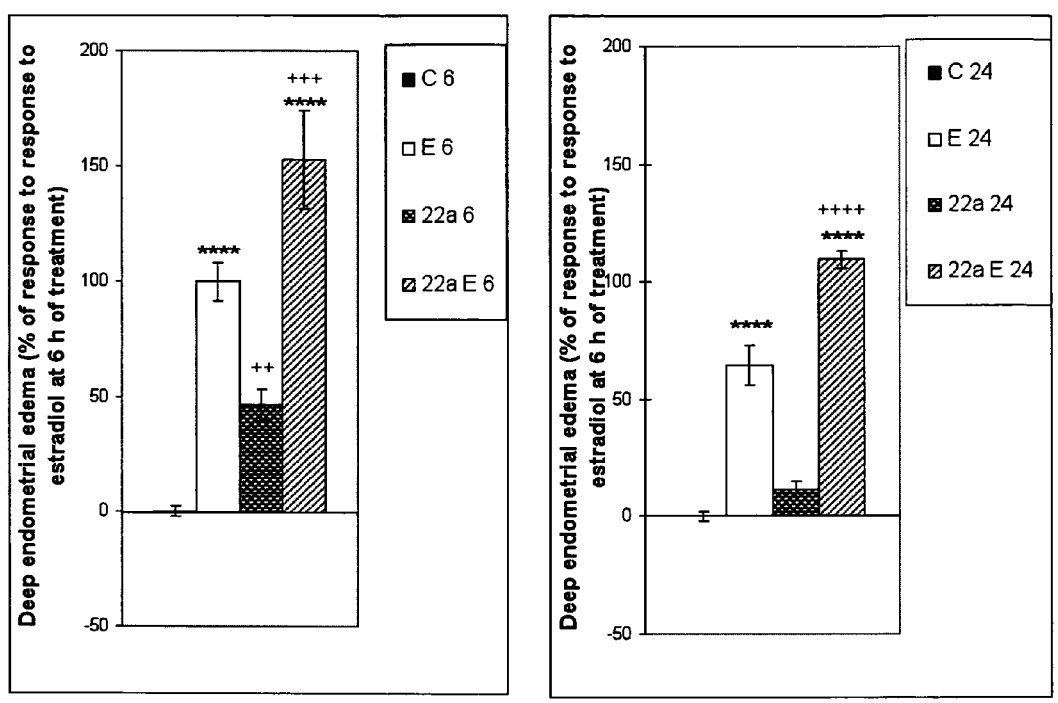

FIG. 65. Effect of plant extract Le22a and/or estradiol on deep endometrial stroma edema. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 6 h of treatment)±standard error of the mean. Statistics: Least significant difference a posteriori LSD test (LSD), ****p<0.0001, compared to the homologous condition without E treatment; ++p<0.01, +++p>0.001, ++++p<0.0001, compared to the homologous condition without pretreatment with the extract Le22a.

Figure 66:
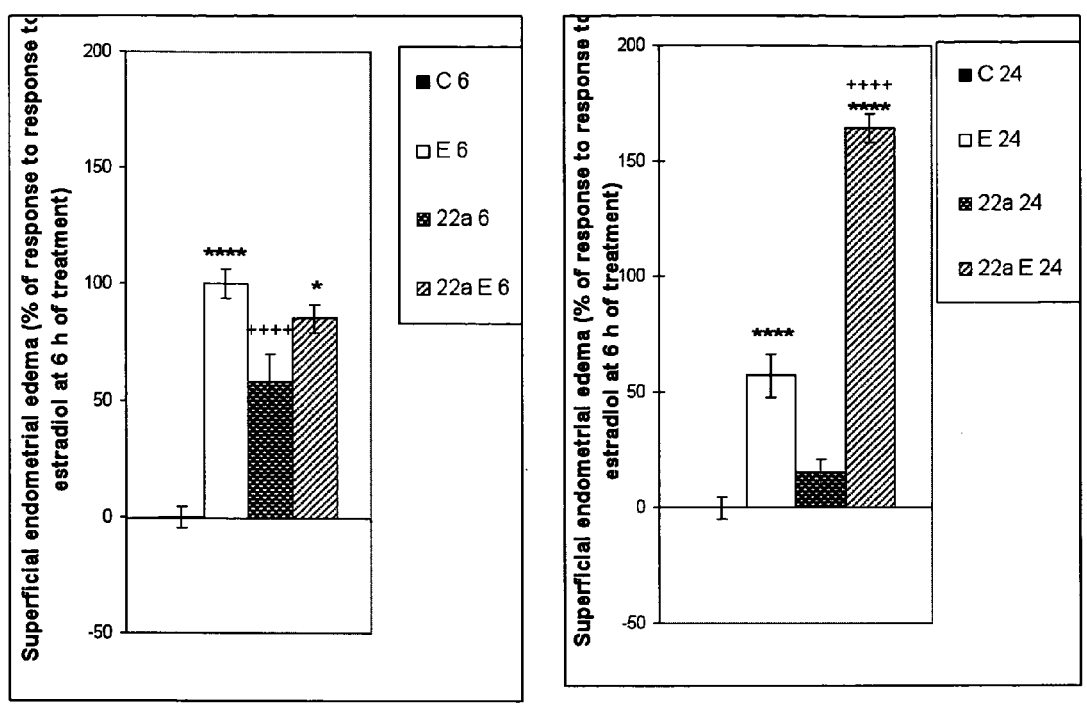
Figure 67:
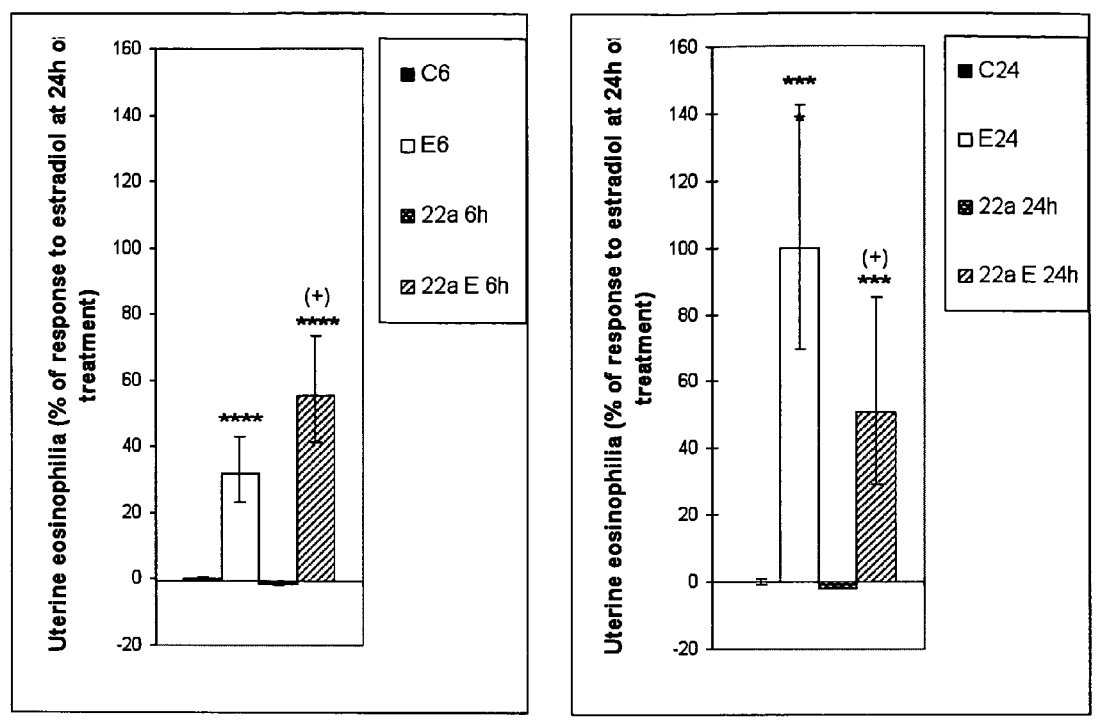

FIG. 66. Effect of plant extract Le22a and/or estradiol on superficial endometrial edema. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 6 h of treatment)±standard error of the mean. Statistics: Least significant difference a posteriori LSD test (LSD), *p<0.05, **p<0.0001, compared to the homologous condition without E treatment; ++++p<0.0001, compared to the homologous condition without pretreatment with the extract Le22a FIG. 67. Effect of plant extract Le22a and/or estradiol on uterine eosinophilia. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *p<0.001, ****p<0.0001, compared to the homologous condition without E treatment; (+)0.05<p<0.1, compared to the homologous condition without pretreatment with the extract Le22a.

Figure 68:
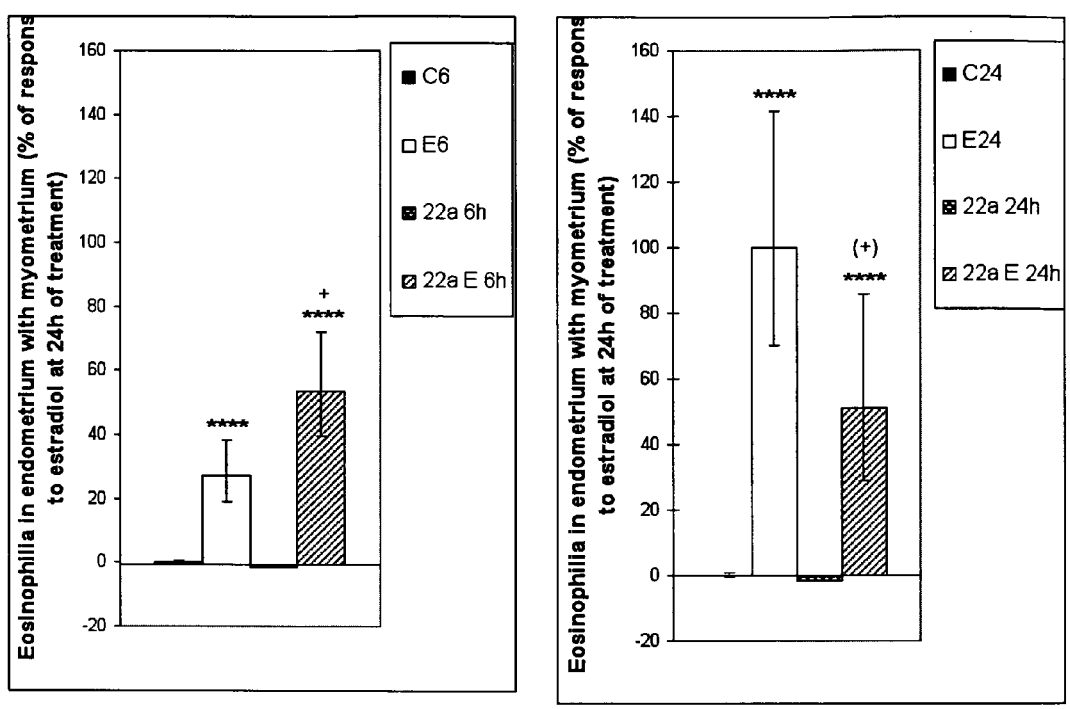

FIG. 68. Effect of plant extract Le22a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), ****p<0.0001, compared to the homologous condition without E treatment; (+)0.05<p<0.1; +p<0.05, compared to the homologous condition without pretreatment with the extract Le22a.

Figure 69:
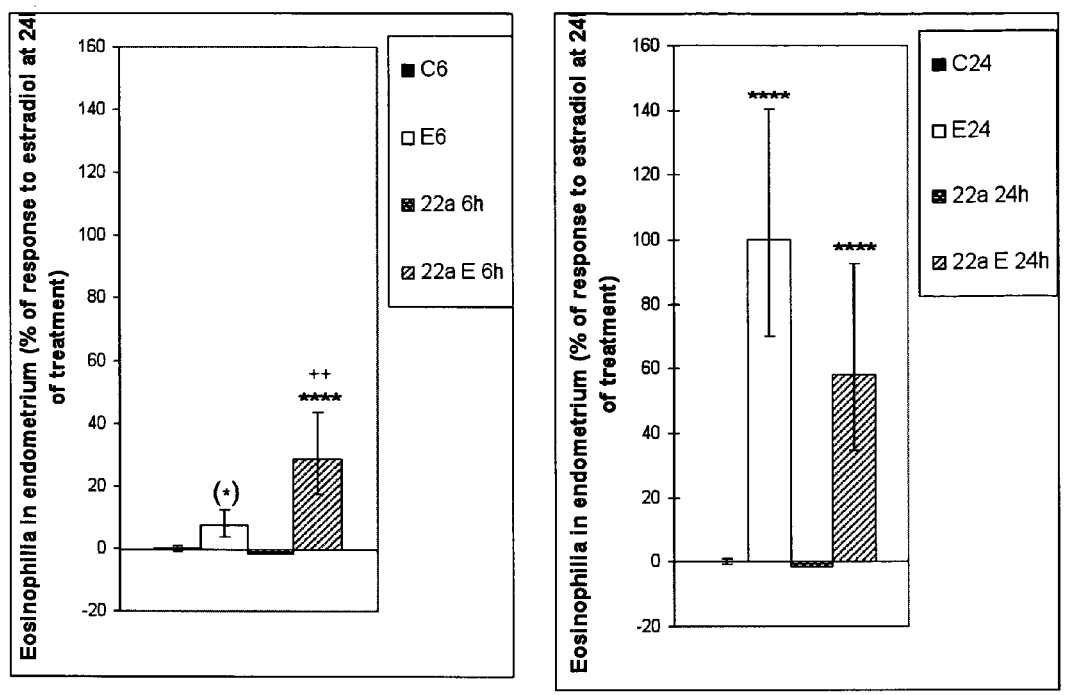

FIG. 69. Effect of plant extract Le22a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), ****$p<0.0001$, compared to the homologous condition without E treatment; (+)$0.05<p<0.1$, ++$p<0.01$, compared to the homologous condition without pretreatment with the extract Le22a.

Figure 70:
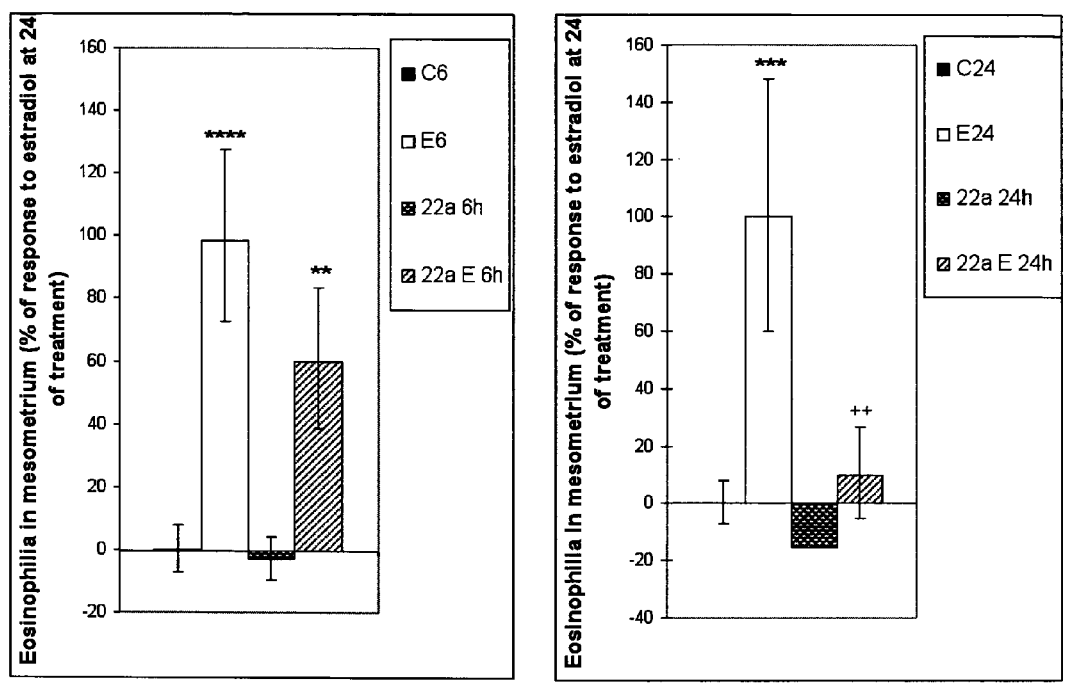

FIG. 70. Effect of plant extract Le22a and/or estradiol on cell hypertrophy in circular myometrium. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), $p<0.01$, *$p<0.001$, ****$p<0.0001$, compared to the homologous condition without E treatment; ++$p<0.01$, compared to the homologous condition without pretreatment with the extract Le22a.

Figure 71:
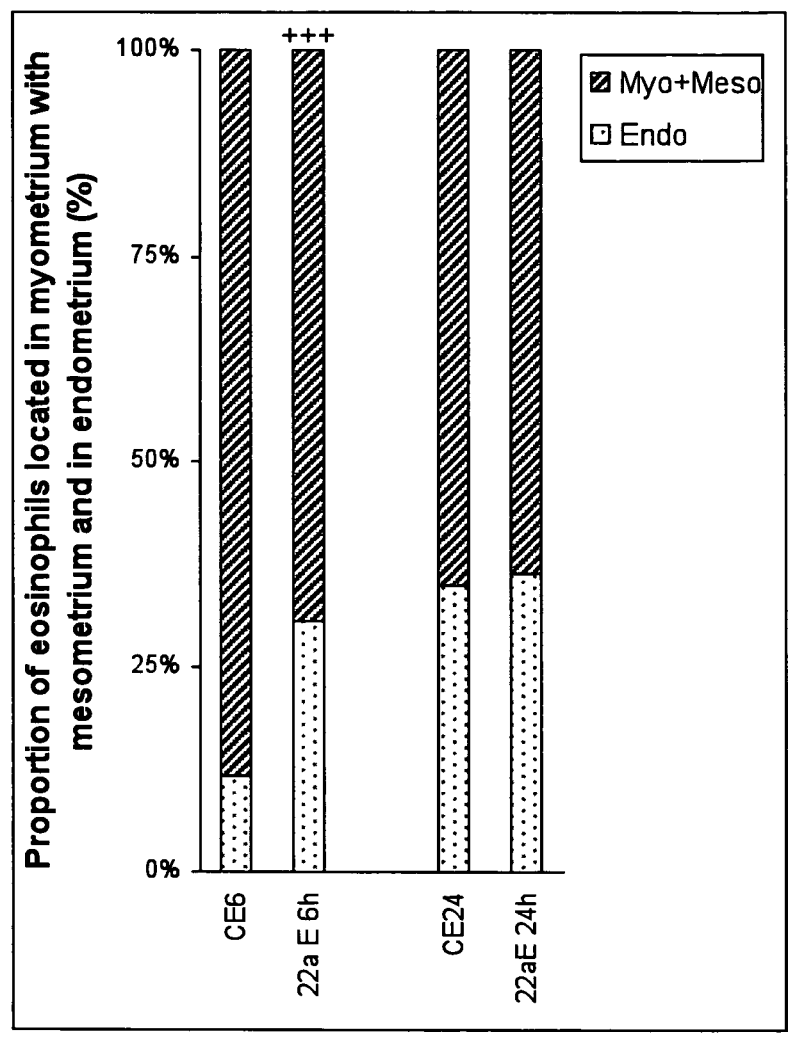

FIG. 71. Effect of plant extract Le22a and estradiol-17β on the proportion of uterine eosinophils located in the endometrium and in the myometrium with mesometrium. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +++, $p<0.001$; comparisons to animals treated with estradiol alone.

Figure 72:
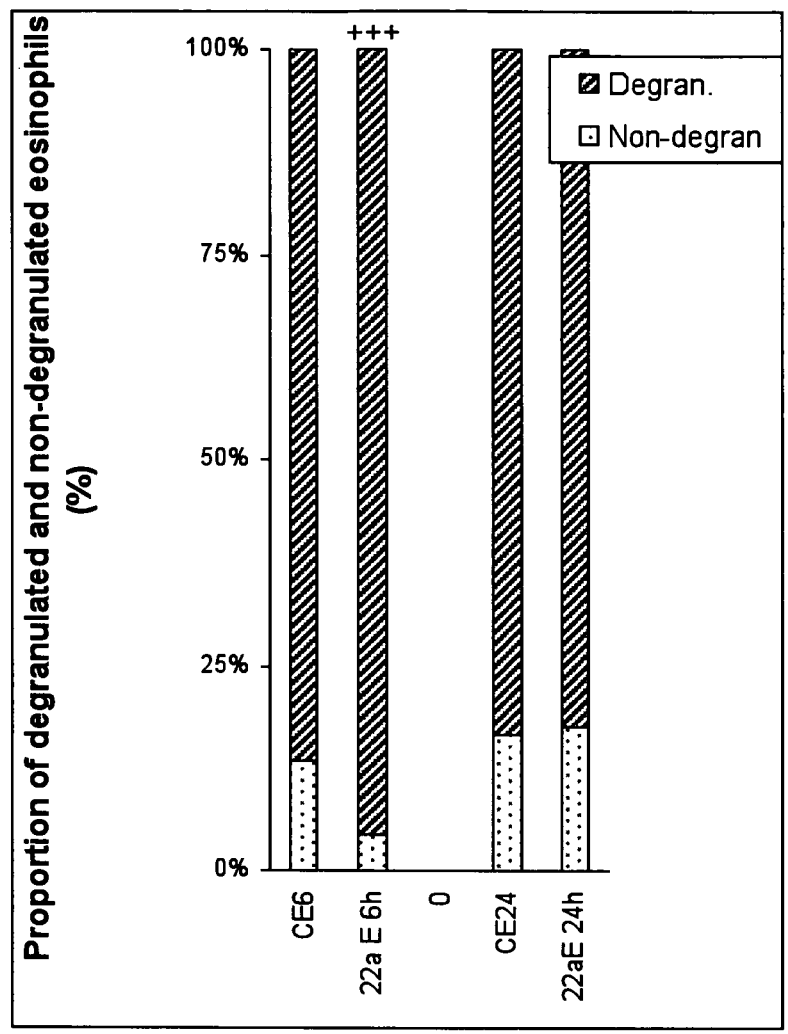

FIG. 72. Effect of plant extract Le22a and estradiol-17β on the proportion of degranulated and non-degranulated uterine eosinophils Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution: ethanol 9:1 as vehicle (C), and the uteri were excised 6 h or 24 h thereafter under anesthesia. The proportions in controls and in the extract alone are not shown because of the extremely low eosinophil numbers, that does not allow any statistical analysis. Statistics: $\chi^2$ test; +++, $p<0.001$; comparisons to animals treated with estradiol alone.

Figure 73:
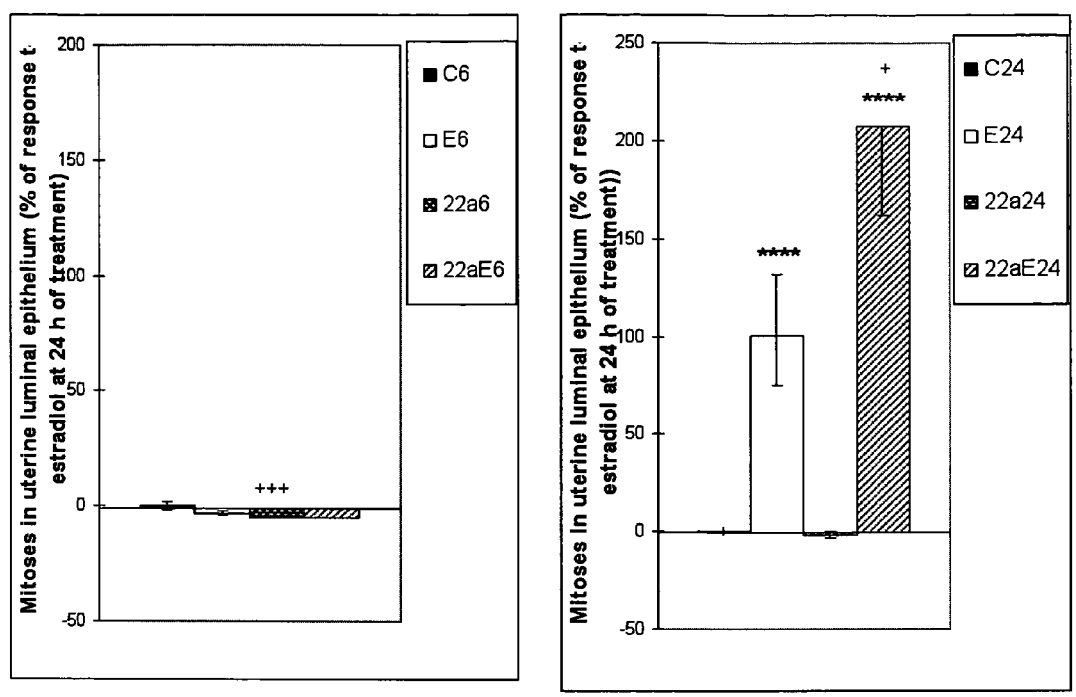

FIG. 73. Effect of plant extract Le22a and/or estradiol on uterine luminal epithelial mitoses. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), ****$p<0.0001$, compared to the homologous condition without E treatment; +$p<0.05$, +++$p>0.001$, compared to the homologous condition without pretreatment with the extract Le22a.

Figure 74:
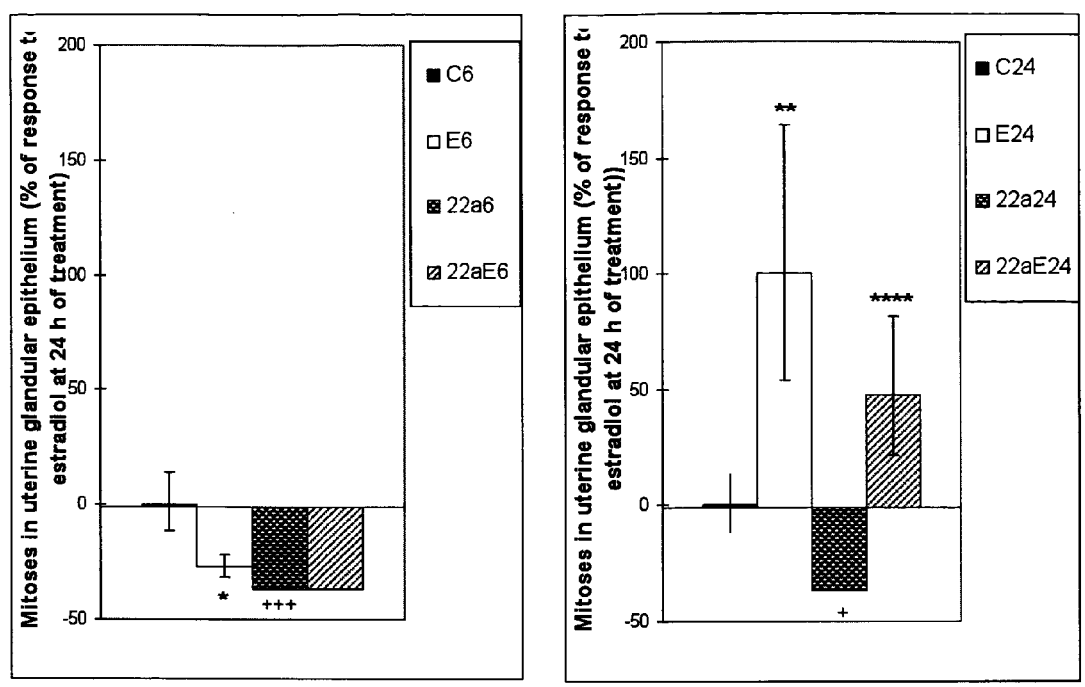

FIG. 74. Effect of plant extract Le22a and/or estradiol on uterine glandular epithelial mitoses. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), *$p<0.05$, $p<0.01$, **$p<0.0001$, compared to the homologous condition without E treatment; +$p<0.05$, +++$p>0.001$, compared to the homologous condition without pretreatment with the extract Le22a.

Figure 75:
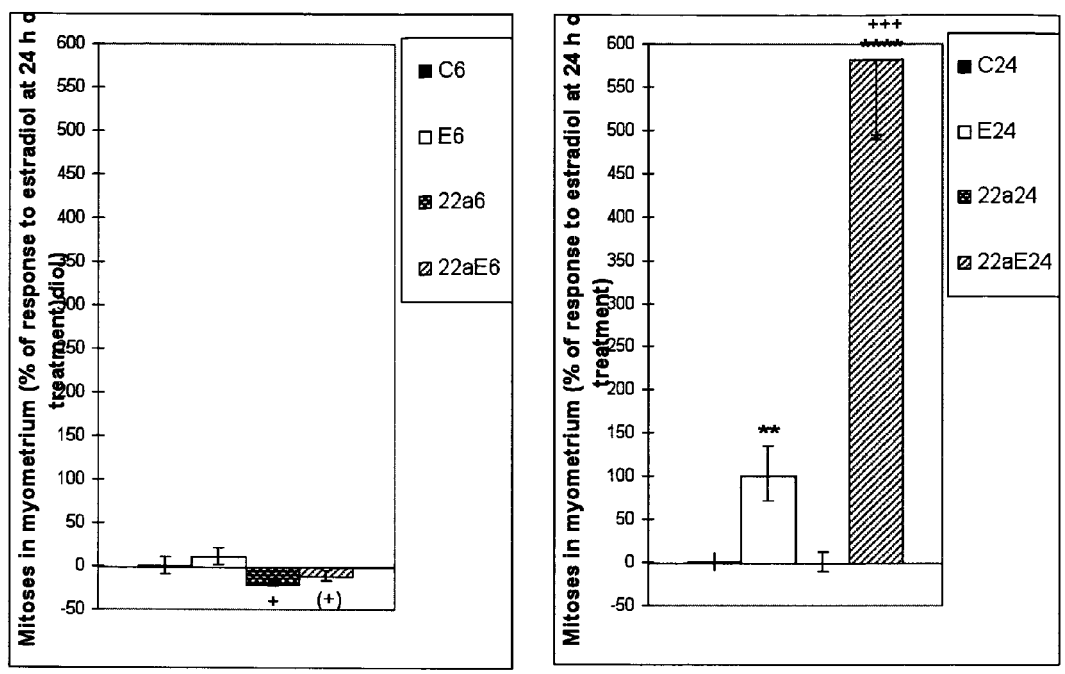

FIG. 75. Effect of plant extract Le22a and/or estradiol on myometrium mitoses. Prepubertal rats received s.c. 0.33 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 6 h (E6, 22a6, 22aE6 or C6) or 24 h (E24, 22a24, 22aE24 or C24) after estradiol or vehicle administration, under anesthesia. Bars indicate means (expressed as % of response to estradiol at 24 h of treatment)±standard error of the mean. Statistics: Least significant difference a posteriori LSD test (LSD), $p<0.01$, **$p<0.0001$, compared to the homologous condition without E treatment; (+)$0.05<p<0.1$, +$p<0.05$, +++$p>0.001$, compared to the homologous condition without pretreatment with the extract Le22a.

Figure 76:
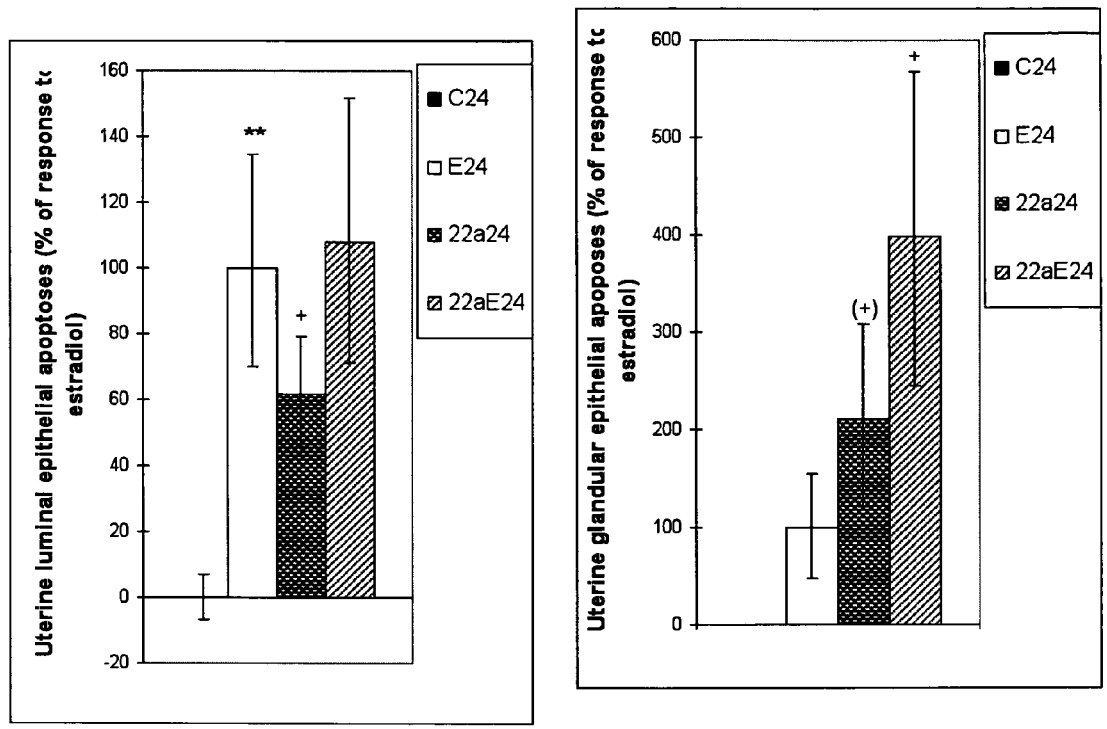
Figure 77:
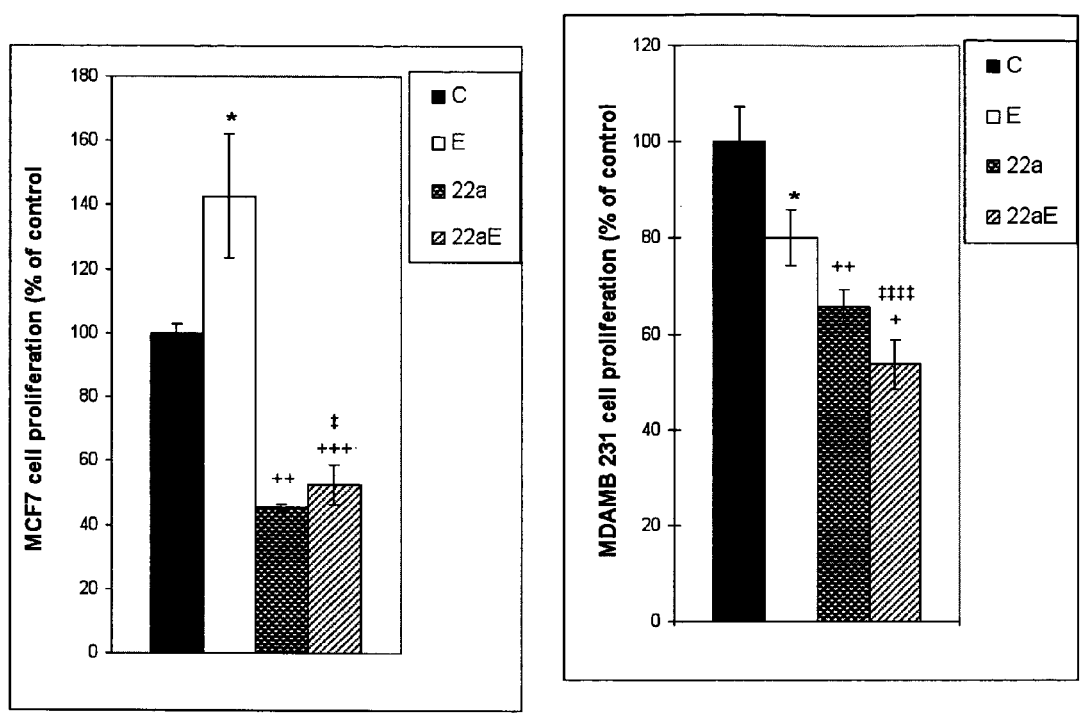

FIG. 76. Effect of plant extract Le22a and/or estradiol on uterine luminal epithelial and glandular epithelial apoptoses. Prepubertal rats received s.c. 0.3 mg estradiol-17β/kg b.wt (E), 6 mL of the extract diluted in saline physiological solution 1:9)/kg b.wt. (22a), the extract followed by estradiol 1 h later (22aE) or saline physiological solution:ethanol 9:1 as vehicle (C). The uteri were excised 24 h (E24, 22a24, 22aE24 or C24) after estradiol or vehicle administration, under anesthesia. Bars indicate means (expressed as % of response to estradiol)±standard error of the mean. Statistics: Least significant difference a posteriori LSD test (LSD), **$p<0.01$, compared to the homologous condition without E treatment; (+)$0.05<p<0.1$, +$p<0.05$, compared to the homologous condition without pretreatment with the extract Le22a FIG. 77. Effect of plant extract Le22a, estradiol-17β or both on cell proliferation of cultured human MCF-7 and MDAMB-231 mammary cancer cells. Estradiol (E), plant extract (22a), plant extract plus estradiol (22aE) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.05$, compared to the homologous condition without E treatment; +$p<0.05$, ++$p<0.01$, +++$p<0.001$, compared to the homologous condition without pretreatment with the extract Le22a; ‡$p<0.05$, ‡‡‡‡$p<0.0001$, compared to controls without both extract and estradiol.

Figure 78:
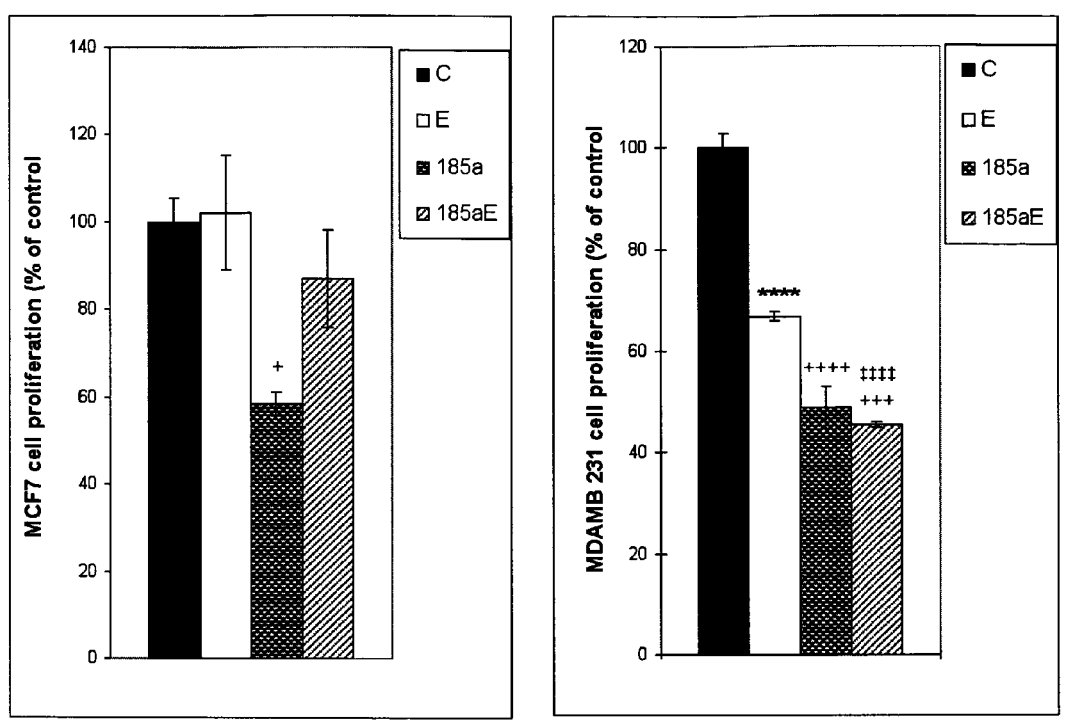
Figure 79:
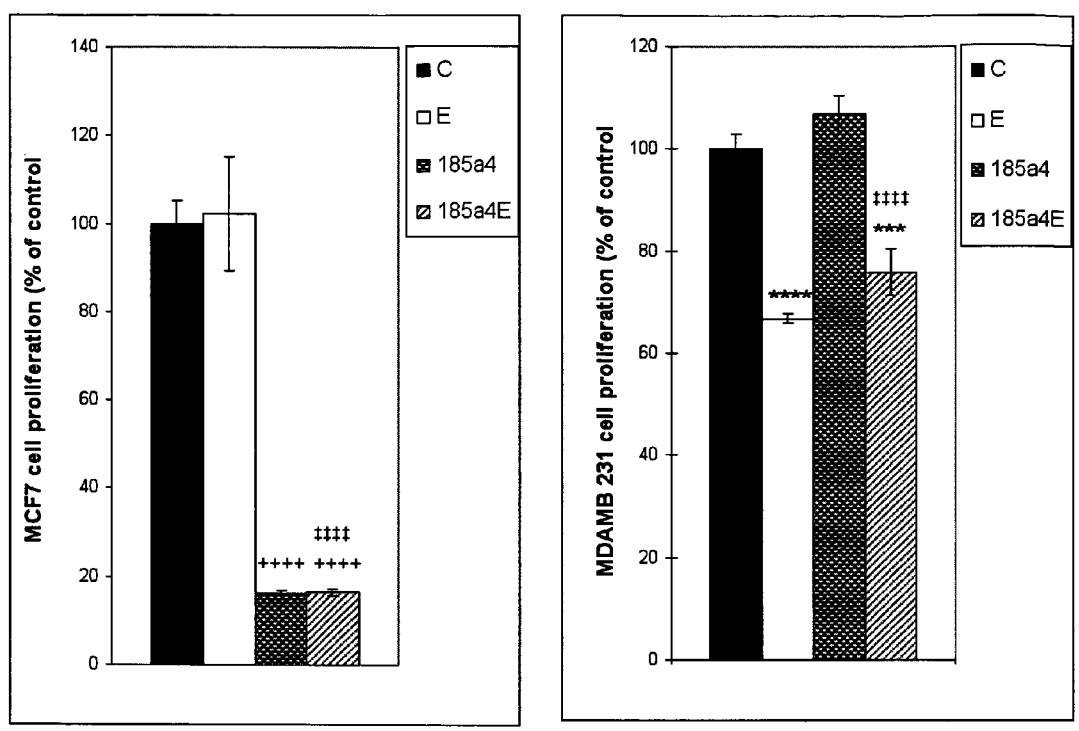
Figure 80:
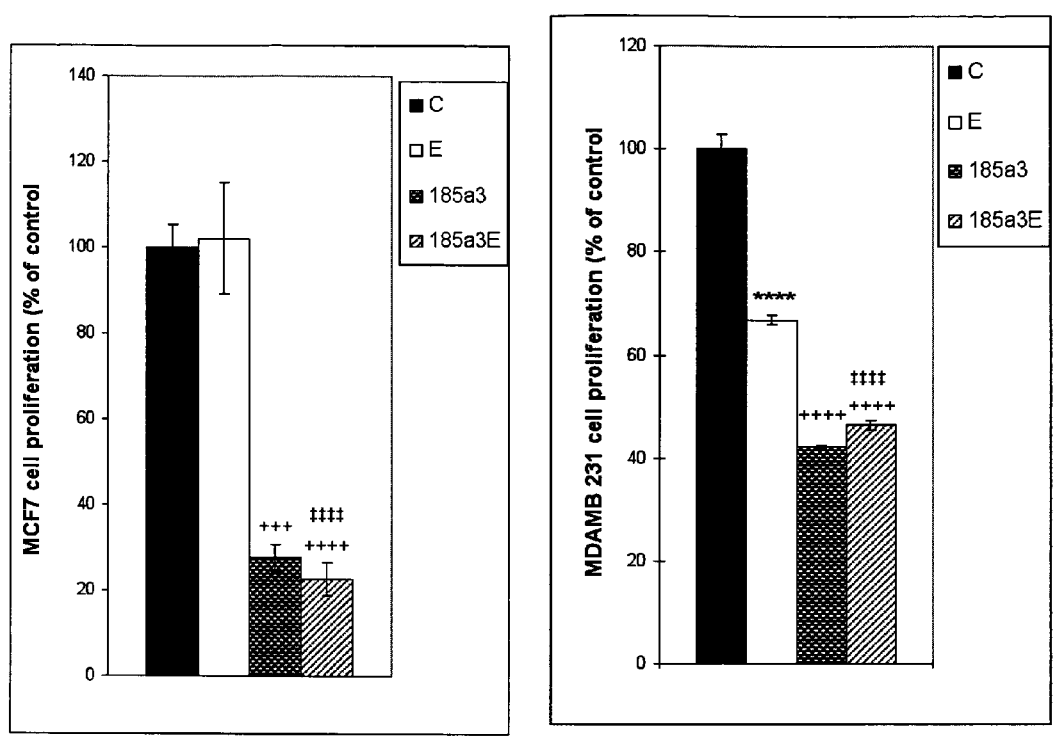
Figure 81:
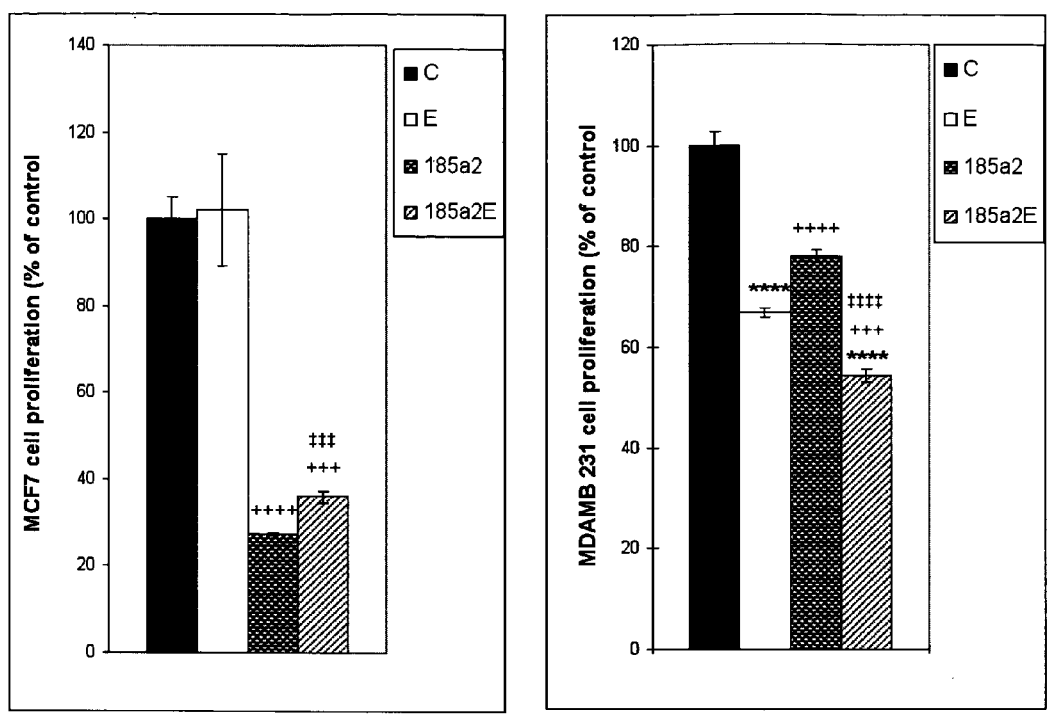
Figure 82:
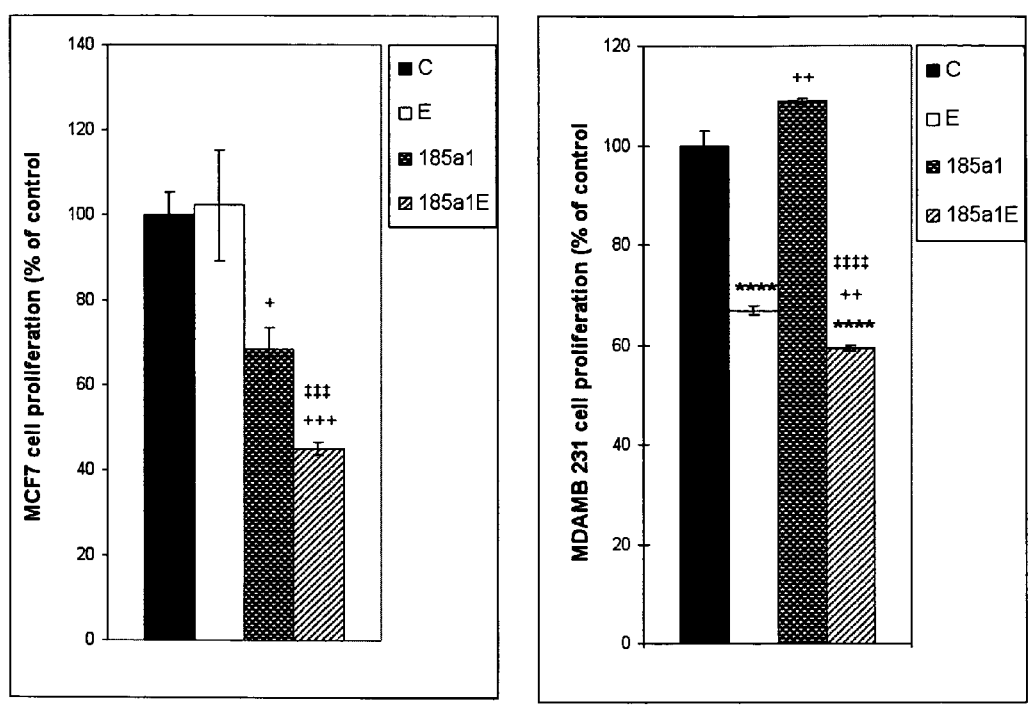
Figure 83:
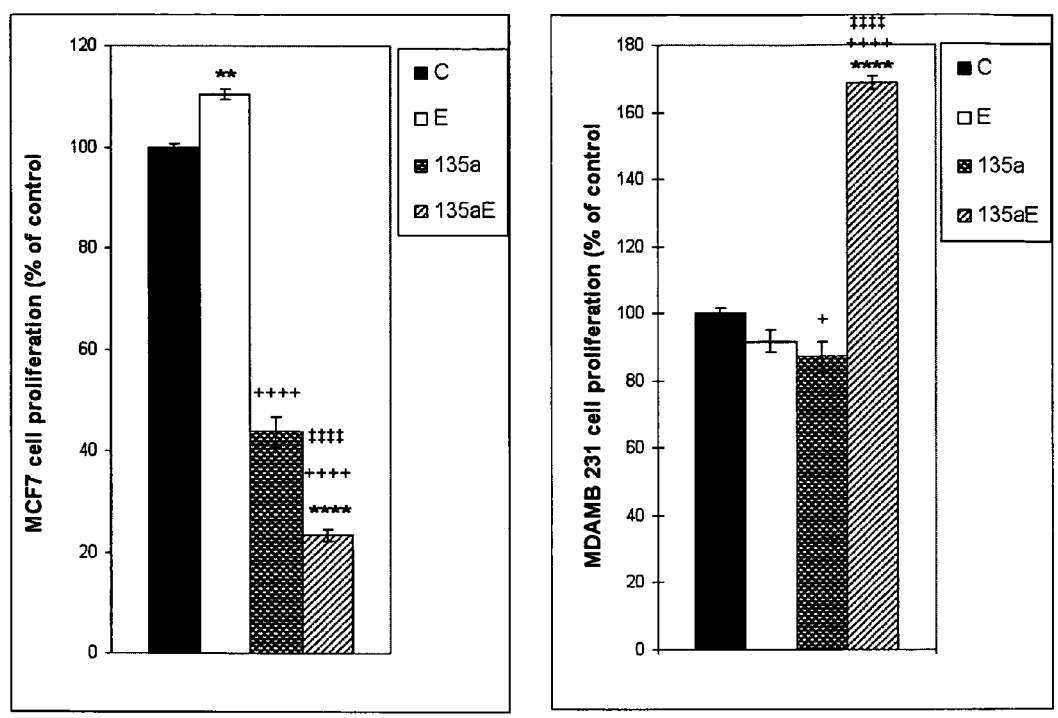

FIG. 78. Effect of plant extract Le185a and/or estradiol-17β on cell proliferation of cultured human MCF-7 and MDAMB-231 mammary cancer cells. Estradiol (E), plant extract (185a), plant extract plus estradiol (185aE) or vehicle (C) was added to the culture media and number of cells was evaluated 72 h later. Bars indicate means (expressed as % of values in controls)±standard error of the mean. Statistics: Least significant difference a posteriori LSD test (LSD), **$p<0.0001$, compared to the homologous condition without E treatment; +$p<0.05$, +++$p>0.001$, ++++$p<0.0001$, compared to the homologous condition without pretreatment with the extract Le185a; ‡‡‡‡$p<0.0001$, compared to controls without extract and estradiol FIG. 79. Effect of most polar plant extract fraction Le185a4 and/or estradiol-17β on cell proliferation of cultured human MCF-7 and MDAMB-231 mammary cancer cells. Estradiol (E), plant extract fraction (185a4), plant extract fraction plus estradiol (185a4E) or vehicle (C) was added to the culture media and number of cells was evaluated 72 h later. Bars indicate means (expressed as % of values in controls)±standard error of the mean. Statistics: Least significant difference a posteriori LSD test (LSD), *$p<0.001$, **$p<0.0001$, compared to the homologous condition without E treatment; ++++$p<0.0001$, compared to the homologous condition without pretreatment with the plant extract fraction Le185a4; ‡‡‡‡$p<0.0001$, compared to controls without extract and estradiol FIG. 80. Effect of plant extract fraction Le185a3 and/or estradiol-17β on cell proliferation of cultured human MCF-7 and MDAMB-231 mammary cancer cells. Estradiol (E), plant extract fraction (185a3), plant extract fraction plus estradiol (185a3E) or vehicle (C) was added to the culture media and number of cells was evaluated 72 h later. Bars indicate means (expressed as % of values in controls)±standard error of the mean. Statistics: Least significant difference a posteriori LSD test (LSD), $p<0.0001$, compared to the homologous condition without E treatment; +++$p>0.001$, ++++$p<0.001$, compared to the homologous condition without pretreatment with the plant extract fraction Le185a3; ‡‡‡‡$p<0.0001$, compared to controls without extract and estradiol FIG. 81. Effect of plant extract fraction Le185a2 and/or estradiol-17β on cell proliferation of cultured human MCF-7 and MDAMB-231 mammary cancer cells. Estradiol (E), plant extract fraction (185a2), plant extract fraction plus estradiol (185a2E) or vehicle (C) was added to the culture media and number of cells was evaluated 72 h later. Bars indicate means (expressed as % of values in controls)±standard error of the mean. Statistics: Least significant difference a posteriori LSD test (LSD), $p<0.0001$, compared to the homologous condition without E treatment; +++$p>0.001$, ++++$p<0.0001$, compared to the homologous condition without pretreatment with the plant extract fraction Le185a; ‡‡‡‡$p<0.0001$, compared to controls without extract and estradiol FIG. 82. Effect of plant extract fraction Le185a1 and/or estradiol-17β on cell proliferation of cultured human MCF-7 and MDAMB-231 mammary cancer cells. Estradiol (E), plant extract fraction (185a1), plant extract fraction plus estradiol (185a1E) or vehicle (C) was added to the culture media and number of cells was evaluated 72 h later. Bars indicate means (expressed as % of values in controls)±standard error of the mean. Statistics: Least significant difference a posteriori LSD test (LSD), $p<0.0001$, compared to the homologous condition without E treatment; +$p<0.05$, ++$p<0.01$, +++$p>0.001$, compared to the homologous condition without pretreatment with the plant extract fraction Le185a1; ‡‡‡$p<0.001$, ‡‡‡‡$p<0.0001$, compared to controls without extract and estradiol FIG. 83. Effect of plant extract Le135a (collected during mid-fall) and/or estradiol-17β on cell proliferation of cultured human MCF-7 and MDAMB-231 mammary cancer cells. Estradiol (E), plant extract (135a), plant extract plus estradiol (135a1E) or vehicle (C) was added to the culture media and number of cells was evaluated 72 h later. Bars indicate means (expressed as % of values in controls)±standard error of the mean. Statistics: Least significant difference a posteriori LSD test (LSD), $p<0.01$, ****$p<0.0001$, compared to the homologous condition without E treatment; +$p<0.05$, ++++$p>0.0001$, compared to the homologous condition without pretreatment with the plant extract Le135a1; ‡‡‡‡$p<0.0001$, compared to controls without extract and estradiol

DETAILED DESCRIPTION OF THE INVENTION

The invention is now described by means of examples. One skilled in the art would understand that various changes may be made without deviating from the spirit of this invention.

Example 1

Materials and Methods for Testing the Extracts on Animals

Prepubertal female rats were treated s.c. with the vehicle (C) (0.3 mL 1:9 ethanol saline), or a phytoestrogenic preparation, followed after one hour by estradiol-17β (E) Merck (0.33 mg/kg b.wt.), or its vehicle. Among the phytoestrogenic compounds used, genistein (G) Sigma (0.5 mg/kg b.wt.), two different concentrations of soybean ethanol extracts (S): 0.06 (Sd) and 0.364 (Sc) mg genistin/kg b.wt., and extracts, decoctions or extract sub-fractions of various plant species. Genistein quantification was based in the indirect valoration of genistein following 2M HCl hydrolysis and genistein quantification by HPLC (45, 46). Other ethanol extracts, decoctions and extract fractions from several plant species, as suggested by ethno-medicinal knowledge, were additionally assayed, from which only those displaying promising results for therapeutic applications are shown (vide infra). Uteri were excised under ether anesthesia and histologically processed for eosinophil quantification and morphometric analysis of different parameters of estrogen action (22, 34). The following parameters were quantified in the uterus: total uterine eosinophilia (6), percentage of eosinophils according to the distribution in different uterine histological layers and to their degree of degranulation (10, 14); deep endometrial and superficial endometrial edema (47); luminal epithelial, glandular epithelial (34) and myometrial (47) cell hypertrophy, luminal epithelial RNA content (34), and number of mitotic figures for each uterine cell-type.

Additionally to above procedure, the most promising extracts were immunohistochemically assayed for their effect on uterine phosphorylated alpha estrogen receptors and beta estrogen receptors (ER). The following antibodies were used for detection of phosphorylated alpha and beta ERs: Goat polyclonal anti P-αER (Santa Cruz Biotechnology), goat polyclonal anti P-βER (Santa Cruz Biotechnology), donkey anti goat (Jackson Immuno Research), donkey anti-rabbit (Jackson Immuno Research). For detection, vectastain ABC kit (Vector Laboratories) and DAB peroxidase substrate kit (Vector Laboratories).

Cell lines. The experimental cell cultures were obtained from American Type Culture Collection (Rockville, Md., USA). MCF-7 and MDA-MB231 cells (estrogen receptor positive and negative respectively breast cancer cells) were grown in Dulbecco's modified Eagle's medium (DMEM) containing 10% FCS, 100 U/ml penicillin, 100 μg/ml streptomycin and 1 mM glutamine. Cells were seeded into 96 well microtiter plates in 100 μl at plating density of $3 \times 10^3$ cells/well. After 24 h incubation at 37° C. under a humidified 5% carbon dioxide to allow cell attachment, the cells were washed with phenol red-free and the medium was changed to phenol red-free DMEM supplemented with 4% dextran-charcoal-stripped foetal calf serum (DCFCS). Then the cells were treated with different concentrations of drugs and incubated for 72 h under the same conditions. Stock solution of compounds was prepared in ethanol and the final concentration of this solvent was kept constant at 1%. Control cultures received 1% ethanol alone.

In vitro growth inhibition assay. The sulforhodamine B assay was used according to the method of Skehan et al. 1990 (48) with some modifications (49). Briefly, the cells were set up $3\times10^3$ cells per well of a 96-well, flat-bottomed 200 μl microplate. Cells were incubated at 37° C. in a humidified 5% $CO_2$/95% air mixture and treated with the compounds at different concentrations for 72 hours. At the end of drug exposure, cells were fixed with 50% trichloroacetic acid at 4° C. After washing with water, cells were stained with 0.4% sulforhodamine B (Sigma-Aldrich, St. Louis, Mo.), dissolved in 1% acetic acid (50 μl/well) for 30 min, and subsequently washed with 1% acetic acid to remove unbound stain. Protein-bound stain was solubilized with 100 μl of 10 mM unbuffered Tris base, and the cell density was determined using a fluorescence plate reader (wavelength 540 nm). Values shown are the mean±SD of three independent experiments in triplicate.

Statistics: According to previous studies (14) using the Tukey test of additivity (50), data on some parameters of estrogen stimulation needs to be submitted to logarithmic transformation or to square or cubic root transformation to normalize distribution. Accordingly, the transformations were performed on some of the parameters of estrogen stimulation investigated (14). Transformed and non-transformed data were subjected to further statistical analysis.

Since multiple comparisons were performed between the different experimental conditions, transformed and non-transformed data (all parameters except eosinophil degranulation and eosinophil distribution between uterine tissue layers) were subjected to the least significant difference a posteriori (LSD) test. The common variance needed for this test was estimated from a one-way unbalanced analysis of variance (ANOVA).

In uterine eosinophil degranulation and distribution studies, the $\chi^2$ statistic was used to evaluate differences between the proportions.

Example 2

Plant Extracts

Plant extracts used were obtained by extracting specified plant material with absolute ethanol Merck for 72 hours at room temperature (20-25° C.) in dark bottles protected from the sunlight. In addition, other methods of plant extractions were performed, including extractions with solvents of different polarity, and various extract fractions were obtained. The decoctions were made in distilled water, boiling plant material for 20 minutes; following cooling of the extract it was mixed 1:1 in absolute ethanol.

*Calceolaria filicaulis* Clos ssp *luxurians* (Witasek) C. Ehrhart—Extract (Le81a)

Genus *Calceolaria* (Scrophulariaceae) in Chile is represented by approximately fifty species [2], some of which are used as stomachic drugs, sweetening agents and against bacterial infections.

*Calceolaria filicaulis* is a native Chilean plant belonging to the family Schrophulariaceae. The genus *Calceolaria* has about fifty species and some of them have been traditionally used for therapeutic purposes (such as curing stomach ache) or as a sweetening agent and against bacterial infections. The genus is known to be rich in diterpenes. (ref. Garbarino et al. 2006, J. Chilean Chem. Soc. 51 (4): 1057-1058). *Cakeloaria filicaulis* has flat rosette of broad mid green leaves and yellow lady's slipper like flowers. The extract of *Calceolaria* was called Le81a and extracted from aerial parts of the pants, including flowers (28 g of plant in 100 ml 100% ethanol).

Other *Calceolaria* species, such as *Calceolaris biflora* can also be used for obtaining an extract with similar effect as the described extract.

*Adesmia verrucosa* Meyen—Extract (Le179a)

*Adesmia verrucosa* is a native Chilean plant belonging to the family Papilionaceae. The genus *Adesmia* has about 240 species. Many *Adesmia* species are traditionally used for their analgesic and anti-inflammatory properties, in folk medicine. *Adesmia verrucosa* is a 1 m high resinous ramous perennial shrub with very small leaves virtually covering and surrounding small branches, and small yellow flowers displaying the typical shape of the Papilionaceae family species.

The plant extract was prepared from the aerial parts of the plant. 48.1 grams of aerial plant material, including flowers, was extracted in 50 ml of 100% ethanol at room temperature for 72 hours.

Other *Adesmia* species are also suitable for preparing extract with similar effects as the described extract. Such other species include *Adesmia verrucosa, A. atacamensis, A. boronoides, A. longipes, A. emarginata, A. confusa, A. balsamica, A. loudonia, A. phylloidea. A. pungens, A. radicifolia, A. resinosa.*

*Fuchsia magellanica* Extract (Le22a, Le135a, Le185a, and Decoctions Le21a and Le15a

*Fuchsia magellanica* is a native Chilean plant belonging to the family Onagraceae (Oenotheraceae). The genus *Fuchsia* has about 110 species. *Fuchsia magellanica* is a 1 to 3 m high caducifolius shrub with thin lanceolate leaves with a reddish color central nerve, and pendulous "eardrop" flowers with red sepals and purple or purple-blue petals. The fruit is a small epigenous berry. Decoctions of leaves and flowers are used in traditional medicine for their antipyretic and menstruation flux increasing effects effects. Their effect facilitating menstruation was attributed to their content in flavonoids and anthocyanines, which improve capillary fragility and permeability, the activity of these glycosides may also protect vascular wall collagen from their degradation by proteolytic enzymes, decreasing vascular fragility. The following compounds were obtained from *Fuchsia magellanica*: pelargonidine, peonidine, delfinidine, petonidine, cianidine, and acilated anthocyanines. Flowers contained flavonols and flavones, and leaves contained quercetin, apigenine, luteoline and kaempferol glycosides (ref. Muñoz O., Montes M., Wilkomirsky T. (2004) Monografóias—Plantas Medicinales de Uso en Chile. Química y Farmacología. Editorial Universitaria, pp. 125-127).

Extracts and decoctions were prepared from flowering aerial parts. Ethanol extract Le22a was obtained by extracting 160 g of plant material in 160 ml 100% ethanol for 72 hours. Extract Le135a was obtained by extracting 100 g plant material in 100 ml of 100% ethanol for 72 hours. Decoctions Le21a and Le15a were obtained by decoction for 10 minutes in distilled water and subsequent dilution in absolute ethanol resulting in 0.9 g plant in 1 ml 55% ethanol.

Extract Le185a was further partitioned by polarity from most apolar to most polar, respectively: Le185a2, Le185a3, Le185a4.

Example 3

Genistein and Soy Bean Extracts

Agonist Action

Figure 4:
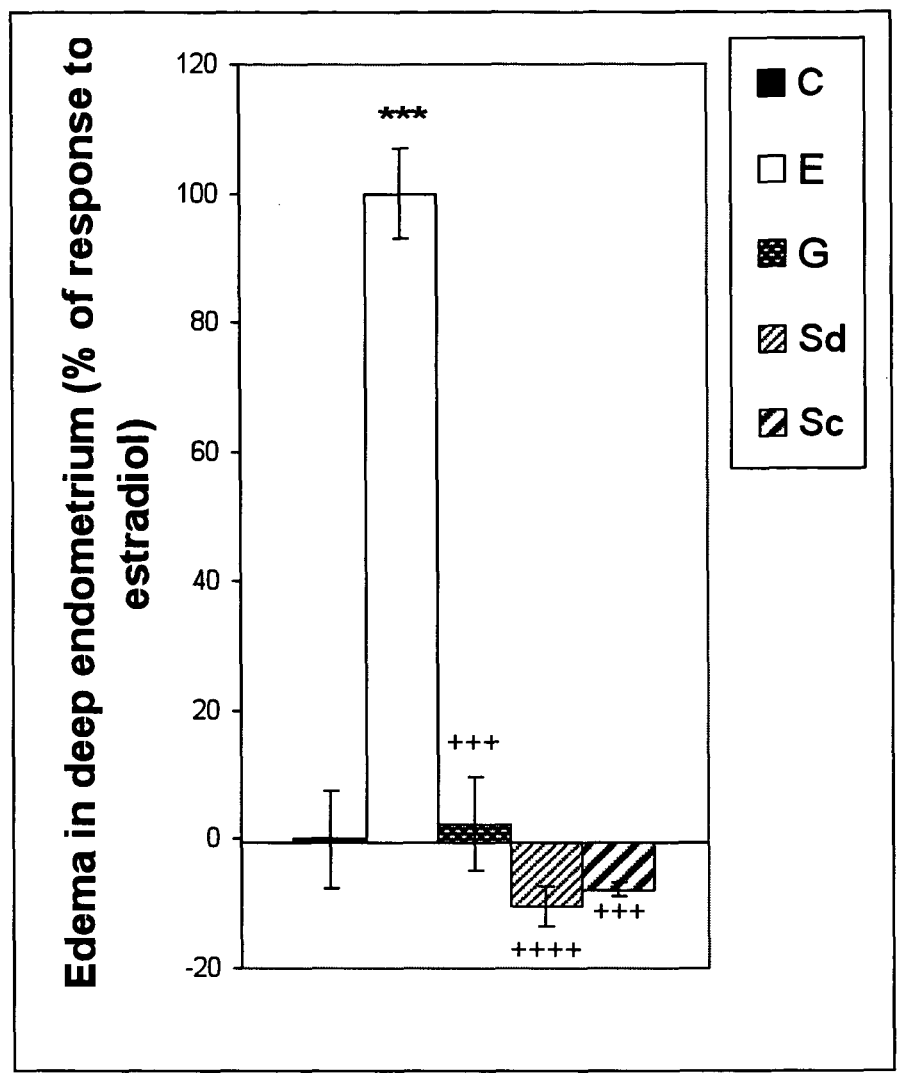

Myometrial hypertrophy was induced by E, G and two concentrations of S; G and Sc produced a response similar to E, while Sd induced a weaker response than that obtained with E (FIG. 1). Endometrial luminal epithelial cell hypertrophy (FIG. 2) and RNA content (FIG. 3) was induced by E, G Sd and Sc, although a response similar to E was achieved by G only; the responses to Sd and Sc were significantly weaker than that to E. Edema in deep endometrial stroma was induced by E only (FIG. 4). A normal intensity estrogen-induced uterine eosinophilia was observed following E treatment only, although a very slight but statistically significant response was also observed with Sd (FIG. 5). As compared to E-treated animals where most uterine eosinophils were located in endometrium with myometrium, in S treated animals there were more eosinophils in the mesometrium than in endometrium with myometrium, and following G treatment all the eosinophils were in the mesometrium (FIG. 6). Eosinophil degranulation induced by estrogens was significantly weaker with Sd as compared to E (FIG. 7). Uterine cell proliferation, evaluated as increase in the number of mitotic figures 24 h after treatment, was induced in uterine luminal epithelium (FIG. 8), uterine glandular epithelium (FIG. 9), endometrial stroma (FIG. 10) and myometrium (FIG. 11) by E only, but not by G, Sd or Sc. FIG. 12 compares the estrogenic activity of estradiol to that of genistein for the various parameters of estrogen action in the uterus.

Figure 14:
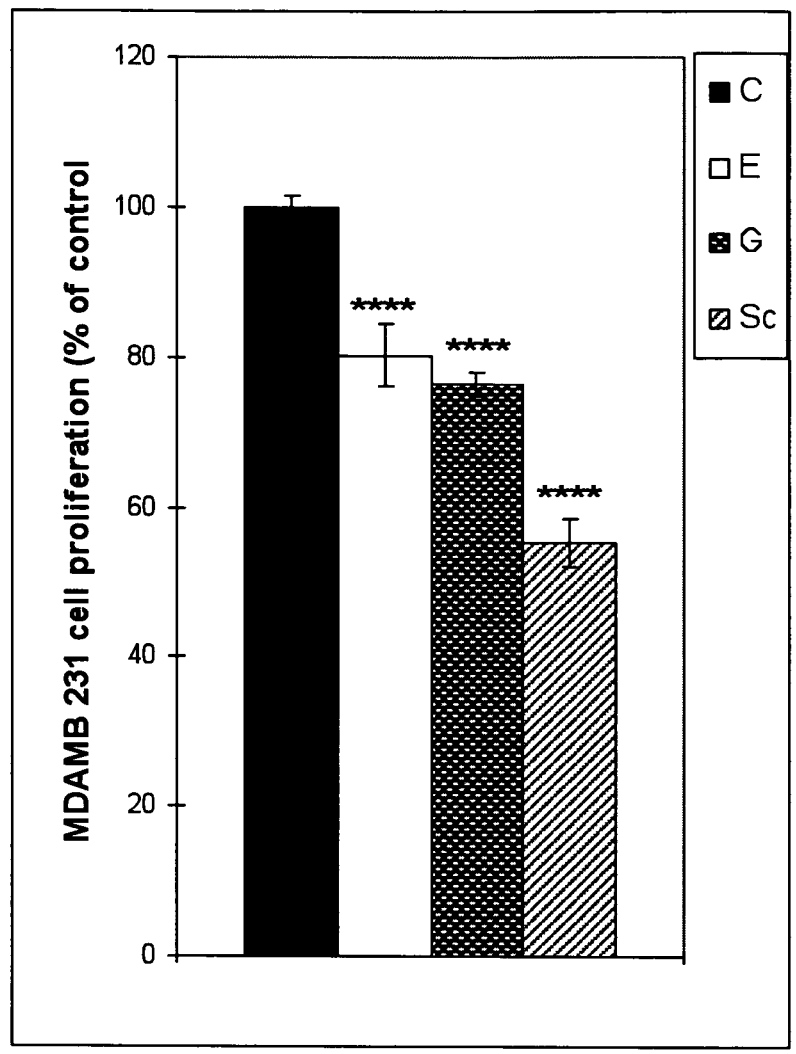

Proliferation of cultured human mammary cancer MCF-7 cells increased under the action of estradiol-17, genistein, or Sc. Estradiol and genistein were similar in their potency to stimulate tumor cell proliferation, and Sc was more potent than estradiol or genistein to induce MCF-7 cells proliferation (FIG. 13). On the contrary, proliferation of cultured human mammary cancer MDAMB-231 cells was slightly inhibited by estradiol or genistein, and the inhibition was more pronounced under the effect of Sc. (FIG. 14).

Estrogen-Antagonist Action

Genistein antagonizes estrogen-induced endometrial edema at 6 but not at 24 h of treatment (FIG. 15) and uterine eosinophilia, mainly at 6 h of treatment (FIG. 16); the decrease in eosinophils under estrogen treatment is stronger if only endometrial layer is considered (FIG. 17); which effect that is reflected in a decrease in the proportion of eosinophils located in endometrium with myometrium, as compared to those located in mesometrium (FIG. 18); and also decreases the degranulation of uterine eosinophils (FIG. 19). Further, genistein almost completely block estrogen-induced cell proliferation in uterine luminal epithelium (FIG. 20), endometrial stroma (FIG. 21) and myometrium (FIG. 22).

Figure 24:
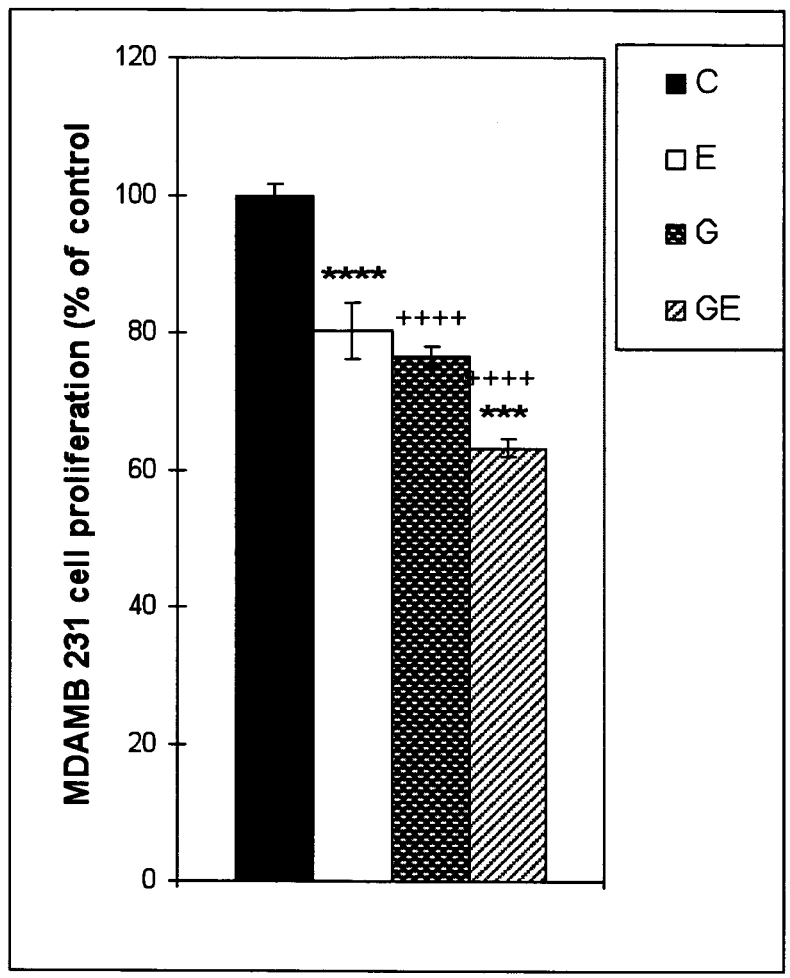

Genistein, which increases proliferation of cultured human mammary cancer MCF-7 cells similarly to the effect of estradiol, further potentiates que proliferative effect of the female hormone on these tumor cells so that cell proliferation induced by genistein plus estradiol is higher than that of estradiol alone of genistein alone (FIG. 23). Genistein, however, which slightly decreases the proliferation of cultured human mammary cancer MDAMB-231 cells similarly to the effect of estradiol, in association with estradiol the inhibitory effect is stronger than that of genistein alone or than the female hormone alone (FIG. 24).

Similarly to the antagonistic effect of genistein, soy extract potentiates estrogen-induced proliferative effect on MCF.7 human mammary cancer cells, although the stimulatory effect is slightly weaker than that of soy extract alone (FIG. 25). Soy extract decreases the proliferation of cultured human mammary cancer MDAMB-231 cells, but estradiol almost completely reverses this inhibitory effect of soy extract in this cell-line (FIG. 26).

These results on the effect of genistein and soy bean extracts reveal a dissociation of responses to estrogen. While the increase in RNA content in luminal epithelial cells and cell hypertrophy in luminal epithelial and myometrial cells were strongly induced by E, G or both S concentrations, uterine eosinophilia, endometrial edema and cell proliferation in luminal epithelium, glandular epithelium, endometrial stroma and myometrium were induced by E only, but not by G or S. This finding may have a myriad of explanations, it does not contradict with our hypothesis of the existence of different classes of ER which mediate separate group of responses to hormone stimulation. According to our hypothesis, some of these receptors may display high affinity for any specific phytoestrogen while other receptors may display low affinity, thus explaining the induction of some responses only. Alternatively, a specific phytoestrogen may display agonist action in its interaction with some ERs, while displaying antagonist action with other ERs.

The absence of estrogen induced uterine eosinophilia, and the cascade of responses mediated by the eosinophils, including endometrial edema, as shown in the present study, may be explained by the lack of recognition of the mesometrium (the main site of migration of eosinophils towards the uterus) (9-11, 13, 53) or by the decrease of their mobility through the uterine extravascular space towards myometrium and endometrium. Eosinophil recognition of uterine (mainly mesometrial) endothelium (53) is a ER-mediated process, where higher affinity ERs located in the surface of the eosinophils are involved (9). The lack of recognition of the uterine mesometrium may be either due to a low affinity of the phytoestrogen for this ER or by its antagonist action. Although we suggest that this is the main reason for lack of eosinophil migration to the uterus, an additional inhibition of eosinophil redistribution through the uterus from mesometrium may be suggested from present finding of increased proportion of eosinophils remaining in the mesometrium in animals treated with S or with G. The decreased migration of eosinophils from mesometrium to endometrium with myometrium is in agreement with the decrease in eosinophil degranulation in soybean extract treated rats, since hydrolytic enzyme release from degranulating eosinophils is required for eosinophil migration trough uterine ground substance (5, 9-11, 28).

Further, it was shown that the intensity of myometrial cell hypertrophy obtained with G and or highest dose of S are similar to that induced by E, while for cell hypertrophy and RNA content increase in luminal epithelium, this level of response is reached by G only. This may reflect a difference between the affinities of luminal epithelium and myometrial receptors, their structure, or a possible competitive inhibition by glycones or other phytoestrogens present in the extracts. The soybean ethanol extracts mainly contain the glucoside genistin, which is supposed to be devoid of estrogenic activity since it probably does not enter the intracellular space. Soybean genistin taken orally hydrolyzes in the intestine to its aglycone form genistein and enters circulation as such (51), displaying estrogenic activity (52). The weaker genomic responses induced by the extract as compared to genistein may be due to other phytoestrogens present in the crude soybean extract, to the partially hydrolyzed genistein from genistin (and/or its metabolites or glucuronides produced in vivo) or to genistin itself; further studies are necessary to evaluate this possibility.

The dissociation of responses to estrogen by phytoestrogens suggests their possible therapeutic application to induce clinically needed responses without inducing risk responses. Taking into consideration that cell-proliferation inducing activity of estrogen is the main estrogenic response considered to be at risk for cancer development in the post menopausal women, the absence of cell-proliferation in uterine luminal epithelial and glandular epithelial cells, in endometrial stromal an in myometrial cells by soy extracts and by genistein itself strongly suggest that these extracts/compounds would not share the estrogens' increased risk for endometrial cancer development in postmenopausal women.

The present results on genistein or soy extract on cultured human MCF-7 mammary cancer cells suggest however that genistein and/or soy extract (or its isoflavonoids) are not safe for use in the postmenopausal women as they may potentiate hormone-dependent breast cancer growth. On the contrary, the slight inhibitory effect on cultured MDAMB-231 human mammary cancer cells may show some kind of protection for this kind of breast cancer cells devoid of estrogen receptors alpha.

Our competitive study between genistein and estradiol show that G strongly inhibits estrogen-induced uterine eosinophilia and one of the non-genomic effects mediated by the eosinophils in the uterus (endometrial edema). Taking into consideration that G alone does not induce uterine eosinophilia, we suggest a competitive inhibition mechanism. E binding to eosinophil estrogen surface receptors is required for further recognition of uterine endothelial lining by the eosinophils in the presence of E, while G binding to the same receptors does not result in the response.

Our competitive studies also reveal that genistein strongly inhibits estrogen-induced proliferative response in uterine luminal epithelial, stromal and myometrial cells, similarly suggesting competitive inhibition mechanism. Although this effect may be convenient for endometrial cancer prevention, the association of G with estradiol (HRT in post menopause women, or endogenous E before menopause), the opposite effect of G on cultured human mammary cancer MCF-7 cells points to an increased risk for breast cancer development. In fact, our studies revealed that G, as well as soy extract, further enhances estrogen-induced cell proliferation of MCF-7 cells, suggesting an increased risk for G (or soy extracts) use in association with estradiol as HRT in women after menopause, or G use before menopause due to presence of endogenous E. Genistein or soy extract present an inhibitory effect on MDAMB-231 human mammary cell growth in culture, which is almost completely reversed by association of soy extract with estradiol. Above information warns that soy products should be used with caution or should not be used at all in women following menopause.

Example 4

Plant Extracts from *Calceolaria filicaulis*, *Adesmia verrucosa* and from *Fuchsia magellanica*

Extract Le81a (from *Calceolaria filicaulis*)

Extract Le81a, in female prepubertal rats, specifically inhibits estrogen-induce cell proliferation in myometrium, (FIG. 32) but does not modify the remaining estrogenic responses or slightly potentiates some of them (FIGS. 27-29 and 32). It slightly increases the degranulation of uterine eosinophils in estrogen-treated rats and increases the proportion of eosinophils located in endometrium (FIGS. 30 and 31). Besides, it inhibits the proliferation of MCF-7 and MDAMB-231 cultured human mammary cancer cells in the absence of estradiol (FIG. 33). This inhibition of tumor cells is almost completely reversed by estradiol in MCF-7 cells but not in MDAM-231 cells (FIG. 33).

Again, our results reveal a dissociation of various responses to estrogen in the uterus under the effect of Le81a. The novel finding of selective inhibition of estrogen-induced cell proliferation in myometrium, but not in other uterine cell-types, suggest a therapeutic application for treatment of uterine myomas by inhibiting cell proliferation in this tumor tissue. A possibility exists to use this extract as preventive for uterine myomas development.

The inhibition of growth of both human mammary cancer cell lines, MCF-7 and MDAMB-231, in the absence of estradiol, suggests a non-specific anti-tumor activity which may or may not be specific for mammary cancer. As a matter of fact, MCF-7 cells contain alpha and beta estrogen receptors, while MDAMB-231 cancer cells which are devoid of alpha estrogen receptors but do contain beta estrogen receptors. Although the antitumor effect may be specific for mammary gland originated tumor cells only, the possibility exists it may display antitumor activity for other cancer cells, possibility that should be explored. The almost complete reversal of the extract's antitumor activity by estradiol in MCF-7 cells, but not in MDAMB-231 cells suggest a possible role of estrogen alpha-receptors in estrogen-stimulated tumor growth in MCF-7 cells.

Extract Le179a (from *Adesmia verrucosa*)

Extract Le179a, in female prepubertal rats, specifically inhibits estrogen-induced cell proliferation in uterine luminal epithelial cells, glandular epithelial cells and myometrium (FIGS. 45-48). In glandular epithelium, it antagonizes 100% of estrogen-induced cell proliferation (FIGS. 46-47). On the contrary, the extract potentiates the remaining estrogenic responses (both, genomic and non-genomic responses to estrogen) (FIGS. 34-38), with the exception of uterine eosinophilia at 24 h after treatment (FIGS. 39-41); it inhibits eosinophil degranulation (FIG. 43) and increases the proportion of eosinophils located in the mesometrium as compared to those in endometrium with myometrium (FIG. 44), and increases the number of eosinophils located in mesometrium (FIG. 42). Further, in the absence of stimulation with estradiol, the extract itself induces myometrial cell hypertrophy, behaving as a selective estrogen response inducer (SERI), currently named SERM. The extract also causes an important inhibition of human cultured mammary cancer cells MC7 proliferation, both under estrogen stimulation or under conditions without estrogen stimulation, but causes a slight of human mammary cancer cells MDAMB-231 proliferation inhibition, cells devoid of alpha estrogen receptors (FIG. 49). Estradiol in association with the extract, cause an increase in MDAMB231 cell proliferation (FIG. 49).

Similarly with the above shown results, extract Le189a dissociates the different responses of estrogen in the uterus. The important selective inhibition of estradiol-induced cell proliferation in the different uterine cell-types that were investigated (uterine luminal epithelial, glandular epithelial and myometrial cells) as well as the important inhibition of human mammary cancer MCF-7 cells, but the potentiation of most remaining genomic and non-genomic responses to estrogen, indicates that extract Le179a is the most convenient candidate for hormone replacement therapy in post-menopause women, in association with other compounds displaying estrogen activity, including estradiol-17β. The complete inhibition of uterine glandular epithelium cell proliferation, and the important inhibition of estrogen-induced cell proliferation in the remaining uterine cell-types and of human breast cancer MCF-7 cells suggest that it can be used before menopause for hormone-dependent cancer prevention as well.

The inhibitory effect of Le179 on eosinophil degranulation, and on their migration from mesometrium towards myometrium and endometrium, may be used for diseases caused by eosinophil migration to various tissues and organs in allergic and hypersensitivity diseases or in hypereosinophilic syndrome. These therapeutic possibilities should be further investigated, taking into consideration that inhibition of eosinophil migration or degranulation should inhibit the development of edema in tissues such as respiratory airway, skin, and the tissues in asthmatic disease, allery and also preventing tissue damage in hypereosinophilic syndrome, or immune inhibition resulting from eosinophil degranulation in lymphoid organs (54). It perhaps may be used in other diseases related to eosinophils, such as chronic subdural hematoma Extracts Le22a and 185a, Decoctions 21a and 15a, and Extract Fractions 185a4, 3, 2, 1 (from *Fuchsia magellanica*)

Similarly with the above shown results, the extracts, decoctions and extract fractions dissociate the different responses of estrogen in the uterus; their action is similar although there are some differences between them. In the studies performed in the uterus of prepubertal rats, extract Le22a from plants collected in mid-summer, in the absence of estrogen stimulation, induces myometrial cell hypertrophy and endometrial edema (acting as a selective estrogen response inducer, SERI) and, when it is administered prior to treatment with estradiol, potentiates various estrogenic responses, including myometrial cell hypertrophy, cell proliferation in uterine luminal epithelium and myometrium, increases apoptosis in uterine glandular epithelium, and slightly potentiates estrogen/induced uterine eosinophilia at 6 h of hormone treatment while inhibits this response at 24 h of treatment. The decoction of the same plant species collected in mid-summer, diluted with ethanol, Le21a, in the absence of estrogen stimulation, also induces myometrial cell hypertrophy and endometrial edema (acting as a SERI) and, when it is administered prior to treatment with estradiol, also potentiates various estrogenic responses, including myometrial cell hypertrophy, cell proliferation in myometrium (there was no statistically significant differences for uterine luminal epithelium mitoses), but, as a difference to the effect of the extract, the decoction inhibits uterine eosinophilia at 6 and 24 h of hormone treatment.

Both the extract and the decoction, from plants collected in mid-summer, cause an important inhibition of cultured human mammary cancer cells MCF-7 cell proliferation, both in the presence of estrogenic stimulation or in its absence, and also antagonize cell proliferation of mammary cancer cells MDAMB-231. Of the extract fractions, the proliferation antagonist effect on MCF-7 cells was strongest with the most polar fraction, and the intensity of proliferation antagonism was slightly decreasing with less polar fractions. The inhibitory effect on MDAMB-231 cells was non-existent for the most polar fraction (Le185a4) and the less polar one (Le185a1), was the strongest with the second polar fraction (Le185a3) and less potent with the third one (Le185a2).

An extract from the same plant, collected in mid-fall (Le135a), display a very strong proliferation inhibitory activity for MCF-7 cells but does not reveal any effect on MDAMB-231 cells proliferation.

The above findings suggest the existence of at least two different agents inhibiting cell proliferation through different mechanisms. These two agents can be separated by extract fractioning. Comparison of extract 22a with decoction 21a shows that they are grossly similar, suggesting that a similar proportion of active agents are present in the extract and the decoction. The only difference that suggest that at least one component is lacking, is the total inhibition of estrogen-induced uterine eosinophilia at 6 and at 24 h of treatment with estradiol under the action of the decoction, while under the effect of the extract the response is potentiated at 6 h and inhibited at 24 h of treatment only. The stronger effect of the extract as compared to the decoction, for estrogen-induced mitoses in the different cell types may reflect an increased concentration of active components in the extract. The increase in the number of apoptosis in uterine glandular epithelium, displayed by the extract, suggest an antagonism to the increased mitoses in uterine luminal epithelium by the extract, and suggest that the extract may not display adverse effects in the uterus in the presence of estrogen stimulation. The most important finding is that the extract and the decoctions display an important antiproliferative effect in breast cancer cells in culture MCF-7, both in the presence or in the absence of estradiol, thus suggest its potential therapeutical use in hormone-dependent breast cancer treatment as well as its prevention in post menopause women. Additionally, the extract and the decoctions present an inhibitory effect on MDAMB-231 breast cancer cell proliferation, suggesting an additional therapeutical use as an antineoplasic drug. The dissociation of both effects (proliferation inhibition in MCF-7 cells and proliferation inhibition in MDAMB-231 cells) in the different extract fractions, or comparing extracts from plants collected in summer and those collected in fall, suggest the existence of at least two different active agents (or groups of active agents), one of them with a specificity for hormone-dependent MCF-7 breast cancer cells, and the other one with wider anti-cancerous action. Thus, the extract or its fractions open new therapeutic possibilities for breast cancer treatment, and perhaps for treatment of other, non hormone-dependent malignancies.

Toxicity Assays

A serial of increasing polarity extracts from *Fuchsia magellanica* were obtained and one of them was selected based on its biological activity (estrogenic responses in prepubertal rat uterus and activity in mammary cancer cells). Then, we performed a toxicological assay according to OECD 420 protocol, by administering 5000 mg/kg body wt to female rats. Histological examination demonstrated that this plant extract fraction was not toxic at the assayed dose. Toxicological assays with extracts obtained from *Adesmia verucosa* are under investigation.

As is suggested above, the plant extracts according to this disclosure can be used in various therapeutic purposes. Administration of the extracts can be made usually orally as a pharmaceutical or nutraceutical. Administration may in some cases also be parenteral (subcutaneous). Dosages and schedule should be determined in clinical studies and based on information from studies of bioavailability, area under the curve and disposition of the plant extracts and their components. The extracts may also be used in combinations to achieve the desired effects.

REFERENCES

1. Lyytinen H, Pukkala E, Ylikorkala O 2006 Breast cancer risk in postmenopausal women using estrogen-only therapy. Obstet Gynecol 108:1354-1360
2. Jensen E V, DeSombre E R 1972 Mechanism of action of the female sex hormones. Ann Rev Biochem 41:203-230
3. Tchernitchin A 1967 Autoradiographic study of (6,7)-3H oestradiol-17β incorporation into rat uterus. Steroids 10:661-668
4. Tchernitchin A 1972 Radioautographic study of the effect of estradiol-17β, estrone, estriol, progesterone, testosterone and corticosterone on the in vitro uptake of 2,4,6,7-3H estradiol-17β by uterine eosinophils of the rat. Steroids 19:575-586
5. Tchernitchin A 1973 Fine structure of rat uterine eosinophils and the possible role of eosinophils in the mechanism of estrogen action, J Steroid Biochem 4:277-282

6. Tchernitchin A, Roorijck J, Tchernitchin X, Vandenhende J & Galand P 1974 Dramatic early increase in uterine eosinophils after oestrogen administration. Nature 248:142-143
7. Tchernitchin A 1979. The role of eosinophil receptors in the non-genomic response to oestrogens in the uterus. J Steroid Biochem 11:417-424
8. Tchernitchin A N 1983 Eosinophil-mediated non-genomic parameters of estrogen stimulation: a separate group of responses mediated by an independent mechanism. J Steroid Biochem 19:95-100
9. Tchernitchin A N, Mena M A, Rodriguez A & Maturana M 1985 Radioautographic localization of estrogen receptors in the rat uterus: a tool for the study of classical and non-traditional mechanism of hormone action. In: Pertschuk L P, Lee S H, eds. Localization of Putative Steroid Receptors, Vol 1, Boca Raton, Fla.: CRC Press; 5-37
10. Tchernitchin A N, Barrera J, Arroyo P, Mena M A, Vilches K, Grunert G 1985 Degranulatory action of estradiol on blood eosinophil leukocytes in vivo and in vitro Agent Actions 17:60-66
11. Tchernitchin A N, Mena M A, Soto J, Unda C 1989 The role of eosinophils in the action of estrogens and other hormones. Med Sci Res 17:5-10
12. Galand P, Tchernitchin N, Tchernitchin A N 1985 Dissociation of uterine eosinophilia and water imbibition from other estrogen-induced responses by nafoxidine pretreatment. Mol Cell Endocrinol 42:227-233
13. López M, Castrillon M A, Tchernitchin A N 1986 Colloidal carbon blocks oestrogen-induced migration of eosinophils to the uterus and the uterine water imbibition response. J Endocrinol 109:89-95
14. Grunert G, Porcia M, Tchernitchin A N 1986 Differential potency of oestradiol-17β and diethylstilbestrol on separate groups of responses in ther at uterus. J Endocrinol 110:103-114
15. Pietras R J, Szego C M 1980 Partial purification and characterization of oestrogen receptors in subfractions of hepatocyte plasma membranes. Biochem J. 191:743-760
16. Nenci I, Fabris G, Marzola A, Marchetti E 1981 The plasma membrane as an additional level of stgeroid-cell interaction. J Steroid Biochem 15:231-234
17. Markaverich B M, Upchurch S, Clark J H 1981 Progesterone and dexamethasone antagonism of uterine growth: a role for a second nuclear binding site for estradiol in estrogen action. J Steroid Biochem 14:125-132
18. Sutherland R L, Murphy L C, San Foo M, Green M D, Whybourne A M 1980 High-affinity anti-oestrogen binding site distinct from the oestrogen receptor. Nature 288:273-275
19. Wang H, Masironi B, Eriksson H, Sahlin L 1999 A comparative study of estrogen receptors α and β in the rat uterus. Biol Reprod 61:955-965
20. Damdimopoulos A E, Spyrou G, Gustafsson J-Å 2008 Ligands differentially modify the nuclear mobility of estrogen receptors α and β. Endocrinology 149:339-345
21. Kuiper G G J M, Enmark E, Pelto-Huikko M, Nilsson S, Gustafsson J-Å 1996 Cloning of a novel estrogen receptor expressed in rat prostate and ovary. Proc Natl Acad Sci USA 93:5925-5930
22. Tchernitchin A N, Galand P 1983 Oestrogen levels in the blood, not in the uterus, determine uterine eosinophilia and oedema. J Endocrinol 99:123-130
23. Tchernitchin A, Tchernitchin X, Galand P 1975 Correlation of estrogen-induced uterine eosinophilia with other parameters of estrogen stimulation, produced with estradiol-17β and estriol. Experientia 31:993-994
24. Grunert G, Neumann G, Porcia M, Tchernitchin A N 1987 The estrogenic responses to clomiphene in the different cell-types of the rat uterus: Morphometrical evaluation. Biol Reprod 37:527-538
25. Galand P, Tchernitchin N, Tchernitchin A N 1984 Timecourse of the effects of nafoxidine and oestradiol on separate groups of responses in the uterus of the immature rat. J Steroid Biochem 21:43-47
26. Baumann P, Tchernitchin A N, Grunert G, Ball P 1986 Effect of various doses of catecholestrogens on uterine eosinophilia in the immature rat. Experientia 42:165-167
27. Tchernitchin A, Rooryck J, Tchernitchin X, Vandenhende J, Galand P 1975 Effects of cortisol on uterine eosinophilia and other oestrogenic responses. Mol Cell Endocrinol 2:331-337
28. Grunert G, Porcia M, Neumann G, Sepulveda S, Tchernitchin A N 1984 Progesterone interaction with eosinophils and with responses already induced by oestrogen in the uterus. J Endocrinol 102:295-303
29. Steinsapir J, Rojas A M, Alarcon O, Tchernitchin A N 1982 Effect of insulin and epinephrine on some early oestrogenic responses in the rat uterus. Acta Endocr (Kbh.) 99:263-271
30. Steinsapir J, Rojas A M, Mena M, Tchernitchin A N 1982 Effects of thyroid hormone on some uterine responses to estrogen. Endocrinology 110:1773-1779
31. Steinsapir J, Rojas A M, Tchernitchin A N 1982 Theophylline-estrogen interaction in the rat uterus. Role of the ovary. Am J Physiol 242:E121-E126
32. Unda C, Baeza C I, Arriagada R, Castrillon M A, Tchernitchin A N 1999 Bromocriptine modifies responses to estrogen in the rat uterus. Med Sci Res 27:319-323
33. Tchernitchin A N, Galand P 1982 Dissociation of separate mechanisms of estrogen action by actinomycin D. Experientia 38:511-513
34. Tchernitchin N N, Clayero A, Mena M A, Unda C, Villagra R, Cumsille M, Tchernitchin A N 2003 Effect of chronic exposure to lead on estrogen action in the prepubertal rat uterus. Environ Toxicol 18:268-277.
35. Bustos S, Soto J, Tchernitchin A N 1996 Estrogenic activity of p,p'-DDT. Environ Toxicol Water Qual 11:265-271
36. Adlercreutz H 2002 Phyto-oestrogens and cancer. Lancet Oncol 3:364-373
37. Probst-Hensch N M, Pike M C, McKean-Cowdin R, Stanczyk F Z, Kolonel L N, Henderson B 2000 Ethnic differences in post-menopausal plasma oestrogen levels: high estrone levels in Japanise-American women despite low wseight. Br J Cancer 82:1867-1870
38. Usui T 2006 Pharmaceutical prospects of phytoestrogens. Endocr J 53:7-20
39. Adlercreutz H 2002 Epidemiololgy of phytoestrogens. Baillieres Clin Endocrinol Metab 12:605-623
40. Mense S M, Hei T K, Ganju R K Bhat H K 2008 Phytoestrogens and breast cancer prevention: possible mechanisms of action. Environ Health Perspect 116:426-433
41 Wang H, Murphy P 1994 Isoflavone content in commercial soybean foods. J Agric Food Chem 42:1666-1673
42. Messina M J, Persky V, Setchell K D & Barnes S 1994 Soy intake and cancer risk: a review of the in vitro and in vivo data. Nutric Cancer 21:113-131
43. Adlercreutz C H, Goldin B R, Gorbach S L, Hockerstedt K A, Watanabe S, Hamalainen E K, Markkanen M H, Makela T H, Wahala T K, Adlercreutz T 1995 Soybean phytoestrogen intake and cancer risk. J Nutr 125 (3 Suppl): 757S-7705

44. Barnes S 1997 The chemopreventive properties of soy isoflavonoids in animal models of breast cancer. Breast Cancer Res Treat 46:169-179
45. Franke A A, Custer L J, Cerna C M & Narala K 1994 Rapid HPLC analysis of dietary phytoestrogens from legumes and from human urine. Proc Soc Exp Biol Med 208:18-26
46. Irvine C H, Fitzpatrick M G & Alexander S L 1998 Phytoestrogens in soy-based infant food: concentrations, daily intake, and possible biological effects. Proc Soc Exp Biol Med 217:247-253
47. Grunert G, Fernandez S, Tchernitchin A N 1984 Methods for the evaluation of responses to estrogen in individual cell types or regions of the uterus. Horm Res 19:253-262
48. Skehan P, Storeng R, Scudiero D, Monks A, McMahon J, Vistica D, Warren J T, Bokesch H, Kenney S, Boyd M R 1990 New colorimetric cytotoxicity assay for anticancer-drug screening. J Natl Cancer Inst 82:1107-1112
49. Vichai V, Kirtikara K 2006 Sulforhodamine B colorimetric assay for cytotoxicity screening. Nat Protoc 1:1112-1116.
50. Snedecor G W, Cochran W G 1967 Two-way classifications. In: Statistical Methods, Edn 6 Ames, Iowa State University Press; 299-338
51. Kelly G E, Joannou G E, Reeder A Y, Nelson C, Waring M A 1995 The variable metabolic response to dietary isoflavones in humans. Proc Soc Exp Biol Med 208:40-43
52. Zhang Y, Song T T, Cunnick J E, Murphy P A & Hendrich S 1999 Daidzein and genistein glucuronides in vitro are weakly estrogenic and activate human natural killer cell at nutritionally relevent concentrations. J Nutrit 129:399-405.
53. Soto N, Tchernitchin A 1979 Colchicine-estrogen interactions. Experientia 35:558-559
54. Tchernitchin A N, Carter W, Soto J, Baumann P 1990. Effect of eosinophil-degranulating estrogens on spleen eosinophils and white pulp/red pulp ratio. Agent Actions 31:249-256

What is claimed is:

1. A composition which inhibits in vitro estrogen-induced cell proliferation in myometrium;
   wherein said composition comprises an extract which is prepared by extracting aerial parts, including flowers, of each of *Calceolaria filicaulis, Adesmia verrucosa* and *Fuchsia magellanica* with an extractant selected from pure ethanol, water and a mixture of pure ethanol and water, and combining all of the extracts; wherein extraction occurs for about 72 hours and wherein the weight ratio of plant to extractant is in the range of 1:1 to 1:5.

2. The plant extract of claim 1, wherein extracting *Calceolaria filicaulis*, includes extracting *Calceolaria filicaulis* with pure ethanol.

3. The plant extract of claim 1, wherein extracting *Fuchsia magellanica* includes extracting *Fuchsia magellanica* with pure ethanol.

4. The composition of claim 1, wherein said composition further comprises saline.

5. The composition of claim 1, wherein said composition is in the form of an oral dosage form.

6. The composition of claim 1, wherein said composition is in the form of a parenteral dosage form.

7. The composition of claim 6, wherein the parenteral dosage form is a subcutaneous dosage form.

* * * * *